(12) United States Patent
O'Reilly et al.

(10) Patent No.: US 12,338,458 B2
(45) Date of Patent: Jun. 24, 2025

(54) USE OF THE IL-15/IL-15Rα COMPLEX IN THE GENERATION OF ANTIGEN-SPECIFIC T CELLS FOR ADOPTIVE IMMUNOTHERAPY

(71) Applicant: Memorial Sloan Kettering Cancer Center, New York, NY (US)

(72) Inventors: Richard John O'Reilly, Roxbury, CT (US); Bo Dupont, Harrison, NY (US); Aisha Nasreen Hasan, Blue Bell, PA (US); Annamalai Selvakumar, West Orange, NJ (US); Xiao-Rong Liu, Astoria, NY (US)

(73) Assignee: Memorial Sloan Kettering Cancer Center, New York, NY (US)

( * ) Notice: Subject to any disclaimer, the term of this patent is extended or adjusted under 35 U.S.C. 154(b) by 1309 days.

(21) Appl. No.: 16/616,099

(22) PCT Filed: May 25, 2017

(86) PCT No.: PCT/US2017/034364
§ 371 (c)(1),
(2) Date: Nov. 22, 2019

(87) PCT Pub. No.: WO2018/217203
PCT Pub. Date: Nov. 29, 2018

(65) Prior Publication Data
US 2020/0157502 A1 May 21, 2020

(51) Int. Cl.
*C12N 5/0783* (2010.01)
*A61K 40/10* (2025.01)
*A61K 40/11* (2025.01)
*A61K 40/24* (2025.01)
*A61K 40/46* (2025.01)
*C07K 14/725* (2006.01)

(52) U.S. Cl.
CPC ............ *C12N 5/0636* (2013.01); *A61K 40/10* (2025.01); *A61K 40/11* (2025.01); *A61K 40/24* (2025.01); *A61K 40/46* (2025.01); *C07K 14/7051* (2013.01); *C12N 5/0638* (2013.01); *C12N 2501/2315* (2013.01); *C12N 2502/11* (2013.01)

(58) Field of Classification Search
None
See application file for complete search history.

(56) References Cited

U.S. PATENT DOCUMENTS

| | | | |
|---|---|---|---|
| 6,723,695 B1 | 4/2004 | Burrows et al. | |
| 8,124,084 B2 | 2/2012 | Lefrancois et al. | |
| 8,425,898 B2 | 4/2013 | Sampson et al. | |
| 8,871,191 B2 | 10/2014 | Pavlakis et al. | |
| 8,940,288 B2 | 1/2015 | Lefrancois et al. | |
| 9,011,835 B2 | 4/2015 | Sampson et al. | |
| 9,279,017 B2* | 3/2016 | Raum | C07K 16/243 |
| 10,905,743 B2* | 2/2021 | Qu | C07K 19/00 |
| 2004/0265325 A1 | 12/2004 | Diamond et al. | |
| 2014/0086888 A1 | 3/2014 | Heslop et al. | |
| 2015/0093357 A1 | 4/2015 | Lefrancois et al. | |
| 2015/0139945 A1 | 5/2015 | Lefrancois et al. | |
| 2015/0359853 A1* | 12/2015 | Felber | A61P 37/04 |
| | | | 435/375 |
| 2019/0070264 A1* | 3/2019 | Qu | A61P 31/00 |

FOREIGN PATENT DOCUMENTS

| | | |
|---|---|---|
| CA | 2 970 385 C | 4/2023 |
| WO | WO 2007/084342 A2 | 7/2007 |
| WO | WO 2009/002562 A2 | 12/2008 |
| WO | WO 2010/059253 A2 | 5/2010 |
| WO | WO 2014/066527 A2 | 5/2014 |
| WO | WO 2016/018920 A1 | 2/2016 |
| WO | WO 2016/0955642 * | 6/2016 |

OTHER PUBLICATIONS

Chmielewski et al., Antigen-specific T-cell activation independently of the MHC: chimeric antigen receptor-redirected T cells Review Article; Front. Immunol., published: Nov. 11, 2013; pp. 1-7.*
Koehne et al., Abstracts / Biol Blood Marrow Transplant 22 (2016) S19eS481; S141 Targeting Wilms' Tumor 1 Protein Following CD34-Selected Allografts by Adoptive Transfer of Donor-Derived CTLs in Patients with Advanced Multiple Myeloma.*
Stoklasek et al., Combined IL-15/IL-15Rα Immunotherapy Maximizes IL-15 Activity In Vivo J Immunol. Nov. 1, 2006; 177(9):6072-6080.*
Motier et al Soluble Interleukin-15 Receptor (IL-15R)-sushi as a Selective and Potent Agonist of IL-15 Action through IL-15R/. Hyperagonist IL-15IL-15R Fusion Proteins the Journal of Biological Chemistry vol. 281, No. 3, pp. 1612-1619, Jan. 20, 2006.*
"Biological therapy in treating patients at high-risk or with lymphoma, lymphoproliferative disease, or malignancies," ClinicalTrials.gov, accessed at clinicaltrials.gov/ct2/show/NCT00002663?term=NCT00002663&rank=1, first received on Nov. 1, 1999, accessed on Oct. 21, 2014, 5 pages.
"Busulfan, melphalan, fludarabine and T-cell depleted allogeneic hematopoietic stem cell transplantation followed by post transplantation donor lymphocyte infusions," ClinicalTrials.gov, accessed at clinicaltrials.gov/ct2/show/NCT01131169?term=NCT01131169&rank=1, first received on May 25, 2010, accessed on Jan. 5, 2015, 5 pages.
"Dose escalation trial of WT1-sensitized T cells for residual or relapsed leukemia after allogeneic hematopoietic progenitor cell transplantation," ClinicalTrials.gov, accessed at clinicaltrials.gov/ct2/show/NCT00620633?term=NCT00620633&rank=1, first received on Feb. 11, 2008, accessed on Oct. 3, 2016, 4 pages.

(Continued)

*Primary Examiner* — Michael D Burkhart
(74) *Attorney, Agent, or Firm* — Foley & Lardner LLP

(57) ABSTRACT

Provided herein are methods of generating antigen-specific T cells for therapeutic administration to a human patient having or suspected of having a pathogen or cancer, utilizing soluble IL-15/IL-15Rα complexes ex vivo, in cell culture during ex vivo sensitizing of T cells to the antigen or during ex vivo culturing of antigen-specific T cells. Also disclosed are antigen-specific T cells generated by such methods, and methods of treating a human patient using such antigen-specific T cells. Cell culture systems comprising human T cells, antigen-presenting cells, and soluble IL-15/IL-15Rα complexes are also provided.

Figure 1:
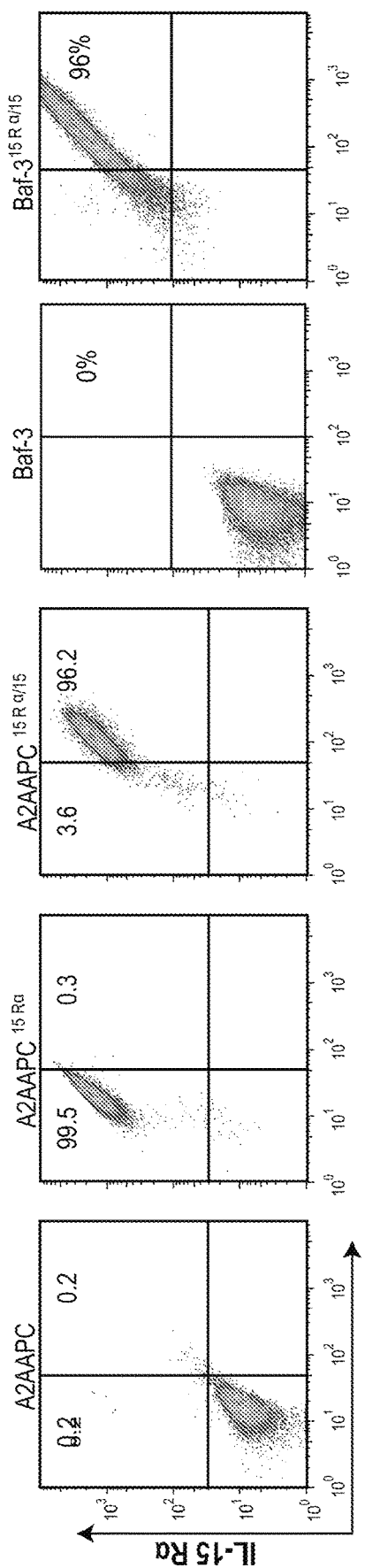

27 Claims, 20 Drawing Sheets
Specification includes a Sequence Listing.

(56) References Cited

OTHER PUBLICATIONS

"Dose escalation trial of WT1-specific donor-derived T cells following—cell depleted allogeneic hematopoietic stem cell transplantation for patients with relapsed/refractory multiple myeloma," ClinicalTrials. gov, accessed at clinicaltrials.gov/ct2/show/NCT01758328?term=NCT01758328&rank=1, first received on Dec. 24, 2012, accessed on Oct. 3, 2016, 4 pages.
"Form S-1 Registration Statement," filed with the United States Securities and Exchange Commission by Atara Biotherapeutics, Inc., dated Jun. 29, 2015, 203 pages.
"Primary transplant donor derived CMVpp65 specific T-cells for the treatment of CMV infection or persistent CMV viremia after allogeneic hematopoietic stem cell transplantation," ClinicalTrials. gov, accessed at clinicaltrials.gov/ct2/show/NCT01646645?term=NCT01646645&rank=1, first received on Jul. 18, 2012, accessed on Oct. 21, 2014, 4 pages.
"Therapeutic effects of Epstein-Barr virus immune T-lymphocytes derived from a normal HLA-compatible or partially-matched third-party donor in the treatment of EBV lymphoproliferative disorders and EBV-associated malignancies," ClinicalTrials.gov, accessed at clinicaltrials.gov/ct2/show/NCT01498484?term=NCT01498484 &rank=1, first received on Dec. 21, 2011, accessed on Oct. 21, 2014, 5 pages.
"Trial of third party donor derived CMVpp65 specific T-cells for the treatment of CMV infection or persistent CMV viremia after allogeneic hematopoietic stem cell transplantation," ClinicalTrials. gov, accessed at clinicaltrials.gov/ct2/show/NCT02136797?term=NCT02136797&rank=1, first received on May 9, 2014, accessed on Nov. 10, 2014, 4 pages.
Agger et al., Jan. 2007, "T cell homing to tumors detected by 3D-coordinated positron emission tomography and magnetic resonance imaging," J Immunother. 30(1):29-39.
Ahmed and Gray, Apr. 1996, "Immunological memory and protective immunity: understanding their relation," Science. 272(5258):54-60.
Amarnath and Fowler, Jan. 2012, "Harnessing autophagy for adoptive T cell therapy," Immunotherapy, 4(1):1-4.
American Association for Cancer Research (AACR) Press Release entitled "New T cell-based immunotherapy shows promise for lethal stem cell transplant complication," dated Apr. 19, 2015, 3 pages.
Balduzzi et al., Jul. 2011, "Polyomavirus JC-targeted T-cell therapy for progressive multiple leukoencephalopathy in a hematopoietic cell transplantation recipient," Bone Marrow Transplantation, 46(7):987-992.
Bao et al., Apr. 2012, "Adoptive immunotherapy with CMV specific cytotoxic T lymphocytes for stem cell transplant patients with refractory CMV infections," Journal of Immunotherapy, 35(3):293-298.
Barker et al., Dec. 2010, "Successful treatment of EBV-associated posttransplantation lymphoma after cord blood transplantation using third-party EBV-specific cytotoxic T lymphocytes," Blood. 116(23):5045-5049.
Bergamaschi et al., Feb. 2008, "Intracellular interaction of interleukin-15 with its receptor alpha during production leads to mutual stabilization and increased bioactivity," J Biol Chem. 283(7):4189-4199.
Berger et al., Jan. 2008, "Adoptive transfer of effector CD8+ T cells derived from central memory cells establishes persistent T cell memory in primates," J Clin Invest. 118(1):294-305.
Blyth et al., Nov. 2011, "BK virus-specific T cells for use in cellular therapy show specificity to multiple antigens and polyfunctional cytokine responses," Transplantation, 92(10):1077-1084.
Bonnet and Dick, Jul. 1997, "Human acute myeloid leukemia is organized as a hierarchy that originates from a primitive hematopoietic cell," Nat Med. 3(7):730-737.
Bontadini, A., Apr. 2012, "HLA techniques: typing and antibody detection in the laboratory of immunogenetics," Methods. 56(4):471-476.
Brentjens et al., Sep. 2007, "Genetically targeted T cells eradicate systemic acute lymphoblastic leukemia xenografts," Clin Cancer Res. 13(18 Pt 1):5426-5435.
Budhu et al., Jan. 2010, "CD8+ T cell concentration determines their efficiency in killing cognate antigen-expressing syngeneic mammalian cells in vitro and in mouse tissues," J Exp Med. 207(1):223-235.
Burkett et al., Oct. 2004, "Coordinate expression and trans presentation of interleukin (IL)-15Ralpha and IL-15 supports natural killer cell and memory CD8+ T cell homeostasis," J Exp Med. 200(7):825-834.
Burns and Crawford, Sep. 2004, "Epstein-Barr virus-specific cytotoxic T-lymphocytes for adoptive immunotherapy of post-transplant lymphoproliferative disease," Blood Reviews, 18(3):193-209.
Caruso et al., Jun. 2016, "Redirecting T-Cell Specificity to EGFR Using mRNA to Self-limit Expression of Chimeric Antigen Receptor," J Immunother. 39(5):205-217.
Chertova et al., Jun. 2013, "Characterization and favorable in vivo properties of heterodimeric soluble IL-15•IL-15Rα cytokine compared to IL-15 monomer," J Biol Chem. 288(25):18093-18103.
Cobbold et al., Aug. 2005, "Adoptive transfer of cytomegalovirus-specific CTL to stem cell transplant patients after selection by HLA-peptide tetramers," The Journal of Experimental Medicine, 202(3):379-386.
Comoli et al., Apr. 2002, "Infusion of autologous Epstein-Barr virus (EBV)-specific cytotoxic T cells for prevention of EBV-related lymphoproliferative disorder in solid organ transplant recipients with evidence of active virus replication," Blood, 99(7):2592-2598.
Cortivo et al., Nov. 2012, "Anti CMV and/or anti adenovirus IFN-g-positive CD4+ CD8+ T lymphocytes for treatment of viral infections after allogeneic HSC transplantation: first results," Blood, 120(21):1906.
Doubrovina et al., Nov. 2004, "In vitro stimulation with WT1 peptide-loaded Epstein-Barr virus-positive B cells elicits high frequencies of WT1 peptide-specific T cells with in vitro and in vivo tumoricidal activity," Clinical Cancer Research, 10(21):7207-7219.
Doubrovina et al., Nov. 2007, "Leukemia-reactive cytotoxic CD8+ and CD4+ T-cells specific for novel WT-1 epitopes are generated in vitro by sensitization with overlapping pentadecapeptides (15-mers) spanning the wilms tumor protein," Blood, 110 (11):1810.
Doubrovina et al., Aug. 2012, "Mapping of novel peptides of WT-1 and presenting HLA alleles that induce epitope-specific HLA-restricted T cells with cytotoxic activity against WT-1(+) leukemias," Blood. 120(8):1633-1646.
Doubrovina et al., Mar. 2012, "Adoptive immunotherapy with unselected or EBV-specific T cells for biopsy-proven EBV+ lymphomas after allogeneic hematopoietic cell transplantation," Blood, 119(11):2644-2656 (Published online Dec. 2, 2011).
Dubois et al., Nov. 2002, "IL-15Ralpha recycles and presents IL-15 in trans to neighboring cells," Immunity. 17(5):537-547.
Dunn, PP. Dec. 2011, "Human leucocyte antigen typing: techniques and technology, a critical appraisal," Int J Immunogenet. 38(6):463-473.
Einsele et al., Jun. 2002, "Infusion of cytomegalovirus (CMV)-specific T cells for the treatment of CMV infection not responding to antiviral chemotherapy," Blood, 99(11):3916-3922.
Eiz-Vesper et al., Jan. 2013, "Adoptive T-cell immunotherapy from third-party donors: characterization of donors and set up of a T-cell donor registry," Frontiers in Immunology, 3:410.
Epardaud et al., Apr. 2008, "Interleukin-15/interleukin-15R alpha complexes promote destruction of established tumors by reviving tumor-resident CD8+ T cells," Cancer Res. 68(8):2972-2983.
Epstein et al., 1994, "Human neural xenografts: progress in developing an in-vivo model to study human immunodeficiency virus (HIV) and human cytomegalovirus (HCMV) infection," Adv Neuroimmunol. 4(3):257-260.
Feuchtinger et al., Nov. 2010, "Adoptive transfer of pp65-specific T cells for the treatment of chemorefractory cytomegalovirus disease or reactivation after haploidentical and matched unrelated stem cell transplantation," Blood, 116(20):4360-4367 (Published online Jul. 12, 2010).
Gahn et al., Jan. 2002, "Immunotherapy to reconstitute immunity to DNA viruses," Seminars in Hematology, 39(1):41-47.

(56) References Cited

OTHER PUBLICATIONS

Gandhi et al., May 2007, "Immunity, homing and efficacy of allogeneic adoptive immunotherapy for posttransplant lymphoproliferative disorders," American Journal of Transplantation, 7(5):1293-1299 (Published online Apr. 8, 2007).
Gattinoni et al., Jun. 2005, "Acquisition of full effector function in vitro paradoxically impairs the in vivo antitumor efficacy of adoptively transferred CD8+ T cells," J Clin Invest. 115(6):1616-1626.
Gerdemann et al., Aug. 2012, "Rapidly generated multivirus-specific cytotoxic T lymphocytes for the prophylaxis and treatment of viral infections," Mol Ther. 20(8):1622-1632.
Gerdemann et al., Jan. 2013, "Immunotherapeutic strategies to prevent and treat human herpesvirus 6 reactivation after allogeneic stem cell transplantation," Blood, 121(1):207-218.
Gottschalk et al., Jan. 2015, "Adoptive T-cell immunotherapy," Current Topics in Microbiology and Immunology, 391:427-454.
Gupta et al., "Treatment of cytomegalovirus (CMV) retinitis with third party donor-derived CMV-specific cytotoxic T-lymphocytes," meeting abstract for ASRS 33rd Annual Meeting held Jul. 11- 14, 2015, Vienna, Austria, released on Jul. 1, 2015, 2 pages.
Gupta et al., Jan. 2015, "Treatment of cytomegalovirus retinitis with cytomegalovirus-specific T-lymphocyte infusion," Ophthalmic Surgery, Lasers & Imaging Retina, 46(1):80-82.
Haque et al., Oct. 2001, "Complete regression of posttransplant lymphoproliferative disease using partially HLA-matched Epstein Barr virus-specific cytotoxic T cells," Transplantation, 72(8):1399-1402.
Haque et al., Aug. 2002, "Treatment of Epstein-Barr-virus-positive post-transplantation lymphoproliferative disease with partly HLA-matched allogeneic cytotoxic T cells," Lancet, 360(9331):436-442.
Haque et al., Aug. 2007, "Allogeneic cytotoxic T-cell therapy for EBV-positive posttransplantation lymphoproliferative disease: results of a phase 2 multicenter clinical trial," Blood. 110(4):1123-1131.
Hasan et al., Aug. 2009, "A panel of artificial APCs expressing prevalent HLA alleles permits generation of cytotoxic T cells specific for both dominant and subdominant viral epitopes for adoptive therapy," The Journal of Immunology, 183(4):2837-2850 (Published online Jul. 27, 2009).
Hasan et al., Feb. 2010, "IL-15 Enhances In-Vitro Expansion and Functional Activity of Antigen-Specific Effector Memory T Cells (TEM) While Coexpression of IL-15 and IL-15 R on Antigen Presenting Cells Also Promotes Enrichment and Preferential Expansion of Central Memory T-CellS (Tcm)," BMT Abstract. S159 (1 page).
Hasan et al., Nov. 2013, "Generation and characterization of a third party GMP grade bank of CMV specific T-cells for adoptive immunotherapy of CMV infections in recipients of HSCT from cord blood or seronegative donors," Blood, 122(21):2021.
Hasan et al., Dec. 2014, "Banked, GMP grade third party T-cell lines specific for CMVpp65 epitopes presented by certain prevalent HLA alleles more consistently clear CMV infections in a genetically heterogeneous population of HSCT recipients," Blood, 124(21):309.
Hasan et al., Feb. 2014, "Generation and characterization of a third party GMP grade bank of CMV specific T-cells for adoptive immunotherapy of CMV infections in recipients of HSCT from cord blood or seronegative donors," Biology of Blood and Marrow Transplantation, 20(2):S131-S132.
Hasan et al., Nov. 2016, "Soluble and membrane-bound interleukin (IL)-15 Rα/IL-15 complexes mediate proliferation of high-avidity central memory CD8(+) T cells for adoptive immunotherapy of cancer and infections," Clin Exp Immunol. 186(2):249-265.
Hasan, "Banked, GMP grade third party T-cell lines specific for CMVpp65 epitopes presented by certain prevalent HLA alleles more consistently clear CMV infections in a genetically heterogeneous population of HSCT recipients," slide presentation on Dec. 8, 2014 at the 56th ASH Annual Meeting held Dec. 6-9, 2014, San Francisco, California, United States, 22 pages.
Heslop et al., May 1996, "Long-term restoration of immunity against Epstein-Barr virus infection by adoptive transfer of gene-modified virus-specific T lymphocytes," Nat Med. 2(5):551-555.
Heslop et al., Feb. 2010, "Long-term outcome of EBV-specific T-cell infusions to prevent or treat EBV-related lymphoproliferative disease in transplant recipients," Blood, 115(5):925-935 (Published online Oct. 30, 2009).
Holmes-Liew et al., Mar. 2015, "Adoptive T-cell immunotherapy for ganciclovir-resistant CMV disease after lung transplantation," Clinical & Translational Immunology, 4(3):e35.
Huang et al., May-Jun. 2005; "Survival, persistence, and progressive differentiation of adoptively transferred tumor-reactive T cells associated with tumor regression," J Immunother. 28(3):258-267.
Humar et al., Dec. 2009, "Cytomegalovirus in solid organ transplant recipients," American Journal of Transplantation, 9(Suppl 4):S78-S86.
Hunder et al, Jun. 2008, "Treatment of metastatic melanoma with autologous CD4+ T cells against NY-ESO-1," N Engl J Med. 358(25):2698-2703.
Hungtington et al., Jan. 2009, "IL-15 trans-presentation promotes human NK cell development and differentiation in vivo," J Exp Med. 206(1):25-34.
Huntington et al., Apr. 2011, "IL-15 transpresentation promotes both human T-cell reconstitution and T-cell-dependent antibody responses in vivo," Proc Natl Acad Sci U S A. 108(15):6217-6222.
Imamura et al., Aug. 2014, "Autonomous growth and increased cytotoxicity of natural killer cells expressing membrane-bound interleukin-15," Blood. 124(7):1081-1088.
Inoda et al., Apr. 2011, "Cytotoxic T lymphocytes efficiently recognize human colon cancer stem-like cells," Am J Pathol. 178(4):1805-1813.
International Search Report dated Nov. 29, 2019 of International Patent Application No. PCT/US2017/034364, filed May 25, 2017 (published as WO2018/217203), 5 pages.
Kawakami et al., Oct. 2005, "A case of immune recovery vitritis induced by donor leukocyte infusion for the treatment of cytomegalovirus retinitis," European Journal of Haematology, 75(4):352-354.
Kennedy et al., Mar. 2000, "Reversible defects in natural killer and memory CD8 T cell lineages in interleukin 15-deficient mice," J Exp Med. 191(5):771-780.
Kerry et al., Nov. 2003, "Interplay between TCR affinity and necessity of coreceptor ligation: high-affinity peptide-MHC/TCR interaction overcomes lack of CD8 engagement," J Immunol. 171(9):4493-4503.
Khanna et al., Aug. 1999, "Activation and adoptive transfer of Epstein-Barr virus-specific cytotoxic T cells in solid organ transplant patients with posttransplant lymphoproliferative disease," Proceedings of the National Academy of Sciences of the United States of America, 96(18):10391-10396.
Kim et al., Nov. 2007, "Dual roles of IL-15 in maintaining IL-7RalphalowCCR7-memory CD8+ T cells in humans via recovering the phosphatidylinositol 3-kinase/AKT pathway," J Immunol. 179(10):6734-6740.
Kiss et al., "Treatment of cytomegalovirus (CMV) retinitis with systemic infusion of third party donor-derived CMV-specific cytotoxic T-lymphocytes," meeting abstract for The Retina Society 48th Annual Scientific Meeting held Oct. 7-11, 2015, Paris, France, released Oct. 7, 2015, 1 page.
Klebanoff et al., Jul. 2005, "Central memory self/tumor-reactive CD8+ T cells confer superior antitumor immunity compared with effector memory T cells," Proc Natl Acad Sci U S A. 102(27):9571-9576.
Koehne et al., Jul. 2000, "Rapid selection of antigen-specific T lymphocytes by retroviral transduction," Blood. 96(1):109-117.
Koehne et al., Mar. 2002, "Quantitation, selection, and functional characterization of Epstein-Barr virus-specific and alloreactive T cells detected by intracellular interferon-gamma production and growth of cytotoxic precursors," Blood. 99(5):1730-1740.
Koehne et al., Apr. 2003, "Serial in vivo imaging of the targeted migration of human HSV-TK-transduced antigen-specific lymphocytes," Nat Biotechnol. 21(4):405-413.
Koehne et al., Sep. 2015, "Immunotherapy with donor T cells sensitized with overlapping pentadecapeptides for treatment of

(56) References Cited

OTHER PUBLICATIONS persistent cytomegalovirus infection or viremia," Biology of Blood and Marrow Transplantation, 21(9):1663-1678 (Published online May 29, 2015).
Kokaji et al., Apr. 2008, "IL-15 transpresentation augments CD8+ T cell activation and is required for optimal recall responses by central memory CD8+ T cells," J Immunol. 180(7):4391-4401.
Kozak, M., Aug. 1987, "At least six nucleotides preceding the AUG initiator codon enhance translation in mammalian cells," J Mol Biol. 196(4):947-950.
Kunert et al., Nov. 2013, "TCR-Engineered T Cells Meet New Challenges to Treat Solid Tumors: Choice of Antigen, T Cell Fitness, and Sensitization of Tumor Milieu," Front Immunol. 4:363.
Kuo et al., "WS/PP-109-04: Role of central memory and effector memory CD8 T cells in adoptive cell therapy," presented at 14th International Congress of Immunology, Friday Aug. 27, 2010, Kobe, Japan, Poster Abstract, 3 pages.
Kuo et al. "WS/PP-109-04 Role of central memory and effector memory CD8 T cells in adoptive cell therapy," presented at 14th International Congress of Immunology, Monday Aug. 23, 2010, Kobe, Japan, Poster Abstract, 3 pages.
Lange et al., Jan. 2014, "Cost-efficient high-throughput HLA typing by MiSeq amplicon sequencing," BMC Genomics. 15: 63.
Lapidot et al., Feb. 1994, "A cell initiating human acute myeloid leukaemia after transplantation into SCID mice," Nature. 367(6464):645-648.
Latouche and Sadelain, Apr. 2000, "Induction of human cytotoxic T lymphocytes by artificial antigen-presenting cells," Nat Biotechnol. 18(4):405-409.
Leen et al, Jun. 2013, "Multicenter study of banked third-party virus-specific T cells to treat severe viral infections after hematopoietic stem cell transplantation," Blood, 121(26):5113-5123 (Published online Apr. 22, 2013).
Leen et al., Oct. 2006, "Monoculture-derived T lymphocytes specific for multiple viruses expand and produce clinically relevant effects in immunocompromised individuals," Nature Medicine, 12(10):1160-1166 (Published online Sep. 24, 2006).
Lischka et al., Mar. 2010, "In vitro and in vivo activities of the novel anticytomegalovirus compound AIC246," Antimicrob Agents Chemother. 54(3):1290-1297.
Liu et al., May 2013, "IL-15 in tumor microenvironment causes rejection of large established tumors by T cells in a noncognate T cell receptor-dependent manner," Proc Natl Acad Sci U S A. 110(20):8158-8163.
Louis et al., Nov.-Dec. 2010, "Adoptive transfer of EBV-specific T cells results in sustained clinical responses in patients with locoregional nasopharyngeal carcinoma," Journal of Immunotherapy, 33(9):983-990.
Lucas et al., Mar. 1996, "The development of cellular immunity to Epstein-Barr virus after allogeneic bone marrow transplantation," Blood, 87(6):2594-2603.
Macesic et al., Mar. 2015, "Adoptive T cell immunotherapy for treatment of ganciclovir-resistant cytomegalovirus disease in a renal transplant recipient," American Journal of Transplantation, 15(3):827-832 (Published online Feb. 3, 2015).
Micklethwaite et al., Jun. 2007, "Ex vivo expansion and prophylactic infusion of CMV-pp65 peptide-specific cytotoxic T-lymphocytes following allogeneic hematopoietic stem cell transplantation," Biology of Blood and Marrow Transplantation, 13(6):707-714 (Published Apr. 6, 2007).
Mocarski et al., Jan. 1993, "Human cytomegalovirus in a SCID-hu mouse: thymic epithelial cells are prominent targets of viral replication," Proc Natl Acad Sci U S A. 90(1):104-108.
Morgan et al., Oct. 2006, "Cancer regression in patients after transfer of genetically engineered lymphocytes," Science. 314(5796):126-129.
Mortier et al., May 2008, "IL-15Ralpha chaperones IL-15 to stable dendritic cell membrane complexes that activate NK cells via trans presentation," J Exp Med. 205(5):1213-1225.
Mortier et al., Nov. 2009, "Macrophage- and dendritic-cell-derived interleukin-15 receptor alpha supports homeostasis of distinct CD8+ T cell subsets," Immunity. 31(5):811-822.
Mortier et al., Jan. 2006, "Soluble interleukin-15 receptor alpha (IL-15R alpha)-sushi as a selective and potent agonist of IL-15 action through IL-15R beta/gamma," Hyperagonist IL-15×IL-15R alpha fusion proteins, J Biol Chem. 281(3):1612-1619.
Mortier et al., Aug. 2004, "Natural, proteolytic release of a soluble form of human IL-15 receptor alpha-chain that behaves as a specific, high affinity IL-15 antagonist," J Immunol. 173(3):1681-1688.
Oh et al., Mar. 2003, "Selective induction of high avidity CTL by altering the balance of signals from APC," J. Immunol. 170(5):2523-2530.
O'Reilly et al., May 2007, "Adoptive transfer of antigen-specific T-cells of donor type for immunotherapy of viral infections following allogeneic hematopoietic cell transplants," Immunologic Research, 38(1-3):237-250.
O'Reilly et al., Jun. 2010, "Adoptive transfer of unselected or leukemia-reactive T-cells in the treatment of relapse following allogeneic hematopoietic cell transplantation," Seminars in Immunology, 22(3):162-172 (Published online May 26, 2010).
O'Reilly et al., Sep. 2011, "Novel strategies for adoptive therapy following HLA disparate transplants," Best Practice & Research Clinical Haematology, 24(3):381-391.
O'Reilly et al., Jun. 2015, "T-cell depleted allogeneic hematopoietic cell transplants as a platform for adoptive therapy with leukemia selective or virus-specific T-cells," Bone Marrow Transplant, 50(Suppl 2):S43-S50.
O'Reilly, meeting abstract for the oral presentation on Oct. 31, 2014 at the 76th Annual Meeting of the Japanese Society of Hematology, held Oct. 31-Nov. 2, 2014, Osaka, Japan, 1 page.
Papadopoulou et al., Jun. 2014, "Activity of broad-spectrum T cells as treatment for AdV, EBV, CMV, BKV, and HHV6 infections after HSCT," Science Translational Medicine, 6(242):242ra83.
Park et al., Nov. 2011, "Treating cancer with genetically engineered T cells," Trends Biotechnol. 29(11):550-557.
Peggs et al., Oct. 2003, "Adoptive cellular therapy for early cytomegalovirus infection after allogeneic stem-cell transplantation with virus-specific T-cell lines," Lancet, 362(9393):1375-1377.
Perna et al., Jan. 2013, "Interleukin 15 provides relief to CTLs from regulatory T cell-mediated inhibition: implications for adoptive T cell-based therapies for lymphoma," Clin Cancer Res. 19(1):106-117.
Petersen et al., May-Jun. 2006, "Accumulation in tumor tissue of adoptively transferred T cells: A comparison between intravenous and intraperitoneal injection," J Immunother. 29(3):241-249.
Votavola et al., May-Jun. 2014, "Increasing the biological activity of IL-2 and IL-15 through complexing with anti-IL-2 mAbs and IL-15Rα-Fc chimera," Immunol Lett. 159(1-2):1-10.
Prockop et al., "Banked EBV-specific T-cells from HLA-partially matched normal donors induce durable remissions of rituximab refractory EBV+ B-cell lymphomas post hematopoietic and organ allografts," meeting abstract for the 2015 ASCO Anual Meeting held May 29-Jun. 2, 2015, Chicago, Illinois, United States, published May 20, 2015 (the same abstract was published online early on May 13, 2015), 2 pages.
Prockop et al., "Epstein-Barr virus-specific cytotoxic T lymphocytes for treatment of rituximab-refractory Epstein-Barr virus-associated lymphoproliferative disorder," meeting abstract for the 2015 AACR Anual Meeting held Apr. 18-22, 2015, Philadelphia, Pennsylvania, United States, published Mar. 18, 2015, 2 pages.
Prockop et al., Dec. 2014, "Third party donor derived CMV specific T cells for the treatment of refractory CMV viremia and disease after hematopoietic stem cell transplant," Blood, 124(21):184.
Prockop et al., Feb. 2014, "Third party donor derived EBV specific T cells for the treatment of refractory EBV-related post-transplant lymphomas," Biology of Blood and Marrow Transplantation, 20(2):S49-S50.
Prockop et al., 2014, "Third party donor derived CMV specific T cells for the treatment of refractory CMV viremia and disease after hematopoietic stem cell transplant," meeting abstract for the 56th American Society of Hematology (ASH) Annual Meeting and

(56) References Cited

OTHER PUBLICATIONS

Exposition held in San Francisco, California, Dec. 6-9, 2014, first published online on Nov. 6, 2014, 27 pages.
Prockop et al., Dec. 2015, "Successful treatment of refractory CMV chorioretinitis and meningoencephalitis with adoptive transfer of third party CMVpp65 specific T-cell lines," Blood, 126(23):3157.
Prockop et al., 2015, "Successful treatment of refractory CMV chorioretinitis and meningoencephalitis with adoptive transfer of third party CMVpp65 specific T-cell lines," meeting abstract for the 57th American Society of Hematology (ASH) Annual Meeting and Exposition held in Orlando, Florida, Dec. 5-8, 2015, first published online on Nov. 5, 2015, 3 pages.
Prockop, "3rd party CMV specific T cells for the treatment of refractory CMV viremia and disease after HSCT," slide presentation on Dec. 7, 2014 at the 56th ASH Annual Meeting held Dec. 6-9, 2014, San Francisco, California, United States, 27 pages.
Prockop, "Adoptive immunotherapy with banked virus specific 3rd party donor T-cells for CMV infections and EBV LPD complicating hematopoietic cell transplants," slide presentation on Oct. 31, 2014 at the 76th Annual Meeting of the Japanese Society of Hematology, held Oct. 31-Nov. 2, 2014, Osaka, Japan, 43 pages.
Prockop, "Banked EBV-specific T-cells from HLA-partially matched normal donors induce durable remissions of rituximab refractory EBV+ B-cell lymphomas post hematopoietic and organ allografts," slide presentation on Jun. 1, 2015 at the 2015 ASCO Anual Meeting held May 29-Jun. 2, 2015, Chicago, Illinois, United States, 18 pages.
Prockop, "Epstein-Barr virus (EBV)-specific cytotoxic T lymphocytes (EBV-CTLs) for treatment of rituximab-refractory EBV-associated lymphoproliferative disorder (EBV-LPD)," slide presentation on Apr. 19, 2015 at the 2015 AACR Anual Meeting held Apr. 18-22, 2015, Philadelphia, Pennsylvania, United States, 25 pages.
Prockop, "Third party donor derived EBV specific T cells for the treatment of refractory lymphoma in immunodeficient recipients," slide presentation on Mar. 1, 2014 at the ASBMT 2014 BMT Tandem Meetings held Feb. 26-Mar. 2, 2014, Grapevine, Texas, United States, 22 pages.
Prockop, "Third party donor T cells for the treatment of CMV infection and EBV lymphoma in immunodeficient patients," slide presentation on May 22, 2014 at the 9th Meeting of the EBMT Pediatric Diseases WP, held May 21-23, 2014, Jerusalem, Israel, 47 pages.
Qasim et al., May 2013, "Interferon-γ capture T cell therapy for persistent Adenoviraemia following allogeneic haematopoietic stem cell transplantation," British Journal of Haematology, 161(3):449-452 (Published online Feb. 22, 2013).
Quinn et al., Feb. 2015, "Memory T cells specific for murine cytomegalovirus re-emerge after multiple challenges and recapitulate immunity in various adoptive transfer scenarios," J Immunol. 194(4):1726-1736.
Ramos et al., Jan. 2013, "Human papillomavirus type 16 E6/E7-specific cytotoxic T lymphocytes for adoptive immunotherapy of HPV-associated malignancies," Journal of Immunotherapy, 36(1):66-76.
Rodriguez-Tarduchy et al., Sep. 1990, "Regulation of apoptosis in interleukin-3-dependent hemopoietic cells by interleukin-3 and calcium ionophores," EMBO J. 9(9):2997-3002.
Romano et al., May 2012, "Human Langerhans cells use an IL-15R-α/IL-15/pSTAT5-dependent mechanism to break T-cell tolerance against the self-differentiation tumor antigen WT1," Blood. 31;119(22):5182-5190.
Rooney et al., Jan. 1995, "Use of gene-modified virus-specific T lymphocytes to control Epstein-Barr-virus-related lymphoproliferation," Lancet, 345(8941):9-13.
Rooney et al., Sep. 1998, "Infusion of cytotoxic T cells for the prevention and treatment of Epstein-Barr virus-induced lymphoma in allogeneic transplant recipients," Blood, 92(5):1549-1555.
Rosenberg and Dudley, Oct. 2004, "Cancer regression in patients with metastatic melanoma after the transfer of autologous antitumor lymphocytes," Proc Natl Acad Sci U S A. 101 Suppl 2:14639-14645.
Rosenberg et al., Dec. 1988, "Use of tumor-infiltrating lymphocytes and interleukin-2 in the immunotherapy of patients with metastatic melanoma. A preliminary report," N Engl J Med. 319(25):1676-1680.
Rowley et al., Feb. 2009, "Expression of IL-15RA or an IL-15/IL-15RA fusion on CD8+ T cells modifies adoptively transferred T-cell function in cis," Eur J Immunol. 39(2):491-506.
Roychowdhury et al., Nov. 2004, "Failed adoptive immunotherapy with tumor-specific T cells: reversal with low-dose interleukin 15 but not low-dose interleukin 2," Cancer Res. 64(21):8062-8067.
Rubinstein et al., Jun. 2006, Converting IL-15 to a superagonist by binding to soluble IL-15R{alpha}. Proc Natl Acad Sci U S A. 103(24): 9166-9171.
Sadelain et al., Apr. 2013, "The basic principles of chimeric antigen receptor design," Cancer Discov. 3(4):388-398.
Sato et al., Jun. 2007, "Genome sequencing and genome resources in model legumes," Plant Physiol. 144(2):588-593.
Schluns and Lefrancois, Apr. 2003, "Cytokine control of memory T-cell development and survival," Nat Rev Immunol. 3(4):269-279.
Schluns et al., May 2002, "Cutting edge: requirement for IL-15 in the generation of primary and memory antigen-specific CD8 T cells," J Immunol. 168(10):4827-4831.
Schluns et al., Feb. 2004, "Transregulation of memory CD8 T-cell proliferation by IL-15Ralpha+ bone marrow-derived cells," Blood. 103(3):988-994.
Schmitt et al., Mar. 2011, "Adoptive transfer and selective reconstitution of streptamer-selected cytomegalovirus-specific CD8+ T cells leads to virus clearance in patients after allogeneic peripheral blood stem cell transplantation," Transfusion, 51(3):591-599 (Published online Dec. 6, 2010).
Sharpe and Mount, Apr. 2015, "Genetically modified T cells in cancer therapy: opportunities and challenges," Dis Model Mech. 8(4):337-350.
Sili et al., Jan. 2012, "Production of good manufacturing practice-grade cytotoxic T lymphocytes specific for Epstein-Barr virus, cytomegalovirus and adenovirus to prevent or treat viral infections post-allogeneic hematopoietic stem cell transplant," Cytotherapy, 14(1):7-11.
Sprent and Surh, Apr. 2001, "Generation and maintenance of memory T cells," Curr Opin Immunol. 13(2):248-254.
Stauss et al., Oct. 2015, "Cancer gene therapy with T cell receptors and chimeric antigen receptors," Curr Opin Pharmacol. 24:113-118.
Stemberger et al., Jul. 2014, "Lowest numbers of primary CD8(+) T cells can reconstitute protective immunity upon adoptive immunotherapy," Blood. 124(4):628-637.
Stoklasek et al., Nov. 2006, "Combined IL-15/IL-15Ralpha immunotherapy maximizes IL-15 activity in vivo," J Immunol. 177(9):6072-6080.
Stone et al., 2012, "T cell receptor engineering," Methods Enzymol. 503:189-222.
Straathof et al., Mar. 2005, "Treatment of nasopharyngeal carcinoma with Epstein-Barr virus—specific T lymphocytes," Blood, 105(5):1898-1904 (Published online Nov. 12, 2004).
Sukdolak et al., Oct. 2013, "CMV-, EBV- and ADV-specific T cell immunity: screening and monitoring of potential third-party donors to improve post-transplantation outcome," Biology of Blood and Marrow Transplantation, 19(10):1480-1492 (Published online Jul. 23, 2013).
Surh and Sprent, Dec. 2008, "Homeostasis of naive and memory T cells," Immunity, 19;29(6):848-862.
Tamzalit et al., Jun. 2014, IL-15.IL-15Rα complex shedding following trans-presentation is essential for the survival of IL-15 responding NK and T cells. Proc Natl Acad Sci U S A 111(23):8565-8570.
Traitanon et al., Jun. 2014, "IL-15 induces alloreactive CD28(−) memory CD8 T cell proliferation and CTLA4-Ig resistant memory CD8 T cell activation," Am J Transplant. 14(6):1277-1289.
Trivedi et al., Apr. 2005, "Generation of CMV-specific T lymphocytes using protein-spanning pools of pp65-derived overlapping

(56) References Cited

OTHER PUBLICATIONS pentadecapeptides for adoptive immunotherapy," Blood, 105(7):2793-2801 (Published online Oct. 28, 2004).

Tse and Kwong, Jan. 2015, "Epstein Barr virus-associated lymphoproliferative diseases: the virus as a therapeutic target," Experimental & Molecular Medicine, 47:e136.

Uhlin et al., Oct. 2012, "Rapid salvage treatment with virus-specific T cells for therapy-resistant disease," Clinical Infectious Diseases, 55(8):1064-1073 (Published online Jul. 17, 2012).

Van Den Bergh et al., Feb. 2017, "IL-15 receptor alpha as the magic wand to boost the success of IL-15 antitumor therapies: The upswing of IL-15 transpresentation," Pharmacol Ther. 170:73-79.

Waldmann et al., Feb. 2001, "Contrasting roles of IL-2 and IL-15 in the life and death of lymphocytes: implications for immunotherapy," Immunity. 14(2):105-110.

Waldrop et al., Apr. 1997, "Determination of antigen-specific memory/effector CD4+ T cell frequencies by flow cytometry: evidence for a novel, antigen-specific homeostatic mechanism in HIV-associated immunodeficiency," Journal of Clinical Investigation, 99(7):1739-1750.

Walter et al., Oct. 1995, "Reconstitution of cellular immunity against cytomegalovirus in recipients of allogeneic bone marrow by transfer of T-cell clones from the donor," The New England Journal of Medicine, 333(16):1038-1044.

Wherry et al., Mar. 2003, "Lineage relationship and protective immunity of memory CD8 T cell subsets," Nat Immunol. 4(3):225-234.

Wilkie et al., Jul.-Aug. 2004, "Establishment and characterization of a bank of cytotoxic T lymphocytes for immunotherapy of epstein-barr virus-associated diseases," Journal of Immunotherapy, 27(4):309-316.

Wolfl et al., Feb. 2011, "Primed tumor-reactive multifunctional CD62L+ human CD8+ T cells for immunotherapy," Cancer Immunol Immunother. 60(2):173-186.

Written Opinion dated Nov. 29, 2019 of International Patent Application No. PCT/US2017/034364, filed May 25, 2017 (published as WO2018/217203), 6 pages.

Xu et al., May 2013, "Efficacy and mechanism-of-action of a novel superagonist interleukin-15: interleukin-15 receptor αSu/Fc fusion complex in syngeneic murine models of multiple myeloma," Cancer Res. 15;73(10):3075-3086.

Yu et al., Dec. 2010, "Simultaneous blockade of multiple immune system inhibitory checkpoints enhances antitumor activity mediated by interleukin-15 in a murine metastatic colon carcinoma model," Clin Cancer Res. 16(24):6019-6028.

Yu et al., Apr. 2012, "Simultaneous inhibition of two regulatory T-cell subsets enhanced Interleukin-15 efficacy in a prostate tumor model," Proc Natl Acad Sci U S A. 109(16):6187-6192.

Zhang et al., May 1998, "Potent and selective stimulation of memory-phenotype CD8+ T cells in vivo by IL-15," Immunity. 8(5):591-599.

Zhang et al., Jun. 2012, "Augmented IL-15Rα expression by CD40 activation is critical in synergistic CD8 T cell-mediated antitumor activity of anti-CD40 antibody with IL-15 in TRAMP-C2 tumors in mice," J Immunol. 188(12):6156-6164.

Takai, Aug. 2002, "Roles of Fc receptors in autoimmunity," Nature 2(8): 580-592.

Tamzalit et al., 2014, "IL-15.IL-15Rα complex shedding following trans-presentation is essential for the survival of IL-15 responding NK and T cells," PNAS 111(23):8565-8570.

\* cited by examiner

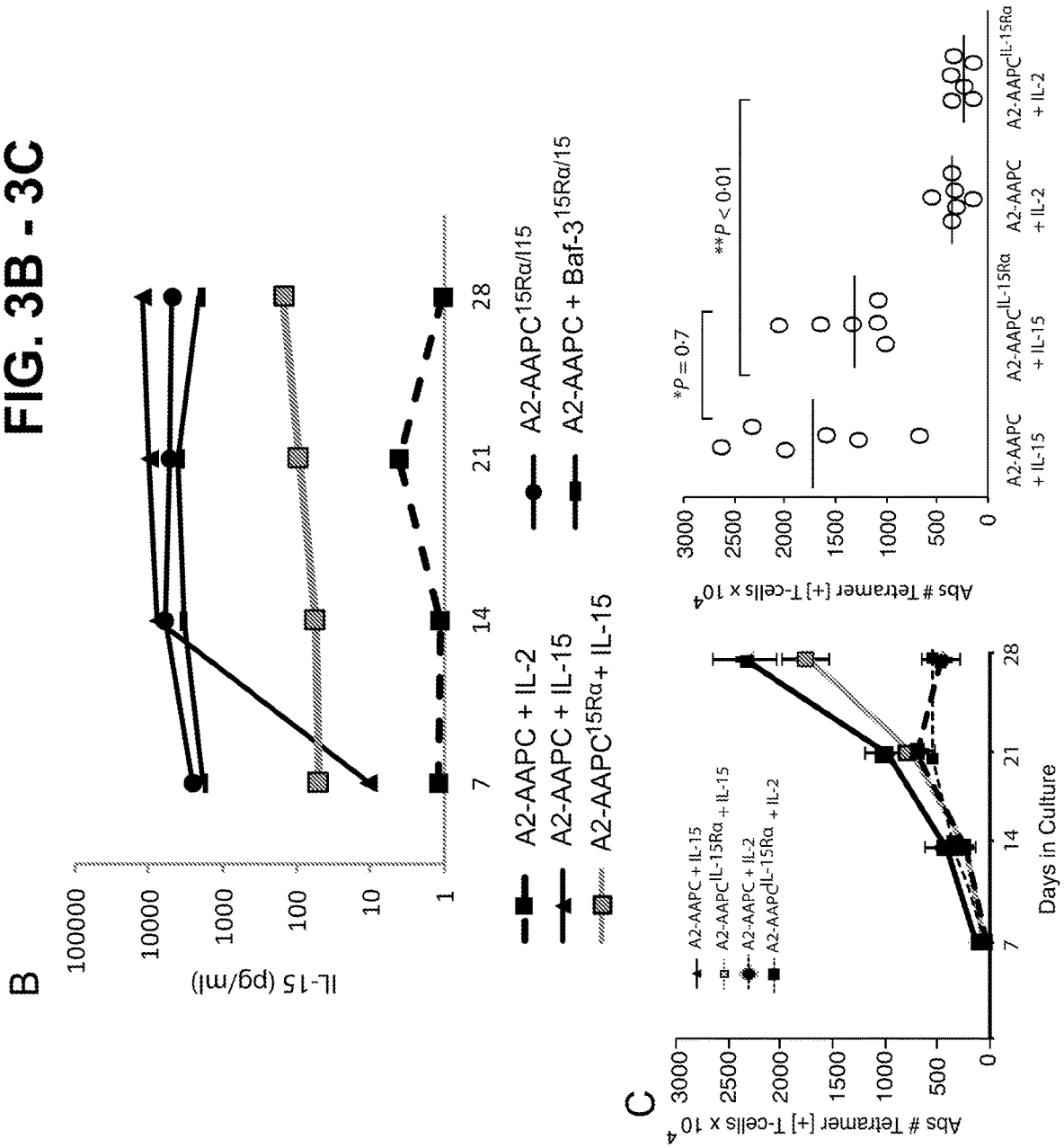

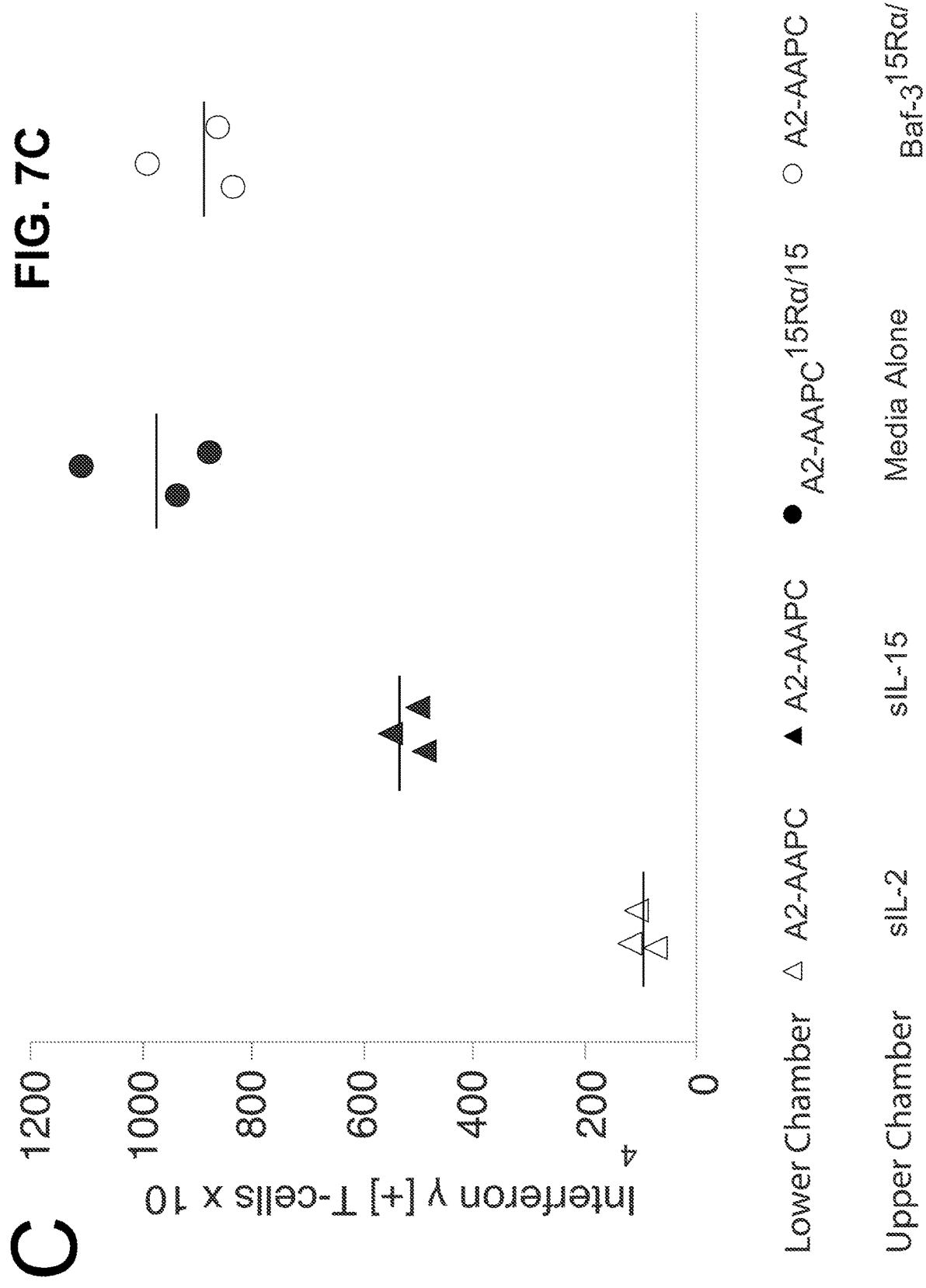

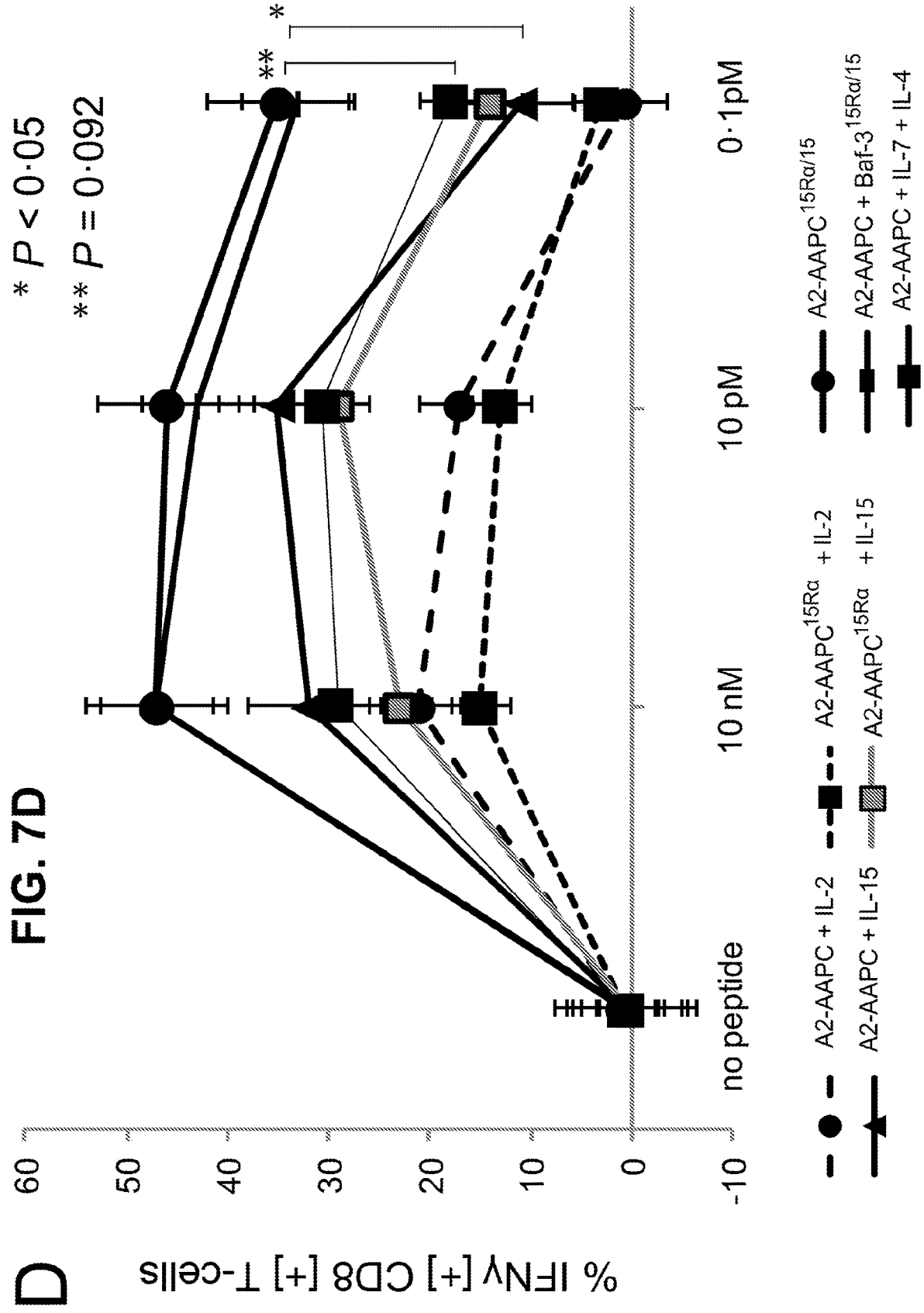

SEQUENCE LISTING

```
<160> NUMBER OF SEQ ID NOS: 7

<210> SEQ ID NO 1
<211> LENGTH: 162
<212> TYPE: PRT
<213> ORGANISM: homo sapiens
<220> FEATURE:
<223> OTHER INFORMATION: human interleukin-15 isoform 1 preproprotein
<300> PUBLICATION INFORMATION:
<308> DATABASE ACCESSION NUMBER: NP_000576.1
<309> DATABASE ENTRY DATE: 2017-04-30
<313> RELEVANT RESIDUES IN SEQ ID NO: (1)..(162)

<400> SEQUENCE: 1

Met Arg Ile Ser Lys Pro His Leu Arg Ser Ile Ser Ile Gln Cys Tyr
1               5                   10                  15
```

```
Leu Cys Leu Leu Leu Asn Ser His Phe Leu Thr Glu Ala Gly Ile His
            20                  25                  30

Val Phe Ile Leu Gly Cys Phe Ser Ala Gly Leu Pro Lys Thr Glu Ala
            35                  40                  45

Asn Trp Val Asn Val Ile Ser Asp Leu Lys Lys Ile Glu Asp Leu Ile
50                  55                  60

Gln Ser Met His Ile Asp Ala Thr Leu Tyr Thr Glu Ser Asp Val His
65                  70                  75                  80

Pro Ser Cys Lys Val Thr Ala Met Lys Cys Phe Leu Leu Glu Leu Gln
            85                  90                  95

Val Ile Ser Leu Glu Ser Gly Asp Ala Ser Ile His Asp Thr Val Glu
            100                 105                 110

Asn Leu Ile Ile Leu Ala Asn Asn Ser Leu Ser Ser Asn Gly Asn Val
            115                 120                 125

Thr Glu Ser Gly Cys Lys Glu Cys Glu Glu Leu Glu Glu Lys Asn Ile
            130                 135                 140

Lys Glu Phe Leu Gln Ser Phe Val His Ile Val Gln Met Phe Ile Asn
145                 150                 155                 160

Thr Ser

<210> SEQ ID NO 2
<211> LENGTH: 135
<212> TYPE: PRT
<213> ORGANISM: homo sapiens
<220> FEATURE:
<223> OTHER INFORMATION: human interleukin-15 isoform 2 preproprotein
<300> PUBLICATION INFORMATION:
<308> DATABASE ACCESSION NUMBER: NP_751915.1
<309> DATABASE ENTRY DATE: 2017-04-30
<313> RELEVANT RESIDUES IN SEQ ID NO: (1)..(135)

<400> SEQUENCE: 2

Met Val Leu Gly Thr Ile Asp Leu Cys Ser Cys Phe Ser Ala Gly Leu
1               5                   10                  15

Pro Lys Thr Glu Ala Asn Trp Val Asn Val Ile Ser Asp Leu Lys Lys
            20                  25                  30

Ile Glu Asp Leu Ile Gln Ser Met His Ile Asp Ala Thr Leu Tyr Thr
            35                  40                  45

Glu Ser Asp Val His Pro Ser Cys Lys Val Thr Ala Met Lys Cys Phe
50                  55                  60

Leu Leu Glu Leu Gln Val Ile Ser Leu Glu Ser Gly Asp Ala Ser Ile
65                  70                  75                  80

His Asp Thr Val Glu Asn Leu Ile Ile Leu Ala Asn Asn Ser Leu Ser
            85                  90                  95

Ser Asn Gly Asn Val Thr Glu Ser Gly Cys Lys Glu Cys Glu Glu Leu
            100                 105                 110

Glu Glu Lys Asn Ile Lys Glu Phe Leu Gln Ser Phe Val His Ile Val
            115                 120                 125

Gln Met Phe Ile Asn Thr Ser
            130                 135

<210> SEQ ID NO 3
<211> LENGTH: 114
<212> TYPE: PRT
<213> ORGANISM: homo sapiens
<220> FEATURE:
<223> OTHER INFORMATION: mature form of human interleukin-15
```

<400> SEQUENCE: 3

```
Asn Trp Val Asn Val Ile Ser Asp Leu Lys Lys Ile Glu Asp Leu Ile
1               5                  10                  15

Gln Ser Met His Ile Asp Ala Thr Leu Tyr Thr Glu Ser Asp Val His
                20                  25                  30

Pro Ser Cys Lys Val Thr Ala Met Lys Cys Phe Leu Leu Glu Leu Gln
            35                  40                  45

Val Ile Ser Leu Glu Ser Gly Asp Ala Ser Ile His Asp Thr Val Glu
        50                  55                  60

Asn Leu Ile Ile Leu Ala Asn Asn Ser Leu Ser Ser Asn Gly Asn Val
65                  70                  75                  80

Thr Glu Ser Gly Cys Lys Glu Cys Glu Glu Leu Glu Glu Lys Asn Ile
                85                  90                  95

Lys Glu Phe Leu Gln Ser Phe Val His Ile Val Gln Met Phe Ile Asn
            100                 105                 110

Thr Ser
```

<210> SEQ ID NO 4
<211> LENGTH: 267
<212> TYPE: PRT
<213> ORGANISM: homo sapiens
<220> FEATURE:
<223> OTHER INFORMATION: human interleukin-15 receptor subunit alpha
      isoform 1 precursor
<300> PUBLICATION INFORMATION:
<308> DATABASE ACCESSION NUMBER: NP_002180.1
<309> DATABASE ENTRY DATE: 2017-04-30
<313> RELEVANT RESIDUES IN SEQ ID NO: (1)..(267)

<400> SEQUENCE: 4

```
Met Ala Pro Arg Arg Ala Arg Gly Cys Arg Thr Leu Gly Leu Pro Ala
1               5                  10                  15

Leu Leu Leu Leu Leu Leu Leu Arg Pro Pro Ala Thr Arg Gly Ile Thr
                20                  25                  30

Cys Pro Pro Pro Met Ser Val Glu His Ala Asp Ile Trp Val Lys Ser
            35                  40                  45

Tyr Ser Leu Tyr Ser Arg Glu Arg Tyr Ile Cys Asn Ser Gly Phe Lys
        50                  55                  60

Arg Lys Ala Gly Thr Ser Ser Leu Thr Glu Cys Val Leu Asn Lys Ala
65                  70                  75                  80

Thr Asn Val Ala His Trp Thr Thr Pro Ser Leu Lys Cys Ile Arg Asp
                85                  90                  95

Pro Ala Leu Val His Gln Arg Pro Ala Pro Pro Ser Thr Val Thr Thr
            100                 105                 110

Ala Gly Val Thr Pro Gln Pro Glu Ser Leu Ser Pro Ser Gly Lys Glu
        115                 120                 125

Pro Ala Ala Ser Ser Pro Ser Ser Asn Asn Thr Ala Ala Thr Thr Ala
130                 135                 140

Ala Ile Val Pro Gly Ser Gln Leu Met Pro Ser Lys Ser Pro Ser Thr
145                 150                 155                 160

Gly Thr Thr Glu Ile Ser Ser His Glu Ser Ser His Gly Thr Pro Ser
                165                 170                 175

Gln Thr Thr Ala Lys Asn Trp Glu Leu Thr Ala Ser Ala Ser His Gln
            180                 185                 190

Pro Pro Gly Val Tyr Pro Gln Gly His Ser Asp Thr Thr Val Ala Ile
        195                 200                 205
```

```
Ser Thr Ser Thr Val Leu Leu Cys Gly Leu Ser Ala Val Ser Leu Leu
    210                 215                 220

Ala Cys Tyr Leu Lys Ser Arg Gln Thr Pro Pro Leu Ala Ser Val Glu
225                 230                 235                 240

Met Glu Ala Met Glu Ala Leu Pro Val Thr Trp Gly Thr Ser Ser Arg
                245                 250                 255

Asp Glu Asp Leu Glu Asn Cys Ser His His Leu
                260                 265
```

```
<210> SEQ ID NO 5
<211> LENGTH: 234
<212> TYPE: PRT
<213> ORGANISM: homo sapiens
<220> FEATURE:
<223> OTHER INFORMATION: human interleukin-15 receptor subunit alpha
      isoform 2 precursor
<300> PUBLICATION INFORMATION:
<308> DATABASE ACCESSION NUMBER: NP_751950.2
<309> DATABASE ENTRY DATE: 2017-04-30
<313> RELEVANT RESIDUES IN SEQ ID NO: (1)..(234)

<400> SEQUENCE: 5

Met Ala Pro Arg Arg Ala Arg Gly Cys Arg Thr Leu Gly Leu Pro Ala
1               5                   10                  15

Leu Leu Leu Leu Leu Leu Leu Arg Pro Pro Ala Thr Arg Gly Ile Thr
                20                  25                  30

Cys Pro Pro Pro Met Ser Val Glu His Ala Asp Ile Trp Val Lys Ser
            35                  40                  45

Tyr Ser Leu Tyr Ser Arg Glu Arg Tyr Ile Cys Asn Ser Gly Phe Lys
        50                  55                  60

Arg Lys Ala Gly Thr Ser Ser Leu Thr Glu Cys Val Leu Asn Lys Ala
65                  70                  75                  80

Thr Asn Val Ala His Trp Thr Thr Pro Ser Leu Lys Cys Ile Lys Pro
                85                  90                  95

Ala Ala Ser Ser Pro Ser Ser Asn Asn Thr Ala Ala Thr Thr Ala Ala
            100                 105                 110

Ile Val Pro Gly Ser Gln Leu Met Pro Ser Lys Ser Pro Ser Thr Gly
        115                 120                 125

Thr Thr Glu Ile Ser Ser His Glu Ser Ser His Gly Thr Pro Ser Gln
130                 135                 140

Thr Thr Ala Lys Asn Trp Glu Leu Thr Ala Ser Ala Ser His Gln Pro
                145                 150                 155                 160

Pro Gly Val Tyr Pro Gln Gly His Ser Asp Thr Thr Val Ala Ile Ser
            165                 170                 175

Thr Ser Thr Val Leu Leu Cys Gly Leu Ser Ala Val Ser Leu Leu Ala
        180                 185                 190

Cys Tyr Leu Lys Ser Arg Gln Thr Pro Pro Leu Ala Ser Val Glu Met
    195                 200                 205

Glu Ala Met Glu Ala Leu Pro Val Thr Trp Gly Thr Ser Ser Arg Asp
210                 215                 220

Glu Asp Leu Glu Asn Cys Ser His His Leu
225                 230

<210> SEQ ID NO 6
<211> LENGTH: 231
<212> TYPE: PRT
<213> ORGANISM: homo sapiens
```

```
<220> FEATURE:
<223> OTHER INFORMATION: human interleukin-15 receptor subunit alpha
      isoform 3
<300> PUBLICATION INFORMATION:
<308> DATABASE ACCESSION NUMBER: NP_001230468.1
<309> DATABASE ENTRY DATE: 2017-04-23
<313> RELEVANT RESIDUES IN SEQ ID NO: (1)..(231)

<400> SEQUENCE: 6

Met Ser Val Glu His Ala Asp Ile Trp Val Lys Ser Tyr Ser Leu Tyr
1               5                   10                  15

Ser Arg Glu Arg Tyr Ile Cys Asn Ser Gly Phe Lys Arg Lys Ala Gly
            20                  25                  30

Thr Ser Ser Leu Thr Glu Cys Val Leu Asn Lys Ala Thr Asn Val Ala
        35                  40                  45

His Trp Thr Thr Pro Ser Leu Lys Cys Ile Arg Asp Pro Ala Leu Val
    50                  55                  60

His Gln Arg Pro Ala Pro Pro Ser Thr Val Thr Thr Ala Gly Val Thr
65                  70                  75                  80

Pro Gln Pro Glu Ser Leu Ser Pro Ser Gly Lys Glu Pro Ala Ala Ser
                85                  90                  95

Ser Pro Ser Ser Asn Asn Thr Ala Ala Thr Thr Ala Ala Ile Val Pro
            100                 105                 110

Gly Ser Gln Leu Met Pro Ser Lys Ser Pro Ser Thr Gly Thr Thr Glu
        115                 120                 125

Ile Ser Ser His Glu Ser Ser His Gly Thr Pro Ser Gln Thr Thr Ala
    130                 135                 140

Lys Asn Trp Glu Leu Thr Ala Ser Ala Ser His Gln Pro Pro Gly Val
145                 150                 155                 160

Tyr Pro Gln Gly His Ser Asp Thr Thr Val Ala Ile Ser Thr Ser Thr
                165                 170                 175

Val Leu Leu Cys Gly Leu Ser Ala Val Ser Leu Leu Ala Cys Tyr Leu
            180                 185                 190

Lys Ser Arg Gln Thr Pro Pro Leu Ala Ser Val Glu Met Glu Ala Met
        195                 200                 205

Glu Ala Leu Pro Val Thr Trp Gly Thr Ser Ser Arg Asp Glu Asp Leu
    210                 215                 220

Glu Asn Cys Ser His His Leu
225                 230

<210> SEQ ID NO 7
<211> LENGTH: 353
<212> TYPE: PRT
<213> ORGANISM: homo sapiens
<220> FEATURE:
<223> OTHER INFORMATION: human interleukin-15 receptor subunit alpha
      isoform 4
<300> PUBLICATION INFORMATION:
<308> DATABASE ACCESSION NUMBER: NP_001243694.1
<309> DATABASE ENTRY DATE: 2017-04-23
<313> RELEVANT RESIDUES IN SEQ ID NO: (1)..(353)

<400> SEQUENCE: 7

Met Arg Leu Ala Gly Arg Gln Val Pro Glu Gln Arg Ser Pro Pro Pro
1               5                   10                  15

Pro Gly Leu Gly Ser Ala Arg Pro Gly Ser Pro Ala Val Ser Cys Gly
            20                  25                  30

Ala Ala Ala Met Ala Pro Arg Arg Ala Arg Gly Cys Arg Thr Leu Gly
        35                  40                  45
```

-continued

| | | | | | | | | | | | | | | |
|---|---|---|---|---|---|---|---|---|---|---|---|---|---|---|
| Leu | Pro 50 | Ala | Leu | Leu | Leu 55 | Leu | Leu | Leu | Arg | Pro 60 | Ala | Thr | Arg | |
| Asp 65 | Ala | Arg | Asp | Arg 70 | Leu | Ala | Val | Leu | Ala | Gly 75 | Arg | Ser | Arg | Ile | Ser 80 |
| Glu | Ser | Phe | Asn | His 85 | Glu | Val | Gln | Thr | His 90 | Glu | Ala | Cys | Val | Arg 95 | Leu |
| Arg | Thr | Met | Glu 100 | Asn | Cys | Pro | Gln | Cys 105 | His | His | Arg | Thr 110 | Ser | Arg |
| Gln | Gln | Ala 115 | Gly | Ile | Thr | Cys | Pro 120 | Pro | Met | Ser | Val 125 | Glu | His | Ala |
| Asp | Ile | Trp 130 | Val | Lys | Ser | Tyr | Ser 135 | Leu | Tyr | Ser | Arg 140 | Glu | Arg | Tyr | Ile |
| Cys 145 | Asn | Ser | Gly | Phe | Lys 150 | Arg | Lys | Ala | Gly | Thr 155 | Ser | Ser | Leu | Thr | Glu 160 |
| Cys | Val | Leu | Asn | Lys 165 | Ala | Thr | Asn | Val | Ala 170 | His | Trp | Thr | Thr | Pro 175 | Ser |
| Leu | Lys | Cys | Ile 180 | Arg | Asp | Pro | Ala | Leu 185 | Val | His | Gln | Arg | Pro 190 | Ala | Pro |
| Pro | Ser | Thr 195 | Val | Thr | Thr | Ala | Gly 200 | Val | Thr | Pro | Gln | Pro 205 | Glu | Ser | Leu |
| Ser | Pro 210 | Ser | Gly | Lys | Glu | Pro 215 | Ala | Ala | Ser | Ser | Pro 220 | Ser | Ser | Asn | Asn |
| Thr 225 | Ala | Ala | Thr | Thr | Ala 230 | Ala | Ile | Val | Pro | Gly 235 | Ser | Gln | Leu | Met | Pro 240 |
| Ser | Lys | Ser | Pro | Ser 245 | Thr | Gly | Thr | Thr | Glu 250 | Ile | Ser | Ser | His | Glu 255 | Ser |
| Ser | His | Gly | Thr 260 | Pro | Ser | Gln | Thr | Thr 265 | Ala | Lys | Asn | Trp | Glu 270 | Leu | Thr |
| Ala | Ser | Ala 275 | Ser | His | Gln | Pro 280 | Pro | Gly | Val | Tyr | Pro 285 | Gln | Gly | His | Ser |
| Asp | Thr 290 | Thr | Val | Ala | Ile | Ser 295 | Thr | Ser | Thr | Val | Leu 300 | Leu | Cys | Gly | Leu |
| Ser 305 | Ala | Val | Ser | Leu | Leu 310 | Ala | Cys | Tyr | Leu | Lys 315 | Ser | Arg | Gln | Thr | Pro 320 |
| Pro | Leu | Ala | Ser | Val 325 | Glu | Met | Glu | Ala | Met 330 | Glu | Ala | Leu | Pro | Val 335 | Thr |
| Trp | Gly | Thr | Ser 340 | Ser | Arg | Asp | Glu | Asp 345 | Leu | Glu | Asn | Cys | Ser 350 | His | His |
| Leu | | | | | | | | | | | | | | | |

USE OF THE IL-15/IL-15Rα COMPLEX IN THE GENERATION OF ANTIGEN-SPECIFIC T CELLS FOR ADOPTIVE IMMUNOTHERAPY

CROSS-REFERENCE TO RELATED APPLICATIONS

This application is a national stage of International Patent Application No. PCT/US2017/034364, filed May 25, 2017.

REFERENCE TO SEQUENCE LISTING SUBMITTED ELECTRONICALLY

This application incorporates by reference a Sequence Listing submitted with this application as a text file entitled "14259-032-228_Sequence_Listing" created on May 17, 2017 and having a size of 14.2 kilobytes.

1. FIELD

Provided herein are methods of generating antigen-specific T cells for therapeutic administration to a human patient having or suspected of having a pathogen or cancer, utilizing soluble Interleukin 15 (IL-15)/Interleukin 15 Receptor Subunit Alpha (IL-15Rα) complexes ex vivo, in cell culture during ex vivo sensitizing of T cells to the antigen or during ex vivo culturing of antigen-specific T cells. Also disclosed are antigen-specific T cells generated by such methods, and methods of treating a human patient using such antigen-specific T cells. Cell culture systems comprising human T cells, antigen-presenting cells, and soluble IL-15/IL-15Rα complexes are also provided.

2. BACKGROUND

The clinical success of adoptive immunotherapy has been hampered due to the limited persistence of infused self tumor antigen-specific (Huang et al., 2005, J Immunother 28:258-267) or virus antigen-specific T cells (Walter et al., 1995, N Engl J Med 333:1038-1044) leading to recurrence of cancer or infection. Central memory T cells ($T_{CM}$ cells) expressing high levels of L-selectin (CD62L), CCR7 and CD44 can home to and persist within lymphoid tissues, and therefore represent a desirable T cell population for adoptive immunotherapy that have the potential to provide durable protection from disease by virtue of their prolonged in vivo survival (Wherry et al., 2003, Nat Immunol 4:225-234). In both animal models and humans, adoptively transferred $T_{CM}$ phenotype T cells directed against viral antigens such as CMV have demonstrated prolonged in vivo persistence and durable protection from infection (Quinn et al., 2015, J Immunol 194:1726-1736; Berger et al., 2008, J Clin Invest 118:294-305; Stemberger et al., 2014, Blood 124:628-637). Common gamma chain cytokines, in particular IL-7 and IL-15, can potentiate memory T cell survival and proliferation respectively (Schluns and Lefrancois, 2003, Nat Rev Immunol 3:269-279). Accordingly, cytokine cocktails incorporating IL-7 and/or IL-15 have been evaluated for their effect on supporting the in vitro expansion of memory phenotype antigen-specific T cells for adoptive immunotherapy applications (Gerdemann et al., 2012, Mol Ther 20:1622-1632; Wolfl et al., 2011, Cancer Immunol Immunother 60:173-186).

Interleukin-15 has been shown to be critical for the homeostatic proliferation of CD8+ memory T cells (Zhang et al., 1998, Immunity 8:591-599; Sprent and Surh, 2001, Curr Opin Immunol 13:248-254) and it also functionally stimulates both memory T and NK cells (Kennedy et al., 2000, J Exp Med 191:771-780; Schluns et al., 2002, J Immunol 168:4827-4831). In animal models, IL-15 treatment delivered by NK cells (Imamura et al., 2014, Blood 124:1081-1088), intravenously (Roychowdhury et al., 2004, Cancer Res 64:8062-8067; Perna et al., 2013, Clin Cancer Res 19:106-117), or via transduced tumor cells (Liu et al., 2013, Proc Natl Acad Sci USA 110:8158-8163), induced significant tumor regressions shown to be mediated by host derived or adoptively transferred CD8+ T cells and NK cells. Recent in vitro and animal model studies indicate that IL-15 is most potent in stimulating CD8+ memory T cell and NK cell proliferation when it is exclusively bound with IL-15Rα forming an IL-15Rα/IL-15 complex (Dubois et al., 2002, Immunity 17:537-547; Chertova et al., 2013, J Biol Chem 288:18093-18103) (see also Kokaji et al., 2008, J Immunol 180:4391-4401). Such IL-15Rα/IL-15 complexes when infused into tumor bearing animals have been shown to induce significant tumor regressions that are mediated by the sustained proliferation of memory CD8+ T cells (Sato et al., 2007, Proc Natl Acad Sci USA 104:588-593; Stoklasek et al., 2006, J Immunol 177:6072-6080; Xu et al., 2013, Cancer Res 73:3075-3086; Epardaud et al., 2008, Cancer Res 68:2972-2983).

It is now recognized that both secreted and cell surface expressed forms of IL-15 exist in complex with IL-15Rα (Bergamaschi et al., 2008, J *Biol* Chem 283:4189-4199). These IL-15Rα/IL-15 complexes can function in both cis and trans configurations and stimulate responding T and NK cells (Rowley et al., 2009, Eur J Immunol 39:491-506; Burkett et al., 2004, J Exp Med 200:825-834). However, it remains unclear if the secreted IL-15Rα/IL-15 differs from membrane bound IL-15Rα/IL-15 in its functional effects on lymphocyte responses when exposed to antigen (Mortier et al., 2008, J Exp Med 205:1213-1225).

Citation of a reference herein shall not be construed as an admission that such is prior art to the present disclosure.

3. SUMMARY OF THE INVENTION

In one aspect, provided herein are methods of generating a population of cells comprising antigen-specific T cells for therapeutic administration to a human patient having or suspected of having a pathogen or cancer, comprising ex vivo sensitizing human T cells to one or more antigens of the pathogen or cancer, said ex vivo sensitizing comprising co-culturing, over a period of time in culture, a population of human blood cells comprising the human T cells with antigen presenting cells presenting the one or more antigens, in the presence of soluble IL-15/IL-15Rα complexes while in the absence of cells recombinantly expressing soluble IL-15/IL-15Rα complexes.

In various embodiments, the ex vivo sensitizing further comprises adding soluble IL-15/IL-15Rα complexes to the culture. In a preferred embodiment, the adding soluble IL-15/IL-15Rα complexes is such that the concentration of IL-15 in culture supernatant is $10^2$ to $10^3$ pg/ml upon said adding. In a preferred embodiment, adding soluble IL-15/IL-15Rα complexes to the culture is done at the initiation of the co-culturing and every 7 to 10 days thereafter during the co-culturing.

In specific embodiments, the ex vivo sensitizing further comprises adding antigen presenting cells presenting the one or more antigens to the culture at the initiation of said co-culturing and every 7 to 10 days thereafter during the co-culturing. In a specific embodiment, adding soluble IL-15/IL-15Rα complexes to the culture is done at the time of adding antigen presenting cells to the culture.

In specific embodiments, the aforementioned period of time in culture (termed herein "the Sensitization Culture Time;" i.e., the culture time period over which co-culturing occurs) is at least 21 days. In a specific embodiment, the Sensitization Culture Time is in the range of 21-28 days. In a preferred embodiment, the Sensitization Culture Time is 28 days.

In specific embodiments, the antigen presenting cells used in the ex vivo sensitizing step are dendritic cells, cytokine-activated monocytes, peripheral blood mononuclear cells (PBMCs), Epstein-Barr virus-transformed B-lymphoblastoid cell line cells (EBV-BLCL cells), or artificial antigen presenting cells (AAPCs). In a specific embodiment, the antigen presenting cells are AAPCs.

In some embodiments, the antigen presenting cells are loaded with one or more immunogenic peptides or proteins derived from the one or more antigens. In other embodiments, the antigen presenting cells are genetically engineered to recombinantly express one or more immunogenic peptides or proteins derived from the one or more antigens.

In some embodiments, the one or more immunogenic peptides or proteins are a pool of overlapping peptides derived from the one or more antigens. In specific embodiments, the pool of overlapping peptides is a pool of overlapping pentadecapeptides. In other embodiments, the one or more immunogenic peptides or proteins are one or more proteins derived from the one or more antigens.

In another aspect, provided herein are methods of generating a population of cells comprising antigen-specific T cells for therapeutic administration to a human patient having or suspected of having a pathogen or cancer, comprising ex vivo culturing a population of human blood cells comprising human antigen-specific T cells over a period of time in culture in the presence of soluble IL-15/IL-15Rα complexes while in the absence of cells recombinantly expressing soluble IL-15/IL-15Rα complexes, wherein the human antigen-specific T cells are specific to one or more antigens of the pathogen or cancer.

In various embodiments, the method of generating a population of cells comprising antigen-specific T cells further comprises adding soluble IL-15/IL-15Rα complexes to the culture. In a preferred embodiment, the adding soluble IL-15/IL-15Rα complexes is such that the concentration of IL-15 in culture supernatant is $10^2$ to $10^3$ pg/ml upon said adding. In a preferred embodiment, adding soluble IL-15/IL-15Rα complexes to the culture is done at the initiation of the ex vivo culturing and every 7 to 10 days thereafter during the ex vivo culturing.

In specific embodiments, the aforementioned period of time in culture (termed herein "the Sensitization Culture Time;" i.e., the culture time period over which ex vivo culturing occurs) is at least 21 days. In a specific embodiment, the Sensitization Culture Time is in the range of 21-28 days. In a preferred embodiment, the Sensitization Culture Time is 28 days.

In some embodiments, the human antigen-specific T cells recombinantly express one or more chimeric antigen receptors (CARs) recognizing the one or more antigens.

In some embodiments, the human antigen-specific T cells recombinantly express one or more T cell receptors (TCRs) recognizing the one or more antigens.

In preferred embodiments of the preceding aspects and embodiments, the population of human blood cells is derived from a human donor that is seropositive for the one or more antigens.

In certain embodiments, the method of generating a population of cells comprising antigen-specific T cells described herein further comprises a step of deriving the population of human blood cells from a human peripheral blood mononuclear cell (PBMC) sample.

In a specific embodiment, the population of human blood cells used in accordance with the methods of generating a population of cells comprising antigen-specific T cells described herein contains, at initiation of culture, at least 90% $T_{CM}$ cells. In a specific embodiment, the population of human blood cells used in accordance with the methods of generating a population of cells comprising antigen-specific T cells described herein contains, at initiation of culture, at least 95% $T_{CM}$ cells. In a specific embodiment, the population of human blood cells used in accordance with the methods of generating a population of cells comprising antigen-specific T cells described herein contains, at initiation of culture, at least 99% $T_{CM}$ cells. In a specific embodiment, the population of human blood cells used in accordance with the methods of generating a population of cells comprising antigen-specific T cells described herein contains, at initiation of culture, 100% $T_{CM}$ cells. In specific embodiments when the method of generating a population of cells comprising antigen-specific T cells described herein further comprises a step of deriving the population of human blood cells from a human PBMC sample, the deriving step comprises enriching for $T_{CM}$ cells from the human PBMC sample. In a particular embodiment, the enriching step comprises sorting $T_{CM}$ cells from the human PBMC sample by fluorescence-activated cell sorting (FACS).

In specific embodiments, the population of cells comprising antigen-specific T cells described herein lacks substantial cytotoxicity in vitro toward antigen presenting cells that do not present the one or more antigens.

In some embodiments, the one or more antigens is one or more antigens of a pathogen. The pathogen can be a virus, bacterium, fungus, helminth or protist.

In specific embodiments, the pathogen is a virus. In a specific embodiment, the virus is cytomegalovirus (CMV). In another specific embodiment, the virus is Epstein-Barr virus (EBV). In another specific embodiment, the virus is BK virus (BKV), John Cunningham virus (JCV), herpesvirus (such as human herpesvirus-6 or human herpesvirus-8), human papillomavirus (HPV), hepatitis B virus (HBV), hepatitis C virus (HCV), herpes simplex virus (HSV), varicella zoster virus (VZV), Merkel cell polyomavirus (MCV), adenovirus (ADV), human immunodeficiency virus (HIV), influenza virus, ebola virus, poxvirus, rhabdovirus, or paramyxovirus.

In other embodiments, the one or more antigens is one or more antigens of a cancer.

The cancer can be a blood cancer. The cancer can also be a solid tumor cancer, including, but is not limited to, a sarcoma, a carcinoma, a lymphoma, a germ cell tumor, or a blastoma. The solid tumor cancer that can be, such as, but is not limited to: a cancer of the breast, lung, ovary, stomach, pancreas, larynx, esophagus, testes, liver, parotid, biliary tract, colon, rectum, cervix, uterus, endometrium, kidney, bladder, prostate, thyroid, brain, or skin.

In certain embodiments, the one or more antigens is Wilms Tumor 1 (WT1). In a specific aspect of the certain embodiments, the cancer is multiple myeloma or plasma cell leukemia.

In another aspect, provided herein are cell culture systems comprising: (a) a population of human blood cells comprising human T cells; (b) antigen presenting cells presenting one or more antigens of a human pathogen or human cancer;

and (c) soluble IL-15/IL-15Rα complexes; said cell culture system lacking cells recombinantly expressing soluble IL-15/IL-15Rα complexes.

In another aspect, provided herein are cell culture systems comprising: (a) a population of human blood cells comprising human antigen-specific T cells; (b) antigen presenting cells presenting one or more antigens of a human pathogen or human cancer; and (c) soluble IL-15/IL-15Rα complexes; said cell culture system lacking cells recombinantly expressing soluble IL-15/IL-15Rα complexes.

4. BRIEF DESCRIPTION OF FIGURES

FIG. 1. Expression of Transduced IL-15Rα and IL-15 Genes. A2-AAPC transduced to express IL-15Rα alone and A2-AAPC or Baf-3 cells transduced to co-express IL-15Rα and IL-15, were evaluated for the protein level expression of the transduced genes by FACS. As shown (L-R) high expression of the transduced genes was observed in all cell lines.

FIG. 2. Soluble IL-15 Augments Expansion of CMV-CTLs In Vitro and Prevents T Cell Apoptosis. T cells from parallel co-cultures of A2-AAPC supplemented with either sIL-2, sIL-15 or sIL-7+sIL-4 were incubated with anti-CD3 FITC, anti-CD8 PerCP (BD Bioscience, San Jose, CA) and APC conjugated MHC-peptide tetrameric complex (20 minutes at 4° C.). Data were acquired by FACS (LSR-II flow cytometer, BD Biosciences, San Jose, CA, USA) and analyzed using flowjo software (Tree Star Inc, Ashland, OR). $CD3^+$, $CD8^+$ gated T cells were analyzed for percentage of $CD8^+$ $Tet^+$ T cells binding the A2-NLV tetramer in each culture. (A) $CD8^+$ $Tet^+$ T cells at day 7 (upper panel), 21 and 28 (lower panel). (B) The total yield of $Tet^+$ T cells was calculated from the percentages of $CD8^+$ $Tet^+$ T cells within the total $CD3^+$ T cells. The number of $Tet^+$ T cells present at 7, 14, 21 and 28 days is plotted. (C) The total yield of $Tet^+$ T cells at day 28 is plotted for each donor in each cytokine condition to determine differences in total yields of $Tet^+$ T cells between sIL-2 and sIL-15 ($p<0.01$). (D, E) The proportion of apoptotic T cells within A2-AAPC sensitized T cells supplemented with either sIL-2, sIL-15, sIL-2+sIL-15 or sIL-7+sIL-4 were analyzed using FACS after labeling with 7AAD. Analysis was performed 3 days after each A2-AAPC re-stimulation, and 2 days after cytokine supplementation to avoid including cell death resulting from depletion of alloreactive cells after re-stimulation or from activation-induced cell death (AICD). (D) $CD8^+7AAD^+$ T cells are shown in a representative donor, and (E) among all donors tested.

FIG. 3. AAPC Genetically Modified to Co-express IL-15Rα and IL-15 Secrete IL-15 and are Potent Stimulators of Antigen-Specific T Cell Expansion. (A) Baf 3 cells not expressing IL-15Rα (top panel) were sorted and then transduced with the IL-15 gene alone. IL-15 expressing Baf-3 cells were cloned by limiting dilution, and individual clones were then analyzed for intracellular expression of IL-15 protein by FACS after 2, 5 and 7 passages (lower panel). The IL-15 expression within Baf-3 cells expressing IL-15 alone was compared to Baf-3 cells co-expressing IL-15Rα and IL-15. (B) The cell culture supernatants from A2-$AAPC^{IL-15R\alpha}$ and A2-AAPC co-incubated with sIL-15 (10-50 ng/ml) were analyzed for IL-15 in an ELISA assay 10-30 mins after IL-15 supplementation. Parallel analysis was performed for A2-$AAPC^{15R\alpha/15}$ and Baf-$3^{15R\alpha/15}$ containing $10^6$ cells/ml. (C) Parallel in vitro T cell cultures stimulated with A2-AAPC and A2-$AAPC^{IL-15R\alpha}$ supplemented with either soluble IL-2 or IL-15 were established. Total yield of $Tet^+$ T cells (analyzed by FACS) at 7, 14, 21 and 28 days (left) is shown (Error bars=SEM). The scatter graph (right) shows the overall yields of $Tet^+$ T cells at 28 days after culture initiation for each of the 6 donors tested. The horizontal line=median. sIL-15 supplemented T cells stimulated with A2-AAPC or A2-$AAPC^{IL-15R\alpha}$ generated similar yields of $Tet^+$ T cells ($p=0.7$), while sIL-2 supplemented CTLs elicited significantly lower yields of $Tet^+$ T cells ($p<0.01$).

FIG. 4. IL-15 Detected in the Supernatants of A2-$AAPC^{15R\alpha/15}$, Baf-$3^{15R\alpha/15}$ and A2-$AAPC^{IL-15\ R\alpha}$ is Predominantly Bound to IL-15Rα. Concentrated supernatant samples were analyzed by Western blot under non-reducing non-heat denaturing (no dithiothreitol (DTT), 100 minutes at room temperature); reducing, heat denaturing conditions (50 mM DTT, 10 minutes at 95° C. or 98° C.); non-reducing, heat-denaturing conditions (no DTT, 10 minutes at 95° C.). (A) Representative Western blots of Baf-$3^{15R\alpha/15}$ supernatants are shown. Baf-$3^{15R\alpha/15}$ cells were first incubated in serum-free RPMI for 48 hours, then 20 µl of concentrated supernatant was subjected to 12.5% SD S-PAGE under: (I), Non-reducing, non-heat denaturing conditions; (II), reducing, heat-denaturing; (III), non-reducing, heat denaturing conditions. 15Rα/15 complex and IL-15Rα were detected using antibody against IL-15Rα (left panels) and against IL-15 (right panels). (B) Baf-$3^{15R\alpha/15}$ cells were incubated in serum-free RPMI for 24 hours, filtered and concentrated. Serum free (RPMI 1640, Life Technologies, Grand Island, NY, USA) cell supernatants were concentrated 14 to 20-fold using 3 kDa filtration units (Millipore Corporation, Billerica, MA). One ml fractions of the supernatants were obtained a classic FPLC system. Recombinant human soluble IL-15 (10 ng/ml) (R & D Systems) in RPMI was prepared in parallel. Conditioned media (Baf-$3^{15R\alpha/15}$ supernatants and sIL-15 10 ng/ml) was run through the FPLC system using BSA (MW 66 kDa) and Lysozyme (MW 14 kDa) as MW markers. IL-15 was detected in each fraction by ELISA. FPLC fractions (volumes 8-30 ml; ranging from retention volumes below BSA and above Lysozyme) were analyzed for IL-15. As shown, all IL-15 activity in Baf-$3^{15R\alpha/15}$ supernatants was detected in fractions containing molecules greater than 66 kDa MW (BSA). Medium containing recombinant human sIL-15 was detected in fractions comparable to MW of lysozyme (14 kDa). (C) Concentrated supernatants from A2-$AAPC^{15R\alpha/15}$ and A2-$AAPC^{IL-15R\alpha}$ or sIL-15 (10 ng/ml) loaded A2-AAPC were run in parallel through the FPLC system using BSA and lysozyme as MW markers, and fractions analyzed for IL-15 by ELISA. In both A2-$AAPC^{15R\alpha/15}$ and sIL-15 loaded A2-$AAPC^{IL-15R\alpha}$, IL-15 was exclusively detected in the high MW fractions>66 kDa (BSA). In contrast, IL-15 detected in sIL-15 loaded A2-AAPC was exclusively in the low MW fractions~16 kDa, similar to the peak for recombinant human IL-15.

FIG. 5. AAPC Co-expressing IL-15Rα and IL-15 Support Continuous Enrichment of Antigen-Specific $CD8^+$ T cells During Prolonged In Vitro Expansion. T cells from HLA A $02:01^+$ and CMV seropositive donors were sensitized in parallel using (A) A2-$AAPC^{15R\alpha/15}$ and A2-AAPC+Baf-$3^{15R\alpha/15}$ with no exogenously supplemented cytokines. $Tet^+$ T cells were quantitated by FACS analysis at 7, 21 and 28 days after incubation with anti-CD3, anti-CD8 and A2-NLV tetrameric complexes at 4° C. for 20 mins (B) The mean total yield of $Tet^+$ T cells calculated after FACS analysis is plotted for each time point (error bars=SEM). For cultures sensitized with either A2-$AAPC^{15R\alpha/15}$ or A2-AAPC+Baf-$3^{15R\alpha/IL-15}$, the yield of $Tet^+$ T cells was 5-6×$10^7$ compared to 1.8-2.3×$10^7$ for T cells sensitized with A2-AAPC or A2-$AAPC^{IL-15R\alpha}$ and supplemented with soluble IL-15

(p<0.01). (C) T cells stimulated for 14 days with A2-AAPC$^{15R\alpha/15}$, A2-AAPC+Baf-3$^{15R\alpha/IL-15}$, or sIL-2, sIL-15 or sIL-7+sIL-4 loaded A2-AAPC were labeled with CFSE, and then further stimulated for 5 days in the same condition: i.e with A2-AAPC$^{15R\alpha/15}$, or A2-AAPC+Baf-3$^{15R\alpha/IL-15}$ or sIL-2, sIL-15 or sIL-7+sIL-4 loaded A2-AAPC. sIL-2 loaded A2-AAPC T cells stimulated with CD3/CD28 beads (1:1) were used as a positive control. T cells in each condition were then stained with CD3 FITC, CD8 PE, and A2-NLV APC tetrameric complexes and analyzed by FACS. CFSE dilution was analyzed within A2-NLV Tet$^+$ T cells as well as Tet$^{Neg}$ CD8$^+$ T cells to compare the proliferative potential of antigen-specific and non-specific CD8$^+$ T cells in each condition. (D) T cells from 3 HLA A2$^+$ donors were co-cultured in 6 transwell plates containing a 3 μm permeable membrane with (i) A2-AAPC supplemented with either sIL-2 or sIL-15 or Baf3$^{15R\alpha/15}$ or A2-AAPC$^{15R\alpha/15}$ separated from T cell co-cultures by the permeable membrane, (ii) A2-AAPC$^{15R\alpha/15}$ co-cultured with T cells in direct contact. The proportion of antigen-specific T cells in each culture condition were quantitated at 7, 14, 21 and 28 days by tetramer analysis and the total yield of tetramer$^+$ T cells, calculated based on the proportion within the total CD3$^+$ T cells is shown.

FIG. 6. 15Rα/15 Stimulation Endorses the Expansion of Central Memory Phenotype Antigen-Specific T cells. T cell memory phenotype was evaluated after 7, 14, 21 and 28 days in culture for each culture condition using CCR7 and CD62L as markers of central memory phenotype ($T_{CM}$). T cells sensitized for 21-28 days under the different culture conditions were labeled with immunofluorescent antibodies: anti CD3 PE, anti-CD8 perCP, anti-CD62L FITC and anti CCR-7 PE-Cy7 and APC labelled A2-NLV tetrameric complexes for 20 mins at 4° C. and analyzed by FACS. CD8$^+$ Tet$^+$ T cells were gated to determine the proportion of antigen-specific T cells expressing CD62L and CCR7. T cells labelled with HLA B 07:02-TPR tetramers and unstained tubes served as controls for CD62L and CCR7. The total yield of CD62L$^+$/CCR7$^+$ Tet$^+$ T cells was calculated based on the proportion of each population within CD3$^+$ T cells. (A) CD62L$^+$/CCR7$^+$ Tet$^+$ T cells at 7, 14, 21 and 28 days is shown for each donor in each culture condition (error bars=SEM). (B) A representative example demonstrating the proportion of CD62L$^+$/CD45RA$^-$ Tet$^+$ T cells detected at 21 days (left panel) and 28 days (right panel) of culture initiation for each culture condition is shown.

FIG. 7. 15Rα/15 Complexes Support the Generation of High Avidity Antigen-Specific T Cells. The proportion of CD8$^+$ IFN γ$^+$ T cells responding to the CMVpp65 epitope NLVPMVATV presented by HLA A 02:01, were quantitated on day 21 for each parallel culture condition (i) A2-AAPC+ sIL-2 (20 U/ml) or sIL-15 (10 ng/ml) or sIL-2+sIL-15, or sIL-7 (10 ng/ml)+sIL-4 (1666 U/ml); (ii) A2-AAPC$^{IL-15R\alpha}$+ sIL-2 or sIL-15; and (iii) A2-AAPC$^{15R\alpha/15}$ or A2-AAPC+ Baf-3$^{IL-15R\alpha/IL-15}$, with no exogenous cytokines. Aliquots of autologous PBMC were loaded (37° C.×3 hrs) with serial dilutions of NLV peptide (10 nM, 10 pM, 0.1 pM), and co-incubated with T cells at a responder: target ratio of 5:1×12 hours in the presence of brefeldin A (BFA). T cells were labelled with immunofluorescent antibodies against CD3, CD4, CD8, fixed and then permeabilized (fix and perm kit, invitrogen) and then incubated with anti-human IFNγ FITC. Data were acquired on a BD LSRII flow cytometer and analyzed using flowjo software. (A) One representative example demonstrating the proportion of IFNγ$^+$ CD8$^+$ T cells in response to 10 nM peptide loaded targets within CD3$^+$ T cells is shown (B) The total yield of IFNγ$^+$ CD8$^+$ T cells generated in response to 10 nM peptide was calculated from the percentage of IFNγ$^+$ CD8$^+$ T cells and plotted for each donor in each culture condition. (C) T cells from 3 separate HLA A2$^+$ donors that were sensitized in 6 well transwell plates according to cytokine conditions providing sIL-2, sIL-15, or 15Rα/15 complexes via the permeable transmembrane. Antigen-specific T cells generating functional cytokines in response to 10 nM NLV peptide were evaluated on day 21 to quantitate the proportion of NLV specific CD8$^+$ IFNγ$^+$ T cells. (D) After 21 days of stimulation, the proportion of IFNγ$^+$ CD8$^+$ T cells elicited upon secondary stimulation with autologous targets loaded with serial dilutions of NLV peptide is shown for each donor in each culture condition (error bars=SEM), and (E) In one representative donor, IFNγ$^+$ CD8$^+$ T cells elicited in response targets loaded with serial peptide dilutions is shown. The proportion IFNγ$^+$ CD8$^+$ T cells in 15Rα/15 stimulated T cells was significantly greater than sIL-2 or sIL-15 cultures at all peptide dilutions (p=0.001). There was a significant reduction in the proportion of IFNγ$^+$ CD8$^+$ T cells at 10 pM versus 0.1 pM peptide concentrations for sIL-15 cultures (p<0.05).

FIG. 8. 15Rα/15 Stimulated Antigen-Specific T Cells Efficiently Lyse Targets at Lower E:T Ratios. T cell cytotoxic capacity was measured in a standard $^{51}$Cr release assay, performed at 21-28 days after culture initiation using peptide loaded autologous BLCL as targets. BLCL not loaded with peptide were used as control. (A) A fixed E:T ratio of 10 T cells to 1 target cell was used and the cytotoxic activity of T cells sensitized in all culture conditions was tested against targets loaded with serial dilutions of the NLV peptide (10 nM, 1 nM, 0.1 nM, 10 pM, and 0.1 pM at 37° C.×3 hours in serum free medium). (B) The cytotoxic activity of T cells was evaluated at decreasing E:T ratios against targets loaded with a fixed concentration (10 nM) of peptide. (C) T cells in all culture conditions were evaluated for expression of intracellular granzyme B upon secondary re-stimulation with NLV peptide loaded autologous PBMC 21-28 days after culture initiation. T cells co-incubated with peptide loaded autologous PBMC were labelled with fluorescently labelled anti-CD3, anti-CD8, anti-CD4, followed by incubation with anti-human granzyme B after cell permeabilization and analyzed by FACS. The proportion of granzyme B positive T cells CD8$^+$ T cells was evaluated. T cells sensitized in the presence of IL-15Rα/IL-15 complexes generated significantly higher proportions of granzyme B$^+$ T cells compared to sensitization in the presence of soluble IL-2 (p=0.05).

5. DETAILED DESCRIPTION

The present invention provides methods of generating antigen-specific T cells for therapeutic administration to a human patient having or suspected of having a pathogen or cancer, utilizing soluble Interleukin 15 (IL-15)/Interleukin 15 Receptor Subunit Alpha (IL-15Rα) complexes ex vivo, in cell culture during ex vivo sensitizing of T cells to the antigen or during ex vivo culturing of antigen-specific T cells. Also disclosed are antigen-specific T cells generated by such methods, and methods of treating a human patient using such antigen-specific T cells. Cell culture systems comprising human T cells, antigen-presenting cells, and soluble IL-15/IL-15Rα complexes are also provided.

According to the present invention, soluble IL-15/IL-15Rα complexes augment the expansion of antigen-specific T cells in vitro.

5.1. Methods of Generating Antigen-Specific T Cells for Adoptive Immunotherapy

5.1.1. Methods Using Ex Vivo Sensitization of Human T Cells

In one aspect, provided herein are methods of generating a population of cells comprising antigen-specific T cells for therapeutic administration to a human patient having or suspected of having a pathogen or cancer, comprising ex vivo sensitizing human T cells to one or more antigens of the pathogen or cancer, said ex vivo sensitizing comprising co-culturing, over a period of time in culture, a population of human blood cells comprising the human T cells with antigen presenting cells presenting the one or more antigens, in the presence of soluble IL-15/IL-15Rα complexes while in the absence of cells recombinantly expressing soluble IL-15/IL-15Rα complexes. In a preferred embodiment, the ex vivo sensitizing results in expansion of antigen-specific T cells that are specific for the one or more antigens. In a specific embodiment, the human T cells that are ex vivo sensitized are not genetically engineered to be specific for the one or more antigens (e.g., by expression of a chimeric antigen receptor (CAR) or T cell receptor (TCR) specific to the one or more antigens).

In various embodiments, the ex vivo sensitizing further comprises adding soluble IL-15/IL-15Rα complexes to the culture. In specific embodiments, the adding soluble IL-15/IL-15Rα complexes is such that the concentration of IL-15 in culture supernatant is 10 to $10^4$ pg/ml upon said adding. In a preferred embodiment, the adding soluble IL-15/IL-15Rα complexes is such that the concentration of IL-15 in culture supernatant is $10^2$ to $10^3$ pg/ml upon said adding. In a specific embodiment, the adding soluble IL-15/IL-15Rα complexes is such that the concentration of IL-15 in culture supernatant is 10 to $10^2$ pg/ml upon said adding. In another specific embodiment, the adding soluble IL-15/IL-15Rα complexes is such that the concentration of IL-15 in culture supernatant is $10^3$ to $10^4$ pg/ml upon said adding. In another specific embodiment, the adding soluble IL-15/IL-15Rα complexes is such that the concentration of IL-15 in culture supernatant is about $10^2$ pg/ml (i.e., $10^2$±20% pg/ml) upon said adding. In another specific embodiment, the adding soluble IL-15/IL-15Rα complexes is such that the concentration of IL-15 in culture supernatant is about $10^3$ pg/ml (i.e., $10^3$±20% pg/ml) upon said adding. In specific embodiments, the adding soluble IL-15/IL-15Rα complexes is such that the concentration of IL-15 in culture supernatant is at least 10 pg/ml upon said adding. In specific embodiments, the adding soluble IL-15/IL-15Rα complexes is such that the concentration of IL-15 in culture supernatant is at least $10^2$ pg/ml upon said adding. In specific embodiments, the adding soluble IL-15/IL-15Rα complexes is such that the concentration of IL-15 in culture supernatant is at least $10^3$ pg/ml upon said adding.

In specific embodiments, adding soluble IL-15/IL-15Rα complexes to the culture is done at the initiation of the co-culturing and every 1 to 14 days thereafter during the co-culturing. In specific embodiments, adding soluble IL-15/IL-15Rα complexes to the culture is done at the initiation of the co-culturing and every 3 to 12 days thereafter during the co-culturing. In specific embodiments, adding soluble IL-15/IL-15Rα complexes to the culture is done at the initiation of the co-culturing and every 5 to 10 days thereafter during the co-culturing. In preferred embodiments, adding soluble IL-15/IL-15Rα complexes to the culture is done at the initiation of the co-culturing and every 7 to 10 days thereafter during the co-culturing. In a specific embodiment, adding soluble IL-15/IL-15Rα complexes to the culture is done at the initiation of the co-culturing and about every 5 days thereafter during the co-culturing. In another specific embodiment, adding soluble IL-15/IL-15Rα complexes to the culture is done at the initiation of the co-culturing and about every 6 days thereafter during the co-culturing. In another specific embodiment, adding soluble IL-15/IL-15Rα complexes to the culture is done at the initiation of the co-culturing and about every 7 days thereafter during the co-culturing. In another specific embodiment, adding soluble IL-15/IL-15Rα complexes to the culture is done at the initiation of the co-culturing and about every 8 days thereafter during the co-culturing. In another specific embodiment, adding soluble IL-15/IL-15Rα complexes to the culture is done at the initiation of the co-culturing and about every 9 days thereafter during the co-culturing. In another specific embodiment, adding soluble IL-15/IL-15Rα complexes to the culture is done at the initiation of the co-culturing and about every 10 days thereafter during the co-culturing.

The soluble IL-15/IL-15Rα complexes can be any heterodimer complexes of (1) an IL-15 subunit that is a full-length wild-type human IL-15, or a fragment, variant, mutant, or derivative thereof that retains the ability to bind to IL-15Rα, and (2) an IL-15Rα subunit that is a fragment, variant, mutant, or derivative of wild-type human IL-15Rα that retains the ability to bind to IL-15 but lacks the ability to be anchored to the cell membrane by itself, wherein the IL-15 subunit and the IL-15Rα subunit are in a 1:1 molar ratio. Non-limiting exemplary soluble IL-15/IL-15Rα complexes that can be used according to the invention described herein are described in Section 6; Tamzalit et al., 2014, Proc Natl Acad Sci USA 111:8565-8570; Chertova et al., 2013, J Biol Chem 288:18093-18103; and Xu et al., 2013, Cancer Res 73:3075-3086. In certain embodiments, the IL-15 subunit is able to bind to the Interleukin 15 Receptor Subunit Beta (IL-15Rβ)/Interleukin 15 Receptor Subunit Gamma (IL-15Rγ) dimeric receptor. In a specific embodiment, the IL-15 subunit is a full-length wild-type human IL-15, such as a protein having the amino acid sequence of MRISKPHLRSISIQCYLCLLLNSHFLTEAGIHVFILGCFSAGLPKTEANWVNVISDLKKIED LIQSMHIDATLYTESDVHPSCKVTAMKCFLLELQVISLESGDASIHDTVENLIILANNSLSS NGNVTESGCKECEELEEKNIKEFLQSFVHIVQMFINTS (SEQ ID NO: 1) (National Center for Biotechnology Information (NCBI) Reference Sequence: NP_000576.1) preferably from which the signal peptide has been cleaved, or MVLGTIDLCSCFSAGLPKTEANWVNVISDLKKIEDLIQSMHIDATLYTESDVHPSCKVTA MKCFLLELQVISLESGDASIHDTVENLIILANNSLSSNGNVTESGCKECEELEEKNIKEFLQ SFVHIVQMFINTS (SEQ ID NO:2) (NCBI Reference Sequence: NP_751915.1) preferably from which the signal peptide has been cleaved, or, preferably, the mature form having the amino acid sequence of NWVNVISDLKKIEDLIQSMHIDATLYTESDVHPSCKVTAMKCFLLELQVISLESGDASIH DTVENLIILANNSLSSNGNVTESGCKECEELEEKNIKEFLQSFVHIVQMFINTS (SEQ ID NO:3) (Grabstein et al., 1994, Science 264:965-968). In another specific embodiment, the IL-15 subunit is a mutant human IL-15 as described in Xu et al., 2013, Cancer Res 73:3075-3086. In another specific embodiment, the IL-15 subunit is a fusion protein, for example, wherein the IL-15 sequence is linked to the Fc portion of a human immunoglobulin, such as the Fc portion of human IgG (e.g., IgG1). In a specific embodiment, the IL-15Rα subunit is a cleaved form of IL-15Rα that is secreted by a cell in which it is expressed, such as the naturally produced cleaved form of IL-15Rα described in Chertova et al., 2013, J Biol Chem 288:18093-18103 or a secreted form of any of the other IL-15Rα isoforms. In a specific embodiment, the IL-15Rα isoform has the amino acid sequence of one of the following sequences from which the signal peptide has been cleaved: MAPRRARGCRTLGLPALLLLLLLRPPATRGITCPPPMSVEHADIWVKSYSLYSRERYICN SGFKRKAGTSSLTECVLNKATNVAHWTTPSLKCIRDPALVHQRPAPPSTVTTAGVTPQPESLSPSGKEPAASSPSSNNTAATTAAIVPGSQLMPSKSPSTGTTEISSHESSHGTPSQTTAK NWELTASASHQPPGVYPQGHSDTTVAISTSTVLLCGLSAVSLLACYLKSRQTPPLASVEMEAMEALPVTWGTSSRDEDLENCSHHL (SEQ ID NO:4) (NCBI Reference Sequence: NP_002180.1), MAPRRARGCRTLGLPALLLLLLLRPPATRGITCPPPMSVEHADIWVKSYSLYSRERYICN SGFKRKAGTSSLTECVLNKATNVAHWTTPSLKCIKPAASSPSSNNTAATTAAIVPGSQL MPSKSPSTGTTEISSHESSHGTPSQTTAKNWELTASASHQPPGVYPQGHSDTTVAISTSTVLLCGLSAVSLLACYLKSRQTPPLASVEMEAMEALPVTWGTSSRDEDLENCSHHL (SEQ ID NO:5) (NCBI Reference Sequence: NP_751950.2), MSVEHADIWVKSYSLYSRERYICNSGFKRKAGTSSLTECVLNKATNVAHWTTPSLKCIRDPALVHQRPAPPSTVTTAGVTPQPESLSPSGKEPAASSPSSNNTAATTAAIVPGSQLMPSKSPSTGTTEISSHESSHGTPSQTTAKNWELTASASHQPPGVYPQGHSDTTVAISTSTVLLCGLSAVSLLACYLKSRQTPPLASVEMEAMEALPVTWGTSSRDEDLENCSHHL (SEQ ID NO:6) (NCBI Reference Sequence: NP_001230468.1), and MRLAGRQVPEQRSPPPPGLGSARPGSPAVSCGAAAMAPRRARGCRTLGLPALLLLLLR PPATRDARDRLAVLAGRSRISESFNHEVQTHEACVRLRTMENCPQCHHHRTSRQQAGIT CPPPMSVEHADIWVKSYSLYSRERYICNSGFKRKAGTSSLTECVLNKATNVAHWTTPSL KCIRDPALVHQRPAPPSTVTTAGVTPQPESLSPSGKEPAASSPSSNNTAATTAAIVPGSQL MPSKSPSTGTTEISSHESSHGTPSQTTAKNWELTASASHQPPGVYPQGHSDTTVAISTSTV LLCGLSAVSLLACYLKSRQTPPLASVEMEAMEALPVTWGTSSRDEDLENCSHHL (SEQ ID NO:7) (NCBI Reference Sequence: NP_001243694.1). In another specific embodiment, the IL-15Rα subunit is a fusion protein, for example, wherein the IL-15Rα sequence is linked to the Fc portion of a human immunoglobulin, such as the Fc portion of human IgG (e.g., IgG1). In a specific embodiment, the IL-15 subunit is a fusion protein, for example, wherein the IL-15 sequence is linked to the Fc portion of a human immunoglobulin, such as the Fc portion of human IgG (e.g., IgG1), and the IL-15Rα subunit is a fusion protein, for example, wherein the IL-15Rα sequence is linked to the Fc portion of a human immunoglobulin, such as the Fc portion of human IgG (e.g., IgG1).

In a specific embodiment, the soluble IL-15/IL-15Rα complexes are produced by cells transduced with vector(s) to co-express within the same cell the IL-15 subunit and the IL-15Rα subunit. In a preferred embodiment, the IL-15 subunit and the IL-15Rα subunit are expressed from two different vectors within the same cell. Preferably, the soluble IL-15/IL-15Rα complexes are secreted by a cell that recombinantly expresses the IL-15 subunit and the IL-15Rα subunit, and can be recovered from cell culture supernatant.

In a specific embodiment, the soluble IL-15/IL-15Rα complexes are produced by adding purified IL-15 subunit to a culture of cells transduced with a vector comprising a nucleotide sequence encoding the IL-15Rα subunit, which cells secrete the encoded IL-15Rα subunit, and recovering the soluble IL-15/IL-15Rα complexes from the cell culture supernatant. The IL-15 subunit can be from a previously purified, cryopreserved preparation or a commercially available product or recovered from cell culture supernatant of cells transduced with a vector comprising a nucleotide sequence encoding the IL-15 subunit, which cells secrete the encoded IL-15 subunit. Since IL-15 is typically transiently expressed when recombinantly expressed in cells in the absence of recombinant co-expression in the same cell of IL-15Rα, in order to avoid the need for repeated transduction of cells for purposes of producing IL-15 alone, obtaining an IL-15 subunit from a cryopreserved preparation or commercially available source is preferred for use in the adding step.

In specific embodiments, the soluble IL-15/IL-15Rα complexes are produced by complexing the IL-15 subunit and the IL-15Rα subunit ex vivo. In a specific embodiment, the IL-15 subunit is a commercially available product or is recovered from cell culture supernatant of cells transduced with a vector comprising a nucleotide sequence encoding the IL-15 subunit, which cells secrete the encoded IL-15 subunit. The IL-15Rα subunit can be a commercially available product or recovered from cell culture supernatant of cells transduced with a vector comprising a nucleotide sequence encoding the IL-15Rα subunit, which cells secrete the encoded IL-15Rα subunit. The IL-15 subunit and the IL-15Rα subunit can be complexed ex vivo by any method known in the art for complexing proteins ex vivo, such as by combining purified IL-15 subunit proteins and purified IL-15Rα subunit proteins ex vivo in a buffered solution (for example, in the presence of bovine serum albumin in phosphate-buffered saline (PBS)) at 37° C. for a period of time (for example, as described in Epardaud et al., 2008, Cancer Res 68:2972-2983).

Any mammalian cell line cells that can be passaged in vitro can be used for producing the soluble IL-15/IL-15Rα complexes, the IL15 subunit and/or the IL-15Rα subunit, such as Ba/F3 cells (i.e., Baf-3 cells), K562 cells, or murine fibroblast NIH 3T3 based artificial antigen presenting cells (AAPCs) (Hasan et al., 2009, J Immunol 183: 2837-2850). The cells can be human, murine, hamster, or other mammalian cells. The soluble IL-15/IL-15Rα complexes, the IL15 subunit and/or the IL-15Rα subunit can be purified from the supernatants from the culture of transduced cells by any method known in the art for purifying proteins, such as by fast protein liquid chromatography (FPLC). Non-limiting exemplary methods of producing the soluble IL-15/IL-15Rα complexes are described in Section 6; Tamzalit et al., 2014, Proc Natl Acad Sci USA 111:8565-8570; Chertova et al., 2013, J Biol Chem 288:18093-18103; and Xu et al., 2013, Cancer Res 73:3075-3086.

In some embodiments, the preparation of soluble IL-15/IL-15Rα complexes produced as described herein is free of cells recombinantly expressing the soluble IL-15/IL-15Rα complexes. In other embodiments, the preparation of soluble IL-15/IL-15Rα complexes produced as described herein contains cells recombinantly expressing the soluble IL-15/IL-15Rα complexes. When the preparation of soluble IL-15/IL-15Rα complexes contains cells recombinantly expressing the soluble IL-15/IL-15Rα complexes, the method of generating a population of cells comprising antigen-specific T cells further comprises, before the step of adding soluble IL-15/IL-15Rα complexes to the culture, a step of removing the cells recombinantly expressing the soluble IL-15/IL-15Rα complexes from the preparation or a step of purifying the soluble IL-15/IL-15Rα complexes from the preparation so as to separate the complexes from the cells recombinantly expressing the soluble IL-15/IL-15Rα complexes. The removing or purifying can be performed by any method known in the art for removing cells from a mixture of cells and proteins or purifying proteins from a mixture of cells and proteins, such as by centrifugation or by use of a filter.

In certain embodiments, the soluble IL-15/IL-15Rα complexes are thawed from a cryopreserved stock before being added to the culture. In a specific embodiment, the method of generating a population of cells comprising antigen-specific T cells further comprises thawing the soluble IL-15/IL-15Rα complexes from a cryopreserved stock before adding them to the culture. In a further specific embodiment, the method of generating a population of cells comprising antigen-specific T cells further comprises cryopreserving soluble IL-15/IL-15Rα complexes and thawing the soluble IL-15/IL-15Rα complexes before adding them to the culture. In a particular embodiment, cryopreserving soluble IL-15/IL-15Rα complexes comprises combining soluble IL-15/IL-15Rα complexes with a cryopreservative, such as dimethyl sulfoxide (DMSO), glycerol, polyvinylpyrrolidine, polyethylene glycol, albumin (such as bovine serum albumin), dextran, sucrose, ethylene glycol, i-erythritol, D-ribitol, D-mannitol, D-sorbitol, i-inositol, D-lactose, choline chloride, amino acids, methanol, acetamide, glycerol monoacetate, inorganic salts, or any cryopreservative known in the art for use in cryopreserving proteins. The concentration of the soluble IL-15/IL-15Rα complexes in the cryopreserved stock can be any concentration suitable for long-term storage of the complexes, such as 10 µg/ml to 10 mg/ml (for example, 10 µg/ml to 0.1 mg/ml, 0.1 mg/ml to 1 mg/ml, or 1 mg/ml to 10 mg/ml). In a specific embodiment, the concentration of the soluble IL-15/IL-15Rα complexes in the cryopreserved stock is about 0.1 mg/ml (i.e., 0.1±20% mg/ml). The cryopreserved soluble IL-15/IL-15Rα complexes can be stored in liquid nitrogen or dry ice for long-term storage, or a fridge (0-8° C.) for short-term storage (such as up to a week or 1-3 days).

In various embodiments, the ex vivo sensitizing further comprises adding antigen presenting cells presenting the one or more antigens to the culture. The antigen presenting cells are typically irradiated cells to prevent multiplication of these cells after being added to the culture. In specific embodiments, the ex vivo sensitizing further comprises adding antigen presenting cells presenting the one or more antigens to the culture at the initiation of said co-culturing and every 1 to 14 days thereafter during the co-culturing. In specific embodiments, the ex vivo sensitizing further comprises adding antigen presenting cells presenting the one or more antigens to the culture at the initiation of said co-culturing and every 3 to 12 days thereafter during the co-culturing. In specific embodiments, the ex vivo sensitizing further comprises adding antigen presenting cells presenting the one or more antigens to the culture at the initiation of said co-culturing and every 5 to 10 days thereafter during the co-culturing. In preferred embodiments, the ex vivo sensitizing further comprises adding antigen presenting cells presenting the one or more antigens to the culture at the initiation of said co-culturing and every 7 to 10 days thereafter during the co-culturing. In a specific embodiment, the ex vivo sensitizing further comprises adding antigen presenting cells presenting the one or more antigens to the culture at the initiation of said co-culturing and about every 5 days thereafter during the co-culturing. In another specific embodiment, the ex vivo sensitizing further comprises adding antigen presenting cells presenting the one or more antigens to the culture at the initiation of said co-culturing and about every 6 days thereafter during the co-culturing. In another specific embodiment, the ex vivo sensitizing further comprises adding antigen presenting cells presenting the one or more antigens to the culture at the initiation of said co-culturing and about every 7 days thereafter during the co-culturing. In another specific embodiment, the ex vivo sensitizing further comprises adding antigen presenting cells presenting the one or more antigens to the culture at the initiation of said co-culturing and about every 8 days thereafter during the co-culturing. In another specific embodiment, the ex vivo sensitizing further comprises adding antigen presenting cells presenting the one or more antigens to the culture at the initiation of said co-culturing and about every 9 days thereafter during the co-culturing. In another specific embodiment, the ex vivo sensitizing further comprises adding antigen presenting cells presenting the one or more antigens to the culture at the initiation of said co-culturing and about every 10 days thereafter during the co-culturing. In specific embodiments, adding soluble IL-15/IL-15Rα complexes to the culture is done at the time of adding antigen presenting cells to the culture (such as, on the same day or preferably in the same hour).

In specific embodiments, the aforementioned period of time in culture (termed herein "the Sensitization Culture Time;" i.e., the culture time period over which co-culturing occurs) is at least 14 days (preferably, at least 21 days). In a specific embodiment, the Sensitization Culture Time is in the range of 21-28 days. In another specific embodiment, the Sensitization Culture Time is 21 days. In another specific embodiment, the Sensitization Culture Time is 22 days. In another specific embodiment, the Sensitization Culture Time is 23 days. In another specific embodiment, the Sensitization Culture Time is 24 days. In another specific embodiment, the Sensitization Culture Time is 25 days. In another specific embodiment, the Sensitization Culture Time is 26 days. In another specific embodiment, the Sensitization Culture Time is 27 days. In a preferred embodiment, the Sensitization Culture Time is 28 days. In specific embodiments, the Sensitization Culture Time is at least 28 days.

The ex vivo sensitizing step can be performed by any method known in the art to stimulate T cells to be antigen-specific ex vivo, such as a method as described in Section 6; Koehne et al., 2000, Blood 96:109-117; Trivedi et al., 2005, Blood 105:2793-2801; Haque et al., 2007, Blood 110:1123-1131; Hasan et al., 2009, J Immunol 183: 2837-2850; Feuchtinger et al., 2010, Blood 116:4360-4367; Doubrovina et al., 2012, Blood 120:1633-1646; Leen et al., 2013, Blood 121:5113-5123; Papadopoulou et al., 2014, Sci Transl Med 6:242ra83; Sukdolak et al., 2013, Biol Blood Marrow Transplant 19:1480-1492; Koehne et al., 2015, Biol Blood Marrow Transplant 21: 1663-1678; International Patent Application Publication No. WO 2016/073550; or International Patent Application Publication No. WO 2017/044678.

The antigen presenting cells used in the ex vivo sensitizing step can be any antigen presenting cells suitable for presenting the one or more antigens, including professional antigen presenting cells and non-professional antigen presenting cells. In specific embodiments, the antigen presenting cells used in the ex vivo sensitizing step are dendritic cells, cytokine-activated monocytes, peripheral blood mononuclear cells (PBMCs), Epstein-Barr virus-transformed B-lymphoblastoid cell line cells (EBV-BLCL cells), or artificial antigen presenting cells (AAPCs). In a specific embodiment, the antigen presenting cells are dendritic cells. In another specific embodiment, the antigen presenting cells are PBMCs. In another specific embodiment, the antigen presenting cells are EBV-BLCL cells. In another specific embodiment, the antigen presenting cells are AAPCs. In some embodiments, the antigen presenting cells are derived from the donor of the population of human blood cells. In other embodiments, the antigen presenting cells are allogeneic to the donor of the population of human blood cells. The antigen presenting cells can be obtained by any method known in the art, such as the method(s) described in Section 6; Koehne et al., 2000, Blood 96:109-117; Koehne et al., 2002, Blood 99:1730-1740; Trivedi et al., 2005, Blood 105:2793-2801; O'Reilly et al., 2007, Immunol Res 38:237-250; Hasan et al., 2009, J Immunol 183: 2837-2850; Barker et al., 2010, Blood 116:5045-5049; O'Reilly et al., 2011, Best Practice & Research Clinical Haematology 24:381-391; Doubrovina et al., 2012, Blood 120:1633-1646; Koehne et al., 2015, Biol Blood Marrow Transplant 21: 1663-1678; International Patent Application Publication No. WO 2016/073550; or International Patent Application Publication No. WO 2017/044678.

In some embodiments, the antigen presenting cells are loaded with one or more immunogenic peptides or proteins derived from the one or more antigens. Non-limiting exemplary methods for loading antigen presenting cells with peptide(s) derived from antigen(s) can be found in Section 6; Trivedi et al., 2005, Blood 105:2793-2801; Barker et al., 2010, Blood 116:5045-5049; Doubrovina et al., 2012, Blood 120:1633-1646; Hasan et al., 2009, J Immunol 183: 2837-2850; Koehne et al., 2015, Biol Blood Marrow Transplant 21: 1663-1678; International Patent Application Publication No. WO 2016/073550; and International Patent Application Publication No. WO 2017/044678. In other embodiments, the antigen presenting cells are genetically engineered to recombinantly express one or more immunogenic peptides or proteins derived from the one or more antigens. Any appropriate method known in the art for introducing nucleic acid vehicles into cells to express proteins, such as transduction or transformation, can be used to genetically engineer the antigen presenting calls to recombinantly express the one or more immunogenic peptides or proteins derived from the one or more antigens.

In some embodiments, the one or more immunogenic peptides or proteins are a pool of overlapping peptides derived from the one or more antigens. In specific embodiments, the pool of overlapping peptides is a pool of overlapping pentadecapeptides. In other embodiments, the one or more immunogenic peptides or proteins are one or more proteins derived from the one or more antigens.

In specific embodiments, the method of generating a population of cells comprising antigen-specific T cells further comprises, after the step of ex vivo sensitizing, a step of cryopreserving the ex vivo sensitized (and preferably expanded) human T cells, or a fraction thereof. In a specific embodiment, the method of generating a population of cells comprising antigen-specific T cells further comprises, after the step of cryopreserving, steps of thawing and optionally expanding in culture the ex vivo sensitized (and preferably expanded) and cryopreserved human T cells or a faction thereof. The cryopreserving and thawing steps can be performed by known methods in the art for cryopreserving T cells and thawing T cells, respectively.

The term "about" shall be construed so as to allow normal variation, such as, for example, a variation within 20%.

5.1.2. Methods Using Human Antigen-Specific T Cells

In another aspect, provided herein are methods of generating a population of cells comprising antigen-specific T cells for therapeutic administration to a human patient having or suspected of having a pathogen or cancer, comprising ex vivo culturing a population of human blood cells comprising human antigen-specific T cells over a period of time in culture in the presence of soluble IL-15/IL-15Rα complexes while in the absence of cells recombinantly expressing soluble IL-15/IL-15Rα complexes, wherein the human antigen-specific T cells are specific to one or more antigens of the pathogen or cancer. In a preferred embodiment, the ex vivo culturing results in expansion of the human antigen-specific T cells.

In some embodiments, the human antigen-specific T cells recombinantly express one or more chimeric antigen receptors (CARs) recognizing the one or more antigens. In a specific embodiment, the method of generating a population of cells comprising antigen-specific T cells further comprises, prior to the ex vivo culturing, transducing a population of T cells with one or more nucleic acids encoding the one or more CARs recognizing the one or more antigens; thereby producing the human antigen-specific T cells.

CARs are engineered receptors that provide both antigen binding and immune cell activation functions (Sadelain et al., 2013, Cancer Discovery 3:388-398). They usually comprise an antigen-binding domain (e.g., derived from a monoclonal antibody or the extracellular domain of a receptor), a transmembrane domain, an intracellular domain, and optionally a co-stimulatory domain. CARs can be used to graft the specificity of an antigen-binding domain onto an immune cell such as a T cell.

The population of T cells transduced with one or more nucleic acids encoding the one or more CARs can be generated by any method known in the art, for example, as described in Stauss et al., 2015, Curr Opin Pharmacol 24:113-118; Sharpe and Mount, 2015, Dis Model Mech 8:337-350; or Park et al., 2011, Trends Biotechnol 29:550-557.

The nucleic acid encoding a CAR can be DNA, RNA, or a nucleic acid analog. In specific embodiments, such a nucleic acid may be part of a vector. In a specific embodiment, the vector is an expression vector that is capable of directing the expression of a nucleic acid encoding a polypeptide of the CAR described herein in T cells. Non-limiting examples of expression vectors suitable for directing the expression of a nucleic acid encoding a polypeptide of the CAR described herein include, but are not limited to, plasmids and viral vectors, such as synthetic vectors, lentiviral vectors, replication-defective retroviral vectors, or autonomously replicating plasmids. In a specific embodiment, an expression vector used for directing the expression of a nucleic acid encoding a polypeptide of the CAR described herein includes one or more regulatory sequences operably linked to the nucleic acid to be expressed. "Operably linked" is intended to mean that a nucleic acid of interest is linked to the regulatory sequence(s) in a manner which allows for expression of the nucleic acid in T cells.

Regulatory sequences include promoters, enhancers and other expression control elements (e.g., polyadenylation signals).

A nucleic acid encoding a polypeptide of the CAR described herein, for example, an expression vector, can be transduced into host cells via conventional transformation or transfection (such as, transfection by a virus, e.g., a retrovirus or lentivirus) techniques. Such techniques include, but are not limited to, calcium phosphate or calcium chloride co-precipitation, DEAE-dextran-mediated transfection, lipofection, and electroporation. Cells containing a nucleic acid encoding a polynucleotide of the CAR described herein may be selected using one or more selectable markers known in the art.

In some embodiments, the human antigen-specific T cells recombinantly express one or more T cell receptors (TCRs) recognizing the one or more antigens. In a specific embodiment, the method of generating a population of cells comprising antigen-specific T cells further comprises, prior to the ex vivo culturing, transducing a population of T cells with one or more nucleic acids encoding the one or more TCRs recognizing the one or more antigens; thereby producing the human antigen-specific T cells.

TCR is a cell surface molecule on T cells that is responsible for recognizing antigen peptide-bound major histocompatibility complex (MHC) molecules.

The population of T cells transduced with one or more nucleic acids encoding the one or more TCRs can be generated by any method known in the art, for example, as described in Stauss et al., 2015, Curr Opin Pharmacol 24:113-118; Sharpe and Mount, 2015, Dis Model Mech 8:337-350; Kunert et al., 2013, Front Immunol 4: 363; Stone et al., 2012, Methods Enzymol 503:189-222; or Park et al., 2011, Trends Biotechnol 29:550-557.

The nucleic acid encoding a TCR can be DNA, RNA, or a nucleic acid analog. In specific embodiments, such a nucleic acid may be part of a vector. In a specific embodiment, the vector is an expression vector that is capable of directing the expression of a nucleic acid encoding a polypeptide of the TCR described herein in T cells. Non-limiting examples of expression vectors suitable for directing the expression of a nucleic acid encoding a polypeptide of the TCR described herein include, but are not limited to, plasmids and viral vectors, such as synthetic vectors, lentiviral vectors, replication-defective retroviral vectors, or autonomously replicating plasmids. In a specific embodiment, an expression vector used for directing the expression of a nucleic acid encoding a polypeptide of the TCR described herein includes one or more regulatory sequences operably linked to the nucleic acid to be expressed. "Operably linked" is intended to mean that a nucleic acid of interest is linked to the regulatory sequence(s) in a manner which allows for expression of the nucleic acid in T cells. Regulatory sequences include promoters, enhancers and other expression control elements (e.g., polyadenylation signals).

A nucleic acid encoding a polypeptide of the TCR described herein, for example, an expression vector, can be transduced into host cells via conventional transformation or transfection (such as, transfection by a virus, e.g., a retrovirus or lentivirus) techniques. Such techniques include, but are not limited to, calcium phosphate or calcium chloride co-precipitation, DEAE-dextran-mediated transfection, lipofection, and electroporation. Cells containing a nucleic acid encoding a polynucleotide of the TCR described herein may be selected using one or more selectable markers known in the art.

In some embodiments, the human antigen-specific T cells are antigen-specific T cells generated by ex vivo sensitization, performed by any method known in the art to stimulate T cells to be antigen-specific ex vivo, such as a method as described in Section 6; Koehne et al., 2000, Blood 96:109-117; Trivedi et al., 2005, Blood 105:2793-2801; Haque et al., 2007, Blood 110:1123-1131; Hasan et al., 2009, J Immunol 183: 2837-2850; Feuchtinger et al., 2010, Blood 116:4360-4367; Doubrovina et al., 2012, Blood 120:1633-1646; Leen et al., 2013, Blood 121:5113-5123; Papadopoulou et al., 2014, Sci Transl Med 6:242ra83; Sukdolak et al., 2013, Biol Blood Marrow Transplant 19:1480-1492; Koehne et al., 2015, Biol Blood Marrow Transplant 21: 1663-1678; International Patent Application Publication No. WO 2016/073550; or International Patent Application Publication No. WO 2017/044678.

In other embodiments, the human antigen-specific T cells are antigen-specific T cells purified from cells (such as peripheral blood mononuclear cells (PBMCs)) derived from a blood sample that is seropositive for the one or more antigens (for example, by sorting (such as fluorescence activated cell sorting) T cells that recognize the one or more antigens from the blood sample cells).

In various embodiments, the method of generating a population of cells comprising antigen-specific T cells further comprises adding soluble IL-15/IL-15Rα complexes to the culture. In specific embodiments, the adding soluble IL-15/IL-15Rα complexes is such that the concentration of IL-15 in culture supernatant is 10 to $10^4$ pg/ml upon said adding. In a preferred embodiment, the adding soluble IL-15/IL-15Rα complexes is such that the concentration of IL-15 in culture supernatant is $10^2$ to $10^3$ pg/ml upon said adding. In a specific embodiment, the adding soluble IL-15/IL-15Rα complexes is such that the concentration of IL-15 in culture supernatant is 10 to $10^2$ pg/ml upon said adding. In another specific embodiment, the adding soluble IL-15/IL-15Rα complexes is such that the concentration of IL-15 in culture supernatant is $10^3$ to $10^4$ pg/ml upon said adding. In another specific embodiment, the adding soluble IL-15/IL-15Rα complexes is such that the concentration of IL-15 in culture supernatant is about $10^2$ pg/ml (i.e., $10^2 \pm 20\%$ pg/ml) upon said adding. In another specific embodiment, the adding soluble IL-15/IL-15Rα complexes is such that the concentration of IL-15 in culture supernatant is about $10^3$ pg/ml (i.e., $10^3 = 20\%$ pg/ml) upon said adding. In specific embodiments, the adding soluble IL-15/IL-15Rα complexes is such that the concentration of IL-15 in culture supernatant is at least 10 pg/ml upon said adding. In specific embodiments, the adding soluble IL-15/IL-15Rα complexes is such that the concentration of IL-15 in culture supernatant is at least $10^2$ pg/ml upon said adding. In specific embodiments, the adding soluble IL-15/IL-15Rα complexes is such that the concentration of IL-15 in culture supernatant is at least $10^3$ pg/ml upon said adding.

In specific embodiments, adding soluble IL-15/IL-15Rα complexes to the culture is done at the initiation of the ex vivo culturing and every 1 to 14 days thereafter during the ex vivo culturing. In specific embodiments, adding soluble IL-15/IL-15Rα complexes to the culture is done at the initiation of the ex vivo culturing and every 3 to 12 days thereafter during the ex vivo culturing. In specific embodiments, adding soluble IL-15/IL-15Rα complexes to the culture is done at the initiation of the ex vivo culturing and every 5 to 10 days thereafter during the ex vivo culturing. In preferred embodiments, adding soluble IL-15/IL-15Rα complexes to the culture is done at the initiation of the ex vivo culturing and every 7 to 10 days thereafter during the ex vivo culturing. In a specific embodiment, adding soluble IL-15/IL-15Rα complexes to the culture is done at the initiation of the ex vivo culturing and about every 5 days thereafter during the ex vivo culturing. In another specific embodiment, adding soluble IL-15/IL-15Rα complexes to the culture is done at the initiation of the ex vivo culturing and about every 6 days thereafter during the ex vivo culturing. In another specific embodiment, adding soluble IL-15/IL-15Rα complexes to the culture is done at the initiation of the ex vivo culturing and about every 7 days thereafter during the ex vivo culturing. In another specific embodiment, adding soluble IL-15/IL-15Rα complexes to the culture is done at the initiation of the ex vivo culturing and about every 8 days thereafter during the ex vivo culturing. In another specific embodiment, adding soluble IL-15/IL-15Rα complexes to the culture is done at the initiation of the ex vivo culturing and about every 9 days thereafter during the ex vivo culturing. In another specific embodiment, adding soluble IL-15/IL-15Rα complexes to the culture is done at the initiation of the ex vivo culturing and about every 10 days thereafter during the ex vivo culturing.

The soluble IL-15/IL-15Rα complexes can be any heterodimer complexes of (1) an IL-15 subunit that is a full-length wild-type human IL-15, or a fragment, variant, mutant, or derivative thereof that retains the ability to bind to IL-15Rα, and (2) an IL-15Rα subunit that is a fragment, variant, mutant, or derivative of wild-type human IL-15Rα that retains the ability to bind to IL-15 but lacks the ability to be anchored to the cell membrane by itself, wherein the IL-15 subunit and the IL-15Rα subunit are in a 1:1 molar ratio. Non-limiting exemplary soluble IL-15/IL-15Rα complexes that can be used according to the invention described herein are described in Section 6; Tamzalit et al., 2014, Proc Natl Acad Sci USA 111:8565-8570; Chertova et al., 2013, J Biol Chem 288:18093-18103; and Xu et al., 2013, Cancer Res 73:3075-3086. In certain embodiments, the IL-15 subunit is able to bind to the Interleukin 15 Receptor Subunit Beta (IL-15Rβ)/Interleukin 15 Receptor Subunit Gamma (IL-15Rγ) dimeric receptor. In a specific embodiment, the IL-15 subunit is a full-length wild-type human IL-15, such as a protein having the amino acid sequence of MRISKPHLRSISIQCYLCLLLNSHFLTEAGIHV-FILGCFSAGLPKTEANWVNVISDLKKIED LIQSMHI-DATLYTESDVHPSCKVTAMKCFLLELQVISLESGDA-SIHDTVENLIILANNSLSS NGNVTESGCKE-CEELEEKNIKEFLQSFVHIVQMFINTS (SEQ ID NO: 1) (NCBI Reference Sequence: NP_000576.1) preferably from which the signal peptide has been cleaved, or MVLGTIDLCSCFSAGLPKTEANWVNVISDLK-KIEDLIQSMHIDATLYTESDVHPSCKVTA MKCFL-LELQVISLESGDASIHDTVENLIILANNSLSSNG-NVTESGCKECEELEEKNIKEFLQ SFVHIVQMFINTS (SEQ ID NO:2) (NCBI Reference Sequence: NP_751915.1) preferably from which the signal peptide has been cleaved, or, preferably, the mature form having the amino acid sequence of NWVNVISDLKKIEDLIQSMHIDAT-LYTESDVHPSCKVTAMKCFLLELQVISLESGDASIH DTVENLIILANNSLSSNGNVTESGCKECEELEEKNI-KEFLQSFVHIVQMFINTS (SEQ ID NO:3) (Grabstein et al., 1994, Science 264:965-968). In another specific embodiment, the IL-15 subunit is a mutant human IL-15 as described in Xu et al., 2013, Cancer Res 73:3075-3086. In another specific embodiment, the IL-15 subunit is a fusion protein, for example, wherein the IL-15 sequence is linked to the Fc portion of a human immunoglobulin, such as the Fc portion of human IgG (e.g., IgG1). In a specific embodiment, the IL-15Rα subunit is a cleaved form of IL-15Rα that is secreted by a cell in which it is expressed, such as the naturally produced cleaved form of IL-15Rα described in Chertova et al., 2013, J Biol Chem 288:18093-18103 or a secreted form of any of the other IL-15Rα isoforms. In a specific embodiment, the IL-15Rα isoform has the amino acid sequence of one of the following sequences from which the signal peptide has been cleaved: MAPR-RARGCRTLGLPALLLLLLLRPPATRGITCPPPMSVE-HADIWVKSYSLYSRERYICN SGFKRK-AGTSSLTECVLNKATNVAHWTTPSLKCIRDPALVHQR-PAPPSTVTTAGVTPQP ESLSPSGKEPAASSPSSNNTAATTAAIVPGSQLMPSK-SPSTGTTEISSHESSHGTPSQTTAK NWEL-TASASHQPPGVYPQGHSDTTVAISTSTVLLCGL-SAVSLLACYLKSRQTPPLASVE MEAMEALPVTWGTSSRDEDLENCSHHL (SEQ ID NO:4) (NCBI Reference Sequence: NP_002180.1), MAPR-RARGCRTLGLPALLLLLLLRPPATRGITCPPPMSVE-HADIWVKSYSLYSRERYICN SGFKRKAGTSSLTEC-VLNKATNVAHWTTPSLKCIKPAASSPSSNNTAAT-TAAIVPGSQL MPSKSPSTGTTEISSHESSHGTPSQT-TAKNWELTASASHQPPGVYPQGHSDTTVAISTSTV LLCGLSAVSLLACYLKSRQTPPLASVE-MEAMEALPVTWGTSSRDEDLENCSHHL (SEQ ID NO:5) (NCBI Reference Sequence: NP_751950.2), MSVE-HADIWVKSYSLYSRERYICNSGFKRK-AGTSSLTECVLNKATNVAHWTTPSLKCIR DPALVHQRPAPPSTVTTAGVTPQPESL-SPSGKEPAASSPSSNNTAATTAAIVPGSQLMPSK SPSTGTTEISSHESSHGTPSQTTAKNWEL-TASASHQPPGVYPQGHSDTTVAISTSTVLLCG LSAVSLLACYLKSRQTPPLASVE-MEAMEALPVTWGTSSRDEDLENCSHHL (SEQ ID NO:6) (NCBI Reference Sequence: NP_001230468.1), and MRLAGRQVPEQRSPPPPGLGSARPGSPAV-SCGAAAMAPRRARGCRTLGLPALLLLLLLR PPATRD-ARDRLAVLAGRSRISESFNHEVQTHEACVRLRT-MENCPQCHHHRTSRQQAGIT CPPPMSVEHADIWVKSYSLYSRERYICNSGFKRK-AGTSSLTECVLNKATNVAHWTTPSL KCIRD-PALVHQRPAPPSTVTTAGVTPQPESL-SPSGKEPAASSPSSNNTAATTAAIVPGSQL MPSKSPSTGTTEISSHESSHGTPSQTTAKNWEL-TASASHQPPGVYPQGHSDTTVAISTSTV LLCGL-SAVSLLACYLKSRQTPPLASVE-MEAMEALPVTWGTSSRDEDLENCSHHL (SEQ ID NO:7) (NCBI Reference Sequence: NP_001243694.1). In another specific embodiment, the IL-15Rα subunit is a fusion protein, for example, wherein the IL-15Rα sequence is linked to the Fc portion of a human immunoglobulin, such as the Fc portion of human IgG (e.g., IgG1). In a specific embodiment, the IL-15 subunit is a fusion protein, for example, wherein the IL-15 sequence is linked to the Fc portion of a human immunoglobulin, such as the Fc portion of human IgG (e.g., IgG1), and the IL-15Rα subunit is a fusion protein, for example, wherein the IL-15Rα sequence is linked to the Fc portion of a human immunoglobulin, such as the Fc portion of human IgG (e.g., IgG1).

In a specific embodiment, the soluble IL-15/IL-15Rα complexes are produced by cells transduced with vector(s) to co-express within the same cell the IL-15 subunit and the IL-15Rα subunit. In a preferred embodiment, the IL-15 subunit and the IL-15Rα subunit are expressed from two different vectors within the same cell. Preferably, the soluble IL-15/IL-15Rα complexes are secreted by a cell that recombinantly expresses the IL-15 subunit and the IL-15Rα subunit, and can be recovered from cell culture supernatant.

In a specific embodiment, the soluble IL-15/IL-15Rα complexes are produced by adding purified IL-15 subunit to a culture of cells transduced with a vector comprising a nucleotide sequence encoding the IL-15Rα subunit, which cells secrete the encoded IL-15Rα subunit, and recovering the soluble IL-15/IL-15Rα complexes from the cell culture supernatant. The IL-15 subunit can be from a previously purified, cryopreserved preparation or a commercially available product or recovered from cell culture supernatant of cells transduced with a vector comprising a nucleotide sequence encoding the IL-15 subunit, which cells secrete the encoded IL-15 subunit. Since IL-15 is typically transiently expressed when recombinantly expressed in cells in the absence of recombinant co-expression in the same cell of IL-15Rα, in order to avoid the need for repeated transduction of cells for purposes of producing IL-15 alone, obtaining an IL-15 subunit from a cryopreserved preparation or commercially available source is preferred for use in the adding step.

In specific embodiments, the soluble IL-15/IL-15Rα complexes are produced by complexing the IL-15 subunit and the IL-15Rα subunit ex vivo. In a specific embodiment, the IL-15 subunit is a commercially available product or is recovered from cell culture supernatant of cells transduced with a vector comprising a nucleotide sequence encoding the IL-15 subunit, which cells secrete the encoded IL-15 subunit. The IL-15Rα subunit can be a commercially available product or recovered from cell culture supernatant of cells transduced with a vector comprising a nucleotide sequence encoding the IL-15Rα subunit, which cells secrete the encoded IL-15Rα subunit. The IL-15 subunit and the IL-15Rα subunit can be complexed ex vivo by any method known in the art for complexing proteins ex vivo, such as by combining purified IL-15 subunit proteins and purified IL-15Rα subunit proteins ex vivo in a buffered solution (for example, in the presence of bovine serum albumin in phosphate-buffered saline (PBS)) at 37° C. for a period of time (for example, as described in Epardaud et al., 2008, Cancer Res 68:2972-2983).

Any mammalian cell line cells that can be passaged in vitro can be used for producing the soluble IL-15/IL-15Rα complexes, the IL15 subunit and/or the IL-15Rα subunit, such as Ba/F3 cells (i.e., Baf-3 cells), K562 cells, or murine fibroblast NIH 3T3 based artificial antigen presenting cells (AAPCs) (Hasan et al., 2009, J Immunol 183: 2837-2850). The cells can be human, murine, hamster, or other mammalian cells. The soluble IL-15/IL-15Rα complexes, the IL15 subunit and/or the IL-15Rα subunit can be purified from the supernatants from the culture of transduced cells by any method known in the art for purifying proteins, such as by fast protein liquid chromatography (FPLC). Non-limiting exemplary methods of producing the soluble IL-15/IL-15Rα complexes are described in Section 6; Tamzalit et al., 2014, Proc Natl Acad Sci USA 111:8565-8570; Chertova et al., 2013, J Biol Chem 288:18093-18103; and Xu et al., 2013, Cancer Res 73:3075-3086.

In some embodiments, the preparation of soluble IL-15/IL-15Rα complexes produced as described herein is free of cells recombinantly expressing the soluble IL-15/IL-15Rα complexes. In other embodiments, the preparation of soluble IL-15/IL-15Rα complexes produced as described herein contains cells recombinantly expressing the soluble IL-15/IL-15Rα complexes. When the preparation of soluble IL-15/IL-15Rα complexes contains cells recombinantly expressing the soluble IL-15/IL-15Rα complexes, the method of generating a population of cells comprising antigen-specific T cells further comprises, before the step of adding soluble IL-15/IL-15Rα complexes to the culture, a step of removing the cells recombinantly expressing the soluble IL-15/IL-15Rα complexes from the preparation or a step of purifying the soluble IL-15/IL-15Rα complexes from the preparation so as to separate the complexes from the cells recombinantly expressing the soluble IL-15/IL-15Rα complexes. The removing or purifying can be performed by any method known in the art for removing cells from a mixture of cells and proteins or purifying proteins from a mixture of cells and proteins, such as by centrifugation or by use of a filter.

In certain embodiments, the soluble IL-15/IL-15Rα complexes are thawed from a cryopreserved stock before being added to the culture. In a specific embodiment, the method of generating a population of cells comprising antigen-specific T cells further comprises thawing the soluble IL-15/IL-15Rα complexes from a cryopreserved stock before adding them to the culture. In a further specific embodiment, the method of generating a population of cells comprising antigen-specific T cells further comprises cryopreserving soluble IL-15/IL-15Rα complexes and thawing the soluble IL-15/IL-15Rα complexes before adding them to the culture. In a particular embodiment, cryopreserving soluble IL-15/IL-15Rα complexes comprises combining soluble IL-15/IL-15Rα complexes with a cryopreservative, such as dimethyl sulfoxide (DMSO), glycerol, polyvinylpyrrolidine, polyethylene glycol, albumin (such as bovine serum albumin), dextran, sucrose, ethylene glycol, i-erythritol, D-ribitol, D-mannitol, D-sorbitol, i-inositol, D-lactose, choline chloride, amino acids, methanol, acetamide, glycerol monoacetate, inorganic salts, or any cryopreservative known in the art for use in cryopreserving proteins. The concentration of the soluble IL-15/IL-15Rα complexes in the cryopreserved stock can be any concentration suitable for long-term storage of the complexes, such as 10 µg/ml to 10 mg/ml (for example, 10 µg/ml to 0.1 mg/ml, 0.1 mg/ml to 1 mg/ml, or 1 mg/ml to 10 mg/ml). In a specific embodiment, the concentration of the soluble IL-15/IL-15Rα complexes in the cryopreserved stock is about 0.1 mg/ml (i.e., 0.1±20% mg/ml). The cryopreserved soluble IL-15/IL-15Rα complexes can be stored in liquid nitrogen or dry ice for long-term storage, or a fridge (0-8° C.) for short-term storage (such as up to a week or 1-3 days).

In specific embodiments, the aforementioned period of time in culture (termed herein "the Sensitization Culture Time;" i.e., the culture time period over which ex vivo culturing occurs) is at least 14 days (preferably, at least 21 days). In a specific embodiment, the Sensitization Culture Time is in the range of 21-28 days. In another specific embodiment, the Sensitization Culture Time is 21 days. In another specific embodiment, the Sensitization Culture Time is 22 days. In another specific embodiment, the Sensitization Culture Time is 23 days. In another specific embodiment, the Sensitization Culture Time is 24 days. In another specific embodiment, the Sensitization Culture Time is 25 days. In another specific embodiment, the Sensitization Culture Time is 26 days. In another specific embodiment, the Sensitization Culture Time is 27 days. In a preferred embodiment, the Sensitization Culture Time is 28 days. In specific embodiments, the Sensitization Culture Time is at least 28 days.

In specific embodiments, the method of generating a population of cells comprising antigen-specific T cells further comprises, after the step of ex vivo culturing, a step of cryopreserving the cultured (and preferably expanded) human antigen-specific T cells, or a fraction thereof. In a specific embodiment, the method of generating a population of cells comprising antigen-specific T cells further comprises, after the step of cryopreserving, steps of thawing and optionally expanding in culture the cryopreserved human antigen-specific T cells or a faction thereof. The cryopreserving and thawing steps can be performed by known methods in the art for cryopreserving T cells and thawing T cells, respectively.

As noted above, the term "about" shall be construed so as to allow normal variation, such as, for example, a variation within 20%.

5.1.3. The Population of Human Blood Cells

In certain embodiments, the method of generating a population of cells comprising antigen-specific T cells described herein further comprises a step of deriving the population of human blood cells from a human blood cell sample. The human blood cell sample can be any cell sample that contains T cells, such as, but is not limited to, a hematopoietic cell sample, a fractionated or unfractionated whole blood sample, a fractionated or unfractionated apheresis collection (e.g., a leukapheresis collection, such as leukopak), PBMCs, or a T cell population (e.g., T cells enriched from PBMCs). In a preferred embodiment, the human blood cell sample is a human PBMC sample. PBMCs can be isolated from the blood sample by any method known in the art to isolate PBMCs from a blood sample, such as by Ficoll-Hypaque centrifugation as described in Koehne et al., 2000, Blood 96:109-117 or Trivedi et al., 2005, Blood 105:2793-2801. In another specific embodiment, the human blood cell sample is a population enriched in T cells from PBMCs. T cells can be enriched for from the PBMCs by any method known in the art to enrich for T cells from a blood sample or PBMCs. Non-limiting exemplary methods for enriching for T cells from PBMCs can be found in Koehne et al., 2000, Blood 96:109-117; Trivedi et al., 2005, Blood 105:2793-2801; Hasan et al., 2009, J Immunol 183: 2837-2850; and Koehne et al., 2015, Biol Blood Marrow Transplant 21: 1663-1678. For example, T cells can be enriched for from PBMCs by sorting the PBMCs using an anti-CD3 antibody and/or depleting from the PBMCs adherent monocytes and natural killer cells.

In preferred embodiments, the population of human blood cells is derived from a human donor that is seropositive for the one or more antigens. In certain embodiments, the population of human blood cells is derived from a human donor that is seronegative for the one or more antigens.

In some embodiments, the population of human blood cells is derived autologously from the human patient. In other embodiments, the population of human blood cells is derived from a human donor that is allogeneic to the human patient. In a specific embodiment, the human patient has been the recipient of a transplant from a transplant donor, and the human donor is a third-party donor that is different from the transplant donor. In another specific embodiment, the human patient has been the recipient of a transplant from a transplant donor, and the human donor is the transplant donor. The transplant can be a hematopoietic stem cell transplantation (HSCT) (such as a peripheral blood stem cell transplantation, a bone marrow transplantation, or a cord blood transplantation) or a solid organ transplant (such as a kidney transplant, a liver transplant, a heart transplant, an intestinal transplant, a pancreas transplant, a lung transplant, or a small bowel transplant).

The human donor from whom the population of human blood cells is derived can be an adult (at least age 16), an adolescent (age 12-15), a child (under age 12), a fetus, or a neonate. In a specific embodiment, the human donor from whom the population of human blood cells is derived is an adult. In a specific embodiment, the population of human blood cells is derived from human (umbilical) cord blood.

In specific embodiments, the population of human blood cells used in accordance with the methods of generating a population of cells comprising antigen-specific T cells described herein comprises $CD4^+$ T cells. In specific embodiments, the population of human blood cells used in accordance with the methods of generating a population of cells comprising antigen-specific T cells described herein comprises $CD8^+$ T cells. In a preferred embodiment, the population of human blood cells used in accordance with the methods of generating a population of cells comprising antigen-specific T cells described herein comprises both $CD4^+$ and $CD8^+$ T cells.

The population of human blood cells used in accordance with the methods of generating a population of cells comprising antigen-specific T cells described herein preferably contains at least 50% T cells. In a specific embodiment, the population of human blood cells contains at least 60% T cells. In another specific embodiment, the population of human blood cells contains at least 70% T cells. In a specific embodiment, the population of human blood cells contains at least 80% T cells. In a specific embodiment, the population of human blood cells contains at least 90% T cells. In a specific embodiment, the population of human blood cells contains at least 95% T cells. In a specific embodiment, the population of human blood cells contains at least 99% T cells. In a specific embodiment, the population of human blood cells contains 100% T cells.

In certain embodiments, the population of human blood cells used in accordance with the methods of generating a population of cells comprising antigen-specific T cells described herein contains, at initiation of culture, at least 50% memory T cells. In a specific embodiment, the population of human blood cells used in accordance with the methods of generating a population of cells comprising antigen-specific T cells described herein contains, at initiation of culture, at least 60% memory T cells. In another specific embodiment, the population of human blood cells used in accordance with the methods of generating a population of cells comprising antigen-specific T cells described herein contains, at initiation of culture, at least 70% memory T cells. In another specific embodiment, the population of human blood cells used in accordance with the methods of generating a population of cells comprising antigen-specific T cells described herein contains, at initiation of culture, at least 80% memory T cells. In another specific embodiment, the population of human blood cells used in accordance with the methods of generating a population of cells comprising antigen-specific T cells described herein contains, at initiation of culture, at least 90% memory T cells. In another specific embodiment, the population of human blood cells used in accordance with the methods of generating a population of cells comprising antigen-specific T cells described herein contains, at initiation of culture, at least 95% memory T cells. In another specific embodiment, the population of human blood cells used in accordance with the methods of generating a population of cells comprising antigen-specific T cells described herein contains, at initiation of culture, at least 99% memory T cells. In another specific embodiment, the population of human blood cells used in accordance with the methods of generating a population of cells comprising antigen-specific T cells described herein contains, at initiation of culture, 100% memory T cells. In specific embodiments when the method of generating a population of cells comprising antigen-specific T cells described herein further comprises a step of deriving the population of human blood cells from a human blood cell sample (preferably, a human PBMC sample), the deriving step comprises enriching for memory T cells from the human blood cell sample (such as by affinity selection for cells that express cell surface markers of memory T cells (e.g., using antibodies to the cell surface markers)). In a particular embodiment, the enriching step comprises sorting memory T cells from the human blood cell sample (preferably, a human PBMC sample) by fluorescence-activated cell sorting (FACS). In another particular embodiment, the enriching step comprises sorting memory T cells from the human blood cell sample (preferably, a human PBMC sample) by magnetic separation. In specific embodiments when the method of generating a population of cells comprising antigen-specific T cells described herein further comprises a step of deriving the population of human blood cells from a human blood cell sample (preferably, a human PBMC sample), the deriving step comprises in vitro reprogramming cells in the human blood cell sample to turn them into memory T cells. The memory T cells described herein can be central memory T cells ($T_{CM}$ cells), stem cell-like memory T cells ($T_{SCM}$ cells), effector memory T cells ($T_{EM}$ cells), or a combination thereof.

In preferred embodiments, the population of human blood cells used in accordance with the methods of generating a population of cells comprising antigen-specific T cells described herein contains, at initiation of culture, at least 50% $T_{CM}$ cells. In a specific embodiment, the population of human blood cells used in accordance with the methods of generating a population of cells comprising antigen-specific T cells described herein contains, at initiation of culture, at least 60% $T_{CM}$ cells. In a specific embodiment, the population of human blood cells used in accordance with the methods of generating a population of cells comprising antigen-specific T cells described herein contains, at initiation of culture, at least 70% $T_{CM}$ cells. In a specific embodiment, the population of human blood cells used in accordance with the methods of generating a population of cells comprising antigen-specific T cells described herein contains, at initiation of culture, at least 80% $T_{CM}$ cells. In a specific embodiment, the population of human blood cells used in accordance with the methods of generating a population of cells comprising antigen-specific T cells described herein contains, at initiation of culture, at least 90% $T_{CM}$ cells. In a specific embodiment, the population of human blood cells used in accordance with the methods of generating a population of cells comprising antigen-specific T cells described herein contains, at initiation of culture, at least 95% $T_{CM}$ cells. In a specific embodiment, the population of human blood cells used in accordance with the methods of generating a population of cells comprising antigen-specific T cells described herein contains, at initiation of culture, at least 99% $T_{CM}$ cells. In a specific embodiment, the population of human blood cells used in accordance with the methods of generating a population of cells comprising antigen-specific T cells described herein contains, at initiation of culture, 100% $T_{CM}$ cells. In specific embodiments when the method of generating a population of cells comprising antigen-specific T cells described herein further comprises a step of deriving the population of human blood cells from a human blood cell sample (preferably, a human PBMC sample), the deriving step comprises enriching for $T_{CM}$ cells from the human blood cell sample (such as by affinity selection for cells that express cell surface markers of $T_{CM}$ cells (e.g., using antibodies to the cell surface markers)). In a particular embodiment, the enriching step comprises sorting $T_{CM}$ cells from the human blood cell sample (preferably, a human PBMC sample) by fluorescence-activated cell sorting (FACS). In another particular embodiment, the enriching step comprises sorting $T_{CM}$ cells from the human blood cell sample (preferably, a human PBMC sample) by magnetic separation. In specific embodiments when the method of generating a population of cells comprising antigen-specific T cells described herein further comprises a step of deriving the population of human blood cells from a human blood cell sample (preferably, a human PBMC sample), the deriving step comprises in vitro reprogramming cells in the human blood cell sample to turn them into $T_{CM}$ cells.

In specific embodiments, the population of human blood cells used in accordance with the methods of generating a population of cells comprising antigen-specific T cells described herein contains, at initiation of culture, at least 50% $T_{SCM}$ cells. In a specific embodiment, the population of human blood cells used in accordance with the methods of generating a population of cells comprising antigen-specific T cells described herein contains, at initiation of culture, at least 60% $T_{SCM}$ cells. In a specific embodiment, the population of human blood cells used in accordance with the methods of generating a population of cells comprising antigen-specific T cells described herein contains, at initiation of culture, at least 70% $T_{SCM}$ cells. In a specific embodiment, the population of human blood cells used in accordance with the methods of generating a population of cells comprising antigen-specific T cells described herein contains, at initiation of culture, at least 80% $T_{SCM}$ cells. In a specific embodiment, the population of human blood cells used in accordance with the methods of generating a population of cells comprising antigen-specific T cells described herein contains, at initiation of culture, at least 90% $T_{SCM}$ cells. In a specific embodiment, the population of human blood cells used in accordance with the methods of generating a population of cells comprising antigen-specific T cells described herein contains, at initiation of culture, at least 95% $T_{SCM}$ cells. In a specific embodiment, the population of human blood cells used in accordance with the methods of generating a population of cells comprising antigen-specific T cells described herein contains, at initiation of culture, at least 99% $T_{SCM}$ cells. In a specific embodiment, the population of human blood cells used in accordance with the methods of generating a population of cells comprising antigen-specific T cells described herein contains, at initiation of culture, 100% $T_{SCM}$ cells. In specific embodiments when the method of generating a population of cells comprising antigen-specific T cells described herein further comprises a step of deriving the population of human blood cells from a human blood cell sample (preferably, a human PBMC sample), the deriving step comprises enriching for $T_{SCM}$ cells from the human blood cell sample (such as by affinity selection for cells that express cell surface markers of $T_{SCM}$ cells (e.g., using antibodies to the cell surface markers)). In a particular embodiment, the enriching step comprises sorting $T_{SCM}$ cells from the human blood cell sample (preferably, a human PBMC sample) by fluorescence-activated cell sorting (FACS). In another particular embodiment, the enriching step comprises sorting $T_{SCM}$ cells from the human blood cell sample (preferably, a human PBMC sample) by magnetic separation. In specific embodiments when the method of generating a population of cells comprising antigen-specific T cells described herein further comprises a step of deriving the population of human blood cells from a human blood cell sample (preferably, a human PBMC sample), the deriving step comprises in vitro reprogramming cells in the human blood cell sample to turn them into $T_{SCM}$ cells.

In specific embodiments, the population of human blood cells used in accordance with the methods of generating a population of cells comprising antigen-specific T cells described herein contains, at initiation of culture, at least 50% $T_{EM}$ cells. In a specific embodiment, the population of human blood cells used in accordance with the methods of generating a population of cells comprising antigen-specific T cells described herein contains, at initiation of culture, at least 60% $T_{EM}$ cells. In a specific embodiment, the population of human blood cells used in accordance with the methods of generating a population of cells comprising antigen-specific T cells described herein contains, at initiation of culture, at least 70% $T_{EM}$ cells. In a specific embodiment, the population of human blood cells used in accordance with the methods of generating a population of cells comprising antigen-specific T cells described herein contains, at initiation of culture, at least 80% $T_{EM}$ cells. In a specific embodiment, the population of human blood cells used in accordance with the methods of generating a population of cells comprising antigen-specific T cells described herein contains, at initiation of culture, at least 90% $T_{EM}$ cells. In a specific embodiment, the population of human blood cells used in accordance with the methods of generating a population of cells comprising antigen-specific T cells described herein contains, at initiation of culture, at least 95% $T_{EM}$ cells. In a specific embodiment, the population of human blood cells used in accordance with the methods of generating a population of cells comprising antigen-specific T cells described herein contains, at initiation of culture, at least 99% $T_{EM}$ cells. In a specific embodiment, the population of human blood cells used in accordance with the methods of generating a population of cells comprising antigen-specific T cells described herein contains, at initiation of culture, 100% $T_{EM}$ cells. In specific embodiments when the method of generating a population of cells comprising antigen-specific T cells described herein further comprises a step of deriving the population of human blood cells from a human blood cell sample (preferably, a human PBMC sample), the deriving step comprises enriching for $T_{EM}$ cells from the human blood cell sample (such as by affinity selection for cells that express cell surface markers of $T_{EM}$ cells (e.g., using antibodies to the cell surface markers)). In a particular embodiment, the enriching step comprises sorting $T_{EM}$ cells from the human blood cell sample (preferably, a human PBMC sample) by fluorescence-activated cell sorting (FACS). In another particular embodiment, the enriching step comprises sorting $T_{EM}$ cells from the human blood cell sample (preferably, a human PBMC sample) by magnetic separation. In specific embodiments when the method of generating a population of cells comprising antigen-specific T cells described herein further comprises a step of deriving the population of human blood cells from a human blood cell sample (preferably, a human PBMC sample), the deriving step comprises in vitro reprogramming cells in the human blood cell sample to turn them into $T_{EM}$ cells.

5.2. Methods of Treating Patients Using the Generated Antigen-Specific T Cells In another aspect, provided herein are methods of treating a human patient having a pathogen or cancer, comprising: (i) generating a population of cells comprising antigen-specific T cells according to a method described in Section 5.1; and (ii) administering the population of cells comprising antigen-specific T cells to the human patient.

In another aspect, provided herein are methods of treating a human patient having a pathogen or cancer, comprising administering a population of cells comprising antigen-specific T cells to the human patient, wherein the population of cells comprising antigen-specific T cells is the product of a method comprising generating the population of cells comprising antigen-specific T cells according to a method described in Section 5.1.

In specific embodiments, the administering of the population of cells comprising antigen-specific T cells does not result in any graft-versus-host disease (GvHD) in the human patient.

5.2.1. Administration and Dosage

The route of administration of the population of cells comprising antigen-specific T cells and the amount to be administered to the human patient can be determined based on the nature of the disease, condition of the human patient and the knowledge of the physician. Generally, the administration of the population of cells is intravenous. In certain embodiments, the method of treating comprises infusing to the human patient the population of cells comprising antigen-specific T cells. In specific embodiments, the infusing is by bolus intravenous infusion.

In some embodiments, the method of treating comprises administering to the human patient the population of cells comprising antigen-specific T cells, at a dose that is less than or equal to about $1 \times 10^5$ cells of the population of cells comprising antigen-specific T cells per kg of the human patient. In a specific embodiment, the method of treating comprises administering to the human patient the population of cells comprising antigen-specific T cells, at a dose that is less than or equal to about $5 \times 10^4$ cells of the population of cells comprising antigen-specific T cells per kg of the human patient. In another specific embodiment, the method of treating comprises administering to the human patient the population of cells comprising antigen-specific T cells, at a dose that is less than or equal to about $1 \times 10^4$ cells of the population of cells comprising antigen-specific T cells per kg of the human patient. In another specific embodiment, the method of treating comprises administering to the human patient the population of cells comprising antigen-specific T cells, at a dose that is less than or equal to about $5 \times 10^3$ cells of the population of cells comprising antigen-specific T cells per kg of the human patient. In another specific embodiment, the method of treating comprises administering to the human patient the population of cells comprising antigen-specific T cells, at a dose that is less than or equal to about $1 \times 10^3$ cells of the population of cells comprising antigen-specific T cells per kg of the human patient. In another specific embodiment, the method of treating comprises administering to the human patient the population of cells comprising antigen-specific T cells, at a dose that is less than or equal to about $5 \times 10^2$ cells of the population of cells comprising antigen-specific T cells per kg of the human patient (such dose being used preferably when the antigen-specific T cells are specific to one or more antigens of a virus, such as one or more antigens of cytomegalovirus (CMV)). In another specific embodiment, the method of treating comprises administering to the human patient the population of cells comprising antigen-specific T cells, at a dose that is less than or equal to about $1 \times 10^2$ cells of the population of cells comprising antigen-specific T cells per kg of the human patient (such dose being used preferably when the antigen-specific T cells are specific to one or more antigens of a virus, such as one or more antigens of CMV). In another specific embodiment, the method of treating comprises administering to the human patient the population of cells comprising antigen-specific T cells, at a dose of about $1\times10^2$ to $5\times10^2$ cells of the population of cells comprising antigen-specific T cells per kg of the human patient (such dose being used preferably when the antigen-specific T cells are specific to one or more antigens of a virus, such as one or more antigens of CMV). In another specific embodiment, the method of treating comprises administering to the human patient the population of cells comprising antigen-specific T cells, at a dose of about $5\times10^2$ to $1\times10^3$ cells of the population of cells comprising antigen-specific T cells per kg of the human patient (such dose being used preferably when the antigen-specific T cells are specific to one or more antigens of a virus, such as one or more antigens of CMV). In another specific embodiment, the method of treating comprises administering to the human patient the population of cells comprising antigen-specific T cells, at a dose of about $1\times10^3$ to $5\times10^3$ cells of the population of cells comprising antigen-specific T cells per kg of the human patient. In another specific embodiment, the method of treating comprises administering to the human patient the population of cells comprising antigen-specific T cells, at a dose of about $5\times10^3$ to $1\times10^4$ cells of the population of cells comprising antigen-specific T cells per kg of the human patient. In another specific embodiment, the method of treating comprises administering to the human patient the population of cells comprising antigen-specific T cells, at a dose of about $1\times10^4$ to $5\times10^4$ cells of the population of cells comprising antigen-specific T cells per kg of the human patient. In another specific embodiment, the method of treating comprises administering to the human patient the population of cells comprising antigen-specific T cells, at a dose of about $5\times10^4$ to $1\times10^5$ cells of the population of cells comprising antigen-specific T cells per kg of the human patient.

In other embodiments, the method of treating comprises administering to the human patient the population of cells comprising antigen-specific T cells, at a dose that is at least $1\times10^5$ cells of the population of cells comprising antigen-specific T cells per kg of the human patient. In a specific embodiment, the method of treating comprises administering to the human patient the population of cells comprising antigen-specific T cells, at a dose that is about $5\times10^5$ cells of the population of cells comprising antigen-specific T cells per kg of the human patient. In another specific embodiment, the method of treating comprises administering to the human patient the population of cells comprising antigen-specific T cells, at a dose that is about $1\times10^6$ cells of the population of cells comprising antigen-specific T cells per kg of the human patient. In another specific embodiment, the method of treating comprises administering to the human patient the population of cells comprising antigen-specific T cells, at a dose that is about $2\times10^6$ cells of the population of cells comprising antigen-specific T cells per kg of the human patient. In another specific embodiment, the method of treating comprises administering to the human patient the population of cells comprising antigen-specific T cells, at a dose that is about $3\times10^6$ cells of the population of cells comprising antigen-specific T cells per kg of the human patient. In another specific embodiment, the method of treating comprises administering to the human patient the population of cells comprising antigen-specific T cells, at a dose that is about $4\times10^6$ cells of the population of cells comprising antigen-specific T cells per kg of the human patient. In another specific embodiment, the method of treating comprises administering to the human patient the population of cells comprising antigen-specific T cells, at a dose that is about $5\times10^6$ cells of the population of cells comprising antigen-specific T cells per kg of the human patient. In another specific embodiment, the method of treating comprises administering to the human patient the population of cells comprising antigen-specific T cells, at a dose that is about $6\times10^6$ cells of the population of cells comprising antigen-specific T cells per kg of the human patient. In another specific embodiment, the method of treating comprises administering to the human patient the population of cells comprising antigen-specific T cells, at a dose that is about $1\times10^7$ cells of the population of cells comprising antigen-specific T cells per kg of the human patient. In another specific embodiment, the method of treating comprises administering to the human patient the population of cells comprising antigen-specific T cells, at a dose that is about $1\times10^5$ to $5\times10^5$ cells of the population of cells comprising antigen-specific T cells per kg of the human patient. In another specific embodiment, the method of treating comprises administering to the human patient the population of cells comprising antigen-specific T cells, at a dose that is about $5\times10^5$ to $1\times10^6$ cells of the population of cells comprising antigen-specific T cells per kg of the human patient. In another specific embodiment, the method of treating comprises administering to the human patient the population of cells comprising antigen-specific T cells, at a dose that is about $1\times10^6$ to $2\times10^6$ cells of the population of cells comprising antigen-specific T cells per kg of the human patient. In another specific embodiment, the method of treating comprises administering to the human patient the population of cells comprising antigen-specific T cells, at a dose that is about $2\times10^6$ to $5\times10^6$ cells of the population of cells comprising antigen-specific T cells per kg of the human patient. In another specific embodiment, the method of treating comprises administering to the human patient the population of cells comprising antigen-specific T cells, at a dose that is about $5\times10^6$ to $1\times10^7$ cells of the population of cells comprising antigen-specific T cells per kg of the human patient.

In certain embodiments, the method of treating comprises administering to the human patient the population of cells comprising antigen-specific T cells at the dose described above weekly. In certain embodiments, the method of treating comprises administering to the human patient the population of cells comprising antigen-specific T cells at the dose described above twice weekly. In certain embodiments, the method of treating comprises administering to the human patient the population of cells comprising antigen-specific T cells at the dose described above biweekly. In certain embodiments, the method of treating comprises administering to the human patient the population of cells comprising antigen-specific T cells at the dose described above every three weeks.

In certain embodiments, the method of treating comprises administering to the human patient at least 2 doses of the population of cells comprising antigen-specific T cells. In specific embodiments, the method of treating comprises administering to the human patient 2, 3, 4, 5, or 6 doses of the population of cells comprising antigen-specific T cells. In a specific embodiment, the method of treating comprises administering to the human patient 2 doses of the population of cells comprising antigen-specific T cells. In another specific embodiment, the method of treating comprises administering to the human patient 3 doses of the population of cells comprising antigen-specific T cells. In another specific embodiment, the method of treating comprises administering to the human patient 4 doses of the population of cells comprising antigen-specific T cells.

In specific embodiments, the method of treating comprises administering to the human patient at least two cycles (e.g., 2, 3, 4, 5, or 6 cycles) of one dose per week of the population of cells comprising antigen-specific T cells for at least two consecutive weeks (e.g., 2, 3, 4, 5, or 6 consecutive weeks), each cycle separated by a washout period during which no dose of the population of cells comprising antigen-specific T cells is administered. In a specific embodiment, the at least two consecutive weeks are 2 consecutive weeks. In a preferred embodiment, the at least two consecutive weeks are 3 consecutive weeks. In another specific embodiment, the at least two consecutive weeks are 4 consecutive weeks. In another specific embodiment, the method of treating comprises administering to the human patient two, three, four, five, or six cycles of one dose per week of the population of cells comprising antigen-specific T cells for three consecutive weeks, each cycle separated by a washout period during which no dose of the population of cells comprising antigen-specific T cells is administered. In another specific embodiment, the method of treating comprises administering to the human patient a first cycle of one dose per week of the population of cells comprising antigen-specific T cells for 3 consecutive weeks followed by a washout period during which no dose of the population of cells comprising antigen-specific T cells is administered, followed by a second cycle of said one dose per week of the population of cells comprising antigen-specific T cells for 3 consecutive weeks. In specific embodiments, the washout period is at least about 1 week (e.g., about 1-6 weeks). In specific embodiments, the washout period is about 1, 2, 3, or 4 weeks. In a specific embodiment, the washout period is about 2 weeks. In a preferred embodiment, the washout period is about 3 weeks. In another specific embodiment, the washout period is about 4 weeks. Preferably, an additional cycle is administered only when the previous cycle has not exhibited toxicity (for example, no grade 3-5 serious adverse events, graded according to NCI CTCAE 4.0).

In specific embodiments, the method of treating comprises administering to the human patient continuously the population of cells comprising antigen-specific T cells at a dose described herein weekly (i.e., there is no week during which the population of cells comprising antigen-specific T cells is not administered, and thus there is no washout period).

In certain embodiments, a first dosage regimen described herein is carried out for a first period of time, followed by a second and different dosage regimen described herein that is carried out for a second period of time, wherein the first period of time and the second period of time are optionally separated by a washout period. In specific embodiments, the washout period is at least about 1 week (e.g., about 1-6 weeks). In specific embodiments, the washout period is about 1, 2, 3, or 4 weeks. In a specific embodiment, the washout period is about 2 weeks. In a preferred embodiment, the washout period is about 3 weeks. In another specific embodiment, the washout period is about 4 weeks. Preferably, the second dosage regimen is carried out only when the first dosage regimen has not exhibited toxicity (for example, no grade 3-5 serious adverse events, graded according to NCI CTCAE 4.0).

As noted above, the term "about" shall be construed so as to allow normal variation, such as, for example, a variation within 20%.

5.2.2. Serial Treatment with Different Cell Populations

In certain embodiments, the method of treating a human patient having a pathogen or cancer as described above further comprises, after administering to the human patient a first population of cells comprising antigen-specific T cells that is generated by a method described in Section 5.1, administering to the human patient a second population of cells comprising antigen-specific T cells that is generated by a method described in Section 5.1, wherein the antigen-specific T cells in the second population of cells comprising antigen-specific T cells are restricted by a different HLA allele (different from the HLA allele by which antigen-specific cells contained in the first population of cells comprising antigen-specific T cells are restricted) shared with the diseased cells in the human patient. In a specific embodiment, the method of treating a human patient having a pathogen or cancer comprises administering a first cycle of one dose per week of the first population of cells comprising antigen-specific T cells, for at least two consecutive weeks (e.g., 2, 3, 4, 5, or 6 consecutive weeks), optionally followed by a washout period during which no dose of any population of cells comprising antigen-specific T cells is administered, and followed by a second cycle of one dose per week of the second population of cells comprising antigen-specific T cells for at least two consecutive weeks (e.g., 2, 3, 4, 5, or 6 consecutive weeks). In specific embodiments, the washout period is at least about 1 week (e.g., about 1-6 weeks). In specific embodiments, the washout period is about 1, 2, 3, or 4 weeks. In a specific embodiment, the washout period is about 2 weeks. In a preferred embodiment, the washout period is about 3 weeks. In certain embodiments, the human patient has no response, an incomplete response, or a suboptimal response (i.e., the human patient may still have a substantial benefit from continuing treatment, but has reduced chances of optimal long-term outcomes) after administering the first population of cells comprising antigen-specific T cells and prior to administering the second population of cells comprising antigen-specific T cells.

The first and second populations of cells comprising antigen-specific T cells can each be administered by any route and any dosage regimen as described in Section 5.2.1, supra.

In specific embodiments, two populations of cells comprising antigen-specific T cells that are each restricted (i.e., antigen-specific T cells in the two populations of cells are each restricted) by a different HLA allele shared with the diseased cells in the human patient and that are each generated by a method described in Section 5.1 are administered serially. In specific embodiments, three populations of cells comprising antigen-specific T cells that are each restricted (i.e., antigen-specific T cells in the three populations of cells are each restricted) by a different HLA allele shared with the diseased cells in the human patient and that are each generated by a method described in Section 5.1 are administered serially. In specific embodiments, four populations of cells comprising antigen-specific T cells that are each restricted (i.e., antigen-specific T cells in the four populations of cells are each restricted) by a different HLA allele shared with the diseased cells in the human patient and that are each generated by a method described in Section 5.1 are administered serially. In specific embodiments, more than four populations of cells comprising antigen-specific T cells that are each restricted (i.e., antigen-specific T cells in the more than four populations of cells are each restricted) by a different HLA allele shared with the diseased cells in the human patient and that are each generated by a method described in Section 5.1 are administered serially.

5.2.3. Additional Therapies

In specific embodiments, the method of treating a human patient having a pathogen or cancer further comprises concurrently treating the human patient with a second therapy for the pathogen or cancer, which second therapy is not treatment with a population of cells comprising antigen-specific T cells according to the invention, for example, at about the same time, the same day, or same week, or same treatment period (treatment cycle) during which the population of cells comprising antigen-specific T cells is administered, or on similar dosing schedules, or on different but overlapping dosing schedules. In specific embodiments, no second therapy for the pathogen or cancer is concurrently administered to the human patient over a period of time over which the population of cells is repeatedly administered to the human patient. In specific embodiments, the method of treating a human patient having a pathogen or cancer further comprises, before the administering step, a step of treating the human patient with a second therapy for the pathogen or cancer, which is not treatment with a population of cells comprising antigen-specific T cells according to the invention.

5.3. Population of Cells Comprising Antigen-Specific T Cells

In another aspect, provided herein are isolated populations of cells comprising antigen-specific T cells for therapeutic administration to a human patient having or suspected of having a pathogen or cancer, wherein the isolated population of cells comprising antigen-specific T cells is the product of a method comprising generating the population of cells comprising antigen-specific T cells according to a method described in Section 5.1, supra. In specific embodiments, provided herein is an isolated population of cells comprising antigen-specific T cells for therapeutic administration to a human patient having or suspected of having a pathogen or cancer, wherein the isolated population of cells comprising antigen-specific T cells is the product of a method comprising generating the population of cells comprising antigen-specific T cells according to a method described in Section 5.1, supra, and wherein the population of cells comprising antigen-specific T cells is cryopreserved.

In specific embodiments, the isolated population of cells comprising antigen-specific T cells comprises $CD8^+$ T cells. In specific embodiments, the isolated population of cells comprising antigen-specific T cells comprises $CD4^+$ T cells. In specific embodiments, the isolated population of cells comprising antigen-specific T cells comprises both $CD8^+$ and $CD4^+$ T cells.

Also provided herein is a cell bank comprising a plurality of isolated populations of cells comprising antigen-specific T cells described herein. Preferably, information as to antigen reactivity (for example, cytotoxicity), alloreactivity, HLA restriction, and/or assignment, as described in Section 5.4, is ascertained for each of the plurality of isolated populations of cells comprising antigen-specific T cells contained in the cell bank, and linked to the identifier of the corresponding population of cells comprising antigen-specific T cells, so as to facilitate the selection of a suitable population of cells comprising antigen-specific T cells from the plurality for therapeutic administration to a human patient.

5.4. Characteristics of the Generated Antigen-Specific T Cells

To be suitable for therapeutic administration to a human patient in adoptive immunotherapy, the population of cells comprising antigen-specific T cells that is generated by a method described in Section 5.1, supra, preferably (1) exhibits substantial antigen reactivity (for example, cytotoxicity) toward fully or partially HLA-matched (relative to the human donor of the population of human blood cells used to generate the population of cells) antigen presenting cells that present the one or more antigens (e.g., antigen presenting cells that are loaded with or genetically engineered to express one or more peptides or proteins derived from the one or more antigens of the pathogen or cancer); and (2) lacks substantial alloreactivity. When a particular human patient exists or when a potential particular human patient is envisioned, the population of cells comprising antigen-specific T cells that is generated by a method described in Section 5.1, supra, also preferably is restricted (i.e., the antigen-specific T cells contained in the population of cells comprising antigen-specific T cells are restricted) by an HLA allele shared with the diseased cells in the human patient, and/or shares (i.e., the antigen-specific T cells contained in the population of cells comprising antigen-specific T cells share) at least 2 HLA alleles (e.g., at least 2 out of 8 HLA alleles or at least 2 out of 10 HLA alleles) with the diseased cells in the human patient. Thus, preferably, antigen reactivity (for example, cytotoxicity), alloreactivity, information as to which HLA allele(s) the population of cells comprising antigen-specific T cells is restricted (i.e., to which HLA allele(s) the antigen-specific T cells contained in the population of cells comprising antigen-specific T cells are restricted), and/or the HLA assignment of the population of cells comprising antigen-specific T cells (i.e., the HLA assignment of the antigen-specific T cells contained in the population of cells comprising antigen-specific T cells) are measured by a method known in the art before administration to a human patient (for example, such a method as described in Koehne et al., 2000, Blood 96:109-117; Trivedi et al., 2005, Blood 105:2793-2801; Haque et al., 2007, Blood 110:1123-1131; Hasan et al., 2009, J Immunol 183: 2837-2850; Feuchtinger et al., 2010, Blood 116:4360-4367; Doubrovina et al., 2012, Blood 120:1633-1646; Leen et al., 2013, Blood 121:5113-5123; Papadopoulou et al., 2014, Sci Transl Med 6:242ra83; Sukdolak et al., 2013, Biol Blood Marrow Transplant 19:1480-1492; Koehne et al., 2015, Biol Blood Marrow Transplant 21: 1663-1678; Weren et al., J Immunol Methods, 289:17-26; Shafer-Weaver et al., 2003, J Transl Med 1:14; Nagorsen and Marincola, ed., 2005, Analyzing T Cell Responses: How to Analyze Cellular Immune Responses against Tumor Associated Antigens, Springer Netherlands; International Patent Application Publication No. WO 2016/073550; or International Patent Application Publication No. WO 2017/044678).

5.4.1. Cytotoxicity and Other Measures of Antigen Reactivity

The antigen reactivity (for example, cytotoxicity) of a population of cells comprising antigen-specific T cells described herein toward fully or partially HLA-matched (relative to the human donor of the population of human blood cells used to generate the population of cells) antigen presenting cells can be determined by any assay known in the art to measure T cell mediated antigen reactivity (for example, cytotoxicity), such as, but is not limited to, a method described in Nagorsen and Marincola, ed., 2005, Analyzing T Cell Responses: How to Analyze Cellular Immune Responses against Tumor Associated Antigens, Springer Netherlands. The assay can be performed using the population of cells comprising antigen-specific T cells directly, an aliquot thereof, or a precursor cell population that indicates the antigen reactivity (for example, cytotoxicity) of the population of cells comprising antigen-specific T cells. In a specific embodiment, the antigen reactivity (for example, cytotoxicity) is determined by a standard $^{51}$Cr release assay, an IFN-γ-production assay, a limiting dilution assay to measure CTL precursors (CTLps), a perforin release assay, a granzyme B release assay, or a CD107 mobilization assay, as described in Trivedi et al., 2005, Blood 105:2793-2801; Hasan et al., 2009, J Immunol 183: 2837-2850; Doubrovina et al., 2012, Blood 119:2644-2656; Koehne et al., 2000, Blood 96:109-117; Weren et al., J Immunol Methods, 289:17-26; Shafer-Weaver et al., 2003, J Transl Med 1:14; or Nagorsen and Marincola, ed., 2005, Analyzing T Cell Responses: How to Analyze Cellular Immune Responses against Tumor Associated Antigens, Springer Netherlands.

In certain embodiments, the population of cells comprising antigen-specific T cells generated by a method described in Section 5.1 exhibits substantial antigen reactivity (for example, cytotoxicity) in vitro toward (e.g., exhibits substantial lysis of) fully or partially HLA matched antigen presenting cells that present the one or more antigens (e.g., antigen presenting cells that are loaded with or genetically engineered to express one or more peptides or proteins derived from the antigen of the pathogen or cancer). Preferably, the fully or partially HLA-matched antigen presenting cells are fully HLA-matched antigen presenting cells (e.g., antigen presenting cells derived from the human donor of the population of human blood cells used to generate the population of cells). In specific embodiments, the population of cells comprising antigen-specific T cells generated by a method described in Section 5.1 exhibits lysis of greater than or equal to 20%, 25%, 30%, 35%, or 40% of the fully or partially HLA-matched antigen presenting cells that present the one or more antigens (e.g., antigen presenting cells that are loaded with or genetically engineered to express one or more peptides or proteins derived from the antigen of the pathogen or cancer). In a specific embodiment, the population of cells comprising antigen-specific T cells generated by a method described in Section 5.1 exhibits lysis of greater than or equal to 20% of the fully or partially HLA-matched antigen presenting cells that present the one or more antigens (e.g., antigen presenting cells that are loaded with or genetically engineered to express one or more peptides or proteins derived from the antigen of the pathogen or cancer).

Antigen presenting cells that can be used in the antigen reactivity (for example, cytotoxicity) assay include, but are not limited to, dendritic cells, phytohemagglutinin (PHA)-lymphoblasts, macrophages, B-cells that generate antibodies, EBV-BLCL cells, and artificial antigen presenting cells (AAPCs).

In specific embodiments, the fully or partially HLA-matched antigen presenting cells used in the antigen reactivity (for example, cytotoxicity) assay are loaded with a pool of peptides derived from the antigen of the pathogen or cancer. The pool of peptides, can be, for example, a pool of overlapping peptides (e.g., pentadecapeptides) spanning the sequence of the antigen of the pathogen or cancer.

5.4.2. Alloreactivity

Alloreactivity of a population of cells comprising antigen-specific T cells described herein can be measured using an antigen reactivity (for example, cytotoxicity) assay known in the art to measure T cell mediated antigen reactivity (for example, cytotoxicity), such as, but is not limited to, a standard $^{51}$Cr release assay, an IFN-γ-production assay, a limiting dilution assay to measure CTL precursors (CTLps), a perforin release assay, a granzyme B release assay, a CD107 mobilization assay, or any other antigen reactivity assay as described in Section 5.4.1, but with antigen presenting cells that do not present the one or more antigens (e.g., antigen presenting cells that are not loaded with or genetically engineered to express one or more peptides or proteins derived from the antigen of the pathogen or cancer), and/or HLA-mismatched (relative to the human donor of the population of human blood cells used to generate the population of cells) antigen presenting cells. The assay can be performed using the population of cells comprising antigen-specific T cells directly, an aliquot thereof, or a precursor cell population that indicates the alloreactivity of the population of cells comprising antigen-specific T cells. A population of cells comprising antigen-specific T cells that lacks substantial alloreactivity results generally in the absence of graft-versus-host disease (GvHD) when administered to a human patient.

In certain embodiments, the population of cells comprising antigen-specific T cells generated by a method described in Section 5.1 lacks substantial antigen reactivity (for example, cytotoxicity) in vitro toward antigen presenting cells that do not present the one or more antigens (e.g., antigen presenting cells that are not loaded with or genetically engineered to express one or more peptides or proteins derived from the antigen of the pathogen or cancer). In preferred embodiments, such antigen-presenting cells are fully or partially HLA-matched antigen presenting cells (relative to the human donor of the population of human blood cells used to generate the population of cells) (e.g., antigen presenting cells derived from the human donor of the population of human blood cells used to generate the population of cells). In specific embodiments, the population of cells comprising antigen-specific T cells generated by a method described in Section 5.1 lyses less than or equal to 15%, 10%, 5%, 2%, or 1% of antigen presenting cells that do not present the one or more antigens (e.g., antigen presenting cells that are not loaded with or genetically engineered to express one or more peptides or proteins derived from the antigen of the pathogen or cancer). In a specific embodiment, the population of cells comprising antigen-specific T cells generated by a method described in Section 5.1 lyses less than or equal to 10% of antigen presenting cells that do not present the one or more antigens (e.g., antigen presenting cells that are not loaded with or genetically engineered to express one or more peptides or proteins derived from the antigen of the pathogen or cancer). In another specific embodiment, the population of cells comprising antigen-specific T cells generated by a method described in Section 5.1 lyses less than or equal to 5% of antigen presenting cells that do not present the one or more antigens (e.g., antigen presenting cells that are not loaded with or genetically engineered to express one or more peptides or proteins derived from the antigen of the pathogen or cancer).

In certain embodiments, the population of cells comprising antigen-specific T cells generated by a method described in Section 5.1 lacks substantial antigen reactivity (for example, cytotoxicity) in vitro toward HLA-mismatched (relative to the human donor of the population of human blood cells used to generate the population of cells) antigen presenting cells. In some embodiments, such antigen-presenting cells present the one or more antigens (e.g., are loaded with or genetically engineered to express one or more peptides or proteins derived from the antigen of the pathogen or cancer). In other embodiments, such antigen-presenting cells do not present the one or more antigens (e.g., are not loaded with or genetically engineered to express one or more peptides or proteins derived from the antigen of the pathogen or cancer). In specific embodiments, the population of cells comprising antigen-specific T cells generated by a method described in Section 5.1 lyses less than or equal to 15%, 10%, 5%, 2%, or 1% of HLA-mismatched (relative to the human donor of the population of human blood cells used to generate the population of cells) antigen presenting cells. In a specific embodiment, the population of cells comprising antigen-specific T cells generated by a method described in Section 5.1 lyses less than or equal to 10% of HLA-mismatched (relative to the human donor of the population of human blood cells used to generate the population of cells) antigen presenting cells. In another specific embodiment, the population of cells comprising antigen-specific T cells generated by a method described in Section 5.1 lyses less than or equal to 5% of HLA-mismatched (relative to the human donor of the population of human blood cells used to generate the population of cells) antigen presenting cells.

In certain embodiments, the population of cells comprising antigen-specific T cells generated by a method described in Section 5.1 lacks substantial antigen reactivity (for example, cytotoxicity) in vitro toward antigen presenting cells that do not present the one or more antigen presenting cells (e.g., antigen presenting cells that are not loaded with or genetically engineered to express one or more peptides or proteins derived from the antigen of the pathogen or cancer), as described above, and lacks substantial antigen reactivity (for example, cytotoxicity) in vitro toward HLA-mismatched antigen presenting cells as described above.

Antigen presenting cells that can be used in the alloreactivity assay include, but are not limited to, dendritic cells, phytohemagglutinin (PHA)-lymphoblasts, macrophages, B-cells that generate antibodies, EBV-BLCL cells, and artificial antigen presenting cells (AAPCs).

5.4.3. HLA Type

The HLA assignment (i.e., the HLA loci type) of a population of cells comprising antigen-specific T cells generated by a method described in Section 5.1, supra, (i.e., the HLA assignment of the antigen-specific T cells contained in the population of cells comprising antigen-specific T cells) and/or the HLA assignment of the diseased cells in the human patient to be treated or envisioned to be treated can be ascertained (i.e., typed) by any method known in the art for typing HLA alleles. The assignment can be performed using the population of cells comprising antigen-specific T cells directly, an aliquot thereof, or a precursor cell population that indicates the HLA assignment of the population of cells comprising antigen-specific T cells. Non-limiting exemplary methods for ascertaining the HLA assignment can be found in ASHI Laboratory Manual, Edition 4.2 (2003), American Society for Histocompatibility and Immunogenetics; ASHI Laboratory Manual, Supplements 1 (2006) and 2 (2007), American Society for Histocompatibility and Immunogenetics; Hurley, "DNA-based typing of HLA for transplantation." in Leffell et al., eds., 1997, Handbook of Human Immunology, Boca Raton: CRC Press; Dunn, 2011, Int J Immunogenet 38:463-473; Erlich, 2012, Tissue Antigens, 80:1-11; Bontadini, 2012, Methods, 56:471-476; and Lange et al., 2014, BMC Genomics 15: 63. In specific embodiments, at least 4 HLA loci (preferably HLA-A, HLA-B, HLA-C, and HLA-DR) are typed. In a specific embodiment, 4 HLA loci (preferably HLA-A, HLA-B, HLA-C, and HLA-DR) are typed. In another specific embodiment, 6 HLA loci are typed. In another specific embodiment, 8 HLA loci are typed. In another specific embodiment, 10 HLA loci are typed.

In general, high-resolution typing is preferable for HLA typing. The high-resolution typing can be performed by any method known in the art, for example, as described in ASHI Laboratory Manual, Edition 4.2 (2003), American Society for Histocompatibility and Immunogenetics; ASHI Laboratory Manual, Supplements 1 (2006) and 2 (2007), American Society for Histocompatibility and Immunogenetics; Flomenberg et al., Blood, 104:1923-1930; Kögler et al., 2005, Bone Marrow Transplant, 36:1033-1041; Lee et al., 2007, Blood 110:4576-4583; Erlich, 2012, Tissue Antigens, 80:1-11; Lank et al., 2012, BMC Genomics 13:378; or Gabriel et al., 2014, Tissue Antigens, 83:65-75.

In specific embodiments, the HLA assignment of the diseased cells in the human patient to be treated or envisioned to be treated is ascertained by typing the origin of the diseased cells (e.g., the human patient or a transplant donor for the human patient, as the case may be). The origin of the diseased cells can be determined by any method known in the art, for example, by analyzing variable tandem repeats (VTRs) (which is a method that uses unique DNA signature of small DNA sequences of different people to distinguish between the recipient and the donor of a transplant), or by looking for the presence or absence of chromosome Y if the donor and the recipient of a transplant are of different sexes (which is done by cytogenetics or by FISH (fluorescence in situ hybridization)).

The HLA allele by which the population of cells comprising antigen-specific T cells generated by a method described in Section 5.1, supra, is restricted (i.e., the HLA allele by which the antigen-specific T cells contained in the population of cells comprising antigen-specific T cells are restricted) can be determined by any method known in the art, for example, as described in Trivedi et al., 2005, Blood 105:2793-2801; Barker et al., 2010, Blood 116:5045-5049; Hasan et al., 2009, J Immunol, 183:2837-2850; Doubrovina et al., 2012, Blood 120:1633-1646; International Patent Application Publication No. WO 2016/073550; or International Patent Application Publication No. WO 2017/044678. The determination can be performed using the population of cells comprising antigen-specific T cells directly, an aliquot thereof, or a precursor cell population that indicates the HLA allele by which the population of cells comprising antigen-specific T cells is restricted (i.e., the HLA allele by which the antigen-specific T cells contained in the population of cells comprising antigen-specific T cells are restricted).

In some embodiments, the antigen-specific T cells contained in the population of cells comprising antigen-specific T cells are restricted by an HLA allele shared with the diseased cells in the human patient to be treated or envisioned to be treated. In other embodiments, the antigen-specific T cells contained in the population of cells comprising antigen-specific T cells share at least 2 HLA alleles (for example, at least 2 out of 10 HLA alleles, or at least 2 out of 8 HLA alleles (such as two HLA-A alleles, two HLA-B alleles, two HLA-C alleles, and two HLA-DR alleles)) with the diseased cells in the human patient to be treated or envisioned to be treated. In other embodiments, the antigen-specific T cells contained in the population of cells comprising antigen-specific T cells are restricted by an HLA allele shared with diseased cells in the human patient to be treated, and share at least 2 HLA alleles (for example, at least 2 out of 10 HLA alleles, or at least 2 out of 8 HLA alleles (such as two HLA-A alleles, two HLA-B alleles, two HLA-C alleles, and two HLA-DR alleles)) with the diseased cells in the human patient to be treated or envisioned to be treated.

5.5. Composition and Kits

In another aspect, provided herein are pharmaceutical compositions comprising a therapeutically effective amount of an isolated population of cells comprising antigen-specific T cells described herein, and a pharmaceutically acceptable carrier. In a preferred embodiment, the pharmaceutical composition is in a cryopreserved form.

The pharmaceutical acceptable carrier can be any physiologically-acceptable solution suitable for the storage and/or therapeutic administration of T cells, for example, a saline solution, a buffered saline solution, or a bio-compatible solution comprising one or more cryopreservatives (e.g., phosphate-buffered saline containing 7% DMSO, 5% dextrose and 1% dextran; hypothermosol containing 5% DMSO and 5% human serum albumin; normal saline containing 10% DMSO and 16% human serum albumin; or normal saline containing 10% DMSO and 15% human serum albumin).

The population of cells comprising antigen-specific T cells can be stored in the pharmaceutical composition at any concentration desirable for its long-term storage and convenience of storage and handling. In a specific embodiment, the population of cells comprising antigen-specific T cells is stored in the pharmaceutical composition at a concentration of about $5 \times 10^6$ cells/ml. In another specific embodiment, the population of cells comprising antigen-specific T cells is stored in the pharmaceutical composition at a concentration of about $10 \times 10^6$ cells/ml. In another specific embodiment, the population of cells comprising antigen-specific T cells is stored in the pharmaceutical composition at a concentration of about $20 \times 10^6$ cells/ml. In another specific embodiment, the population of cells comprising antigen-specific T cells is stored in the pharmaceutical composition at a concentration of about $50 \times 10^6$ cells/ml. In another specific embodiment, the population of cells comprising antigen-specific T cells is stored in the pharmaceutical composition at a concentration of about $100 \times 10^6$ cells/ml. In another specific embodiment, the population of cells comprising antigen-specific T cells is stored in the pharmaceutical composition at a concentration of about $200 \times 10^6$ cells/ml. In another specific embodiment, the population of cells comprising antigen-specific T cells is stored in the pharmaceutical composition at a concentration of about $500 \times 10^6$ cells/ml. In another specific embodiment, the population of cells comprising antigen-specific T cells is stored in the pharmaceutical composition at a concentration of about 1 to $10 \times 10^6$ cells/ml. In another specific embodiment, the population of cells comprising antigen-specific T cells is stored in the pharmaceutical composition at a concentration of about 10 to $100 \times 10^6$ cells/ml. In another specific embodiment, the population of cells comprising antigen-specific T cells is stored in the pharmaceutical composition at a concentration of about 100 to $1000 \times 10^6$ cells/ml.

Also provided herein are kits comprising in one or more containers the pharmaceutical composition described herein. In specific embodiments, the kits further comprise a second pharmaceutical composition comprising a second compound or biological product for treating the pathogen infection or cancer.

Optionally associated with such one or more containers can be a notice in the form prescribed by a governmental agency regulating the manufacture, use or sale of pharmaceuticals or biological products, which notice reflects approval by the agency of manufacture, use or sale for human administration.

The pharmaceutical compositions and kits encompassed herein can be used in accordance with the methods of treating a human patient as provided in this disclosure.

As stated above, the term "about" shall be construed so as to allow normal variation, such as, for example, a variation within 20%.

5.6. Cell Culture Systems

In another aspect, the present invention provides a cell culture system (including, but not limited to, a cell culture flask, cell culture dish, or cell culture plate) that comprises: (a) a population of human blood cells comprising human T cells; (b) antigen presenting cells presenting one or more antigens of a human pathogen or human cancer; and (c) soluble IL-15/IL-15Rα complexes; said cell culture system lacking cells recombinantly expressing soluble IL-15/IL-15Rα complexes. In a preferred embodiment, the cell culture system further comprises cell culture medium contacting the population of human blood cells, antigen presenting cells, and soluble IL-15/IL-15Rα complexes. In a specific embodiment, the human T cells, antigen-presenting cells, and soluble IL-15/IL-15Rα complexes are present in amounts conducive to sensitization of the human T cells to the one or more antigens. In a specific embodiment, the cell culture system is subjected to, or is present in, culture conditions conducive to T cell survival, expansion, and sensitization. Such cell culture conditions are well known in the art.

In another aspect, the present invention provides a cell culture system (including, but not limited to, a cell culture flask, cell culture dish, or cell culture plate) that comprises: (a) a population of human blood cells comprising human antigen-specific T cells; (b) antigen presenting cells presenting one or more antigens of a human pathogen or human cancer; and (c) soluble IL-15/IL-15Rα complexes; said cell culture system lacking cells recombinantly expressing soluble IL-15/IL-15Rα complexes. In a preferred embodiment, the cell culture system further comprises cell culture medium contacting the population of human blood cells, antigen presenting cells, and soluble IL-15/IL-15Rα complexes. In a specific embodiment, the cell culture system is subjected to, or is present in, culture conditions conducive to T cell survival and expansion. Such cell culture conditions are well known in the art.

The population of human blood cells, human T cells, human antigen-specific T cells, antigen-presenting cells, soluble IL-15/IL-15Rα complexes, etc., can be as described in this disclosure.

5.7. Antigen Specificity and Patients

The antigen of a pathogen or cancer described herein is an antigen of a human pathogen or human cancer. It can be a peptide or protein whose expression is higher in diseased cells (for example, cells infected by the pathogen, or cancerous cells) relative to non-diseased cells (for example, cells not infected by the pathogen, or non-cancerous cells), or a peptide or protein that is uniquely expressed in diseased cells (for example, cells infected by the pathogen, or cancerous cells) relative to non-diseased cells (for example, cells not infected by the pathogen, or non-cancerous cells).

In some embodiments, the one or more antigens is one or more antigens of a pathogen. In specific embodiments, the human patient to be treated or envisioned to be treated has the pathogen. The pathogen can be a virus, bacterium, fungus, helminth or protist.

In specific embodiments, the pathogen is a virus. In a specific embodiment, the virus is cytomegalovirus (CMV). In an aspect of the specific embodiment, the one or more antigens of CMV is CMV pp65 and/or CMV IE1. In another aspect of the specific embodiment, the one or more antigens of CMV is CMV pp65. In another specific embodiment, the virus is Epstein-Barr virus (EBV). In an aspect of the specific embodiment, the one or more antigens of EBV is EBNA1, EBNA2, EBNA3A, EBNA3B, EBNA3C, LMP1, and/or LMP2. In another aspect of the specific embodiment, the one or more antigens of EBV is EBNA1, LMP1, and/or LMP2. In another specific embodiment, the virus is BK virus (BKV), John Cunningham virus (JCV), herpesvirus (such as human herpesvirus-6 or human herpesvirus-8), human papillomavirus (HPV), hepatitis B virus (HBV), hepatitis C virus (HCV), herpes simplex virus (HSV), varicella zoster virus (VZV), Merkel cell polyomavirus (MCV), adenovirus (ADV), human immunodeficiency virus (HIV), influenza virus, ebola virus, poxvirus, rhabdovirus, or paramyxovirus.

In specific embodiments, the pathogen is a bacterium, such as a mycobacterium or *Chlamydia trachomatis*. In specific embodiments, the pathogen is a fungus, such as *Cryptococcus neoformans, Pneumocystis jiroveci*, a *Candida*, or an invasive fungus. In specific embodiments, the pathogen is a helminth. In specific embodiments, the pathogen is a protist, such as *Toxoplasma gondii*. In specific embodiments, the pathogen is a protozoon.

In specific embodiments, the human patient has an infection with the pathogen. In a specific embodiment, the pathogen is CMV and the human patient has a CMV infection (e.g., CMV viremia, CMV retinitis, CMV pneumonia, CMV hepatitis, CMV colitis, CMV encephalitis, CMV meningoencephalitis, CMV-positive meningioma, or CMV-positive glioblastoma multiforme). In another specific embodiment, the pathogen is EBV and the human patient has an EBV-positive lymphoproliferative disorder (EBV-LPD) (for example, an EBV-positive post-transplant lymphoproliferative disorder) resulting from EBV infection, such as B-cell hyperplasia, lymphoma (such as, B-cell lymphoma, non-Hodgkin lymphoma (e.g., diffuse large B-cell lymphoma, for example in the elderly), T cell lymphoma, EBV-positive Hodgkin's lymphoma, Burkitt lymphoma), polymorphic or monomorphic EBV-LPD, autoimmune lymphoproliferative syndrome, or mixed PTLD (post-transplant lymphoproliferative disorder). In another specific embodiment, the pathogen is EBV and the human patient has an EBV-positive nasopharyngeal carcinoma. In another specific embodiment, the pathogen is EBV and the human patient has an EBV-positive gastric cancer. In another specific embodiment, the pathogen is EBV and the human patient has an EBV-positive leiomyosarcoma. In another specific embodiment, the pathogen is EBV and the human patient has an EBV-positive NK/T lymphoma. In another specific embodiment, the pathogen is EBV and the human patient has an EBV viremia.

In other embodiments, the one or more antigens is one or more antigens of a cancer. In specific embodiments, the human patient to be treated or envisioned to be treated has the cancer.

The cancer can be a blood cancer, such as, but is not limited to: acute lymphoblastic leukemia, chronic lymphocytic leukemia, acute myelogenous leukemia, chronic myelogenous leukemia, hairy cell leukemia, T cell prolymphocytic leukemia, Large granular lymphocytic leukemia, adult T cell leukemia, plasma cell leukemia, Hodgkin lymphoma, Non-Hodgkin lymphoma, or multiple myeloma. In a specific embodiment, the cancer is multiple myeloma or plasma cell leukemia.

The cancer can also be a solid tumor cancer, including, but is not limited to, a sarcoma, a carcinoma, a lymphoma, a germ cell tumor, or a blastoma. The solid tumor cancer that can be, such as, but is not limited to: a cancer of the breast, lung, ovary, stomach, pancreas, larynx, esophagus, testes, liver, parotid, biliary tract, colon, rectum, cervix, uterus, endometrium, kidney, bladder, prostate, thyroid, brain, or skin.

In certain embodiments, the one or more antigens is Wilms Tumor 1 (WT1). In a specific aspect of the certain embodiments, the cancer is multiple myeloma or plasma cell leukemia.

In a specific embodiment, the human patient is an adult (at least age 16). In another specific embodiment, the human patient is an adolescent (age 12-15). In another specific embodiment, the patient is a child (under age 12).

In a specific embodiment, the human patient has failed a previous therapy for the pathogen or cancer, which previous therapy is not treatment with a population of cells comprising antigen-specific T cells according to the invention, due to resistance to or intolerance of the previous therapy. A disease is considered resistant to a therapy, if it has no response, or has an incomplete response (a response that is less than a complete remission), or progresses, or relapses after the therapy. The previous therapy could be an antiviral agent known in the art (e.g., an antiviral drug or antibody), or an anti-cancer therapy known in the art (e.g., a chemotherapy or a radiotherapy), as the case may be.

6. EXAMPLE

Certain embodiments provided herein are illustrated by the following non-limiting example, which is described in Hasan et al., 2016, Clinical and Experimental Immunology 186:249-265 (first published in a manuscript form online on May 26, 2016 and later published in a print form online on Aug. 31, 2016 and in paper form in November 2016) and which demonstrates that soluble IL-15/IL15Rα complexes augment the expansion of antigen-specific T cells in vitro.

6.1. Summary

As described herein, the soluble and membrane bound forms of 15Rα/15 were examined in a series of in vitro experiments to determine the most functionally active form of 15Rα/15 that supports expansion of human antigen-specific T cells. A cell based AAPC system expressing human 15Rα/15, which permitted a controlled evaluation of soluble and membrane bound 15Rα/15 in comparison to sIL-15, was developed and employed. Genetically modified NIH 3T3 based HLA A2$^+$ AAPC (A2-AAPC) cell lines (Hasan et al., 2009, J Immunol 183:2837-2850) as well as a third party murine pro-B cell line Baf-3 (Rodriguez-Tarduchy et al., 1990, EMBO J 9:2997-3002) were transduced to co-express either human IL-15Rα alone or IL-15Rα in complex with IL-15 (A2-AAPC$^{15R\alpha}$, A2-AAPC$^{15R\alpha/15}$ and Baf-3$^{15R\alpha/15}$).

These studies established that co-expression of IL-15Rα and IL-15 is essential for stable expression of 15Rα/15. Using cell lines transduced to co-express IL-15Rα and IL-15, the differential effects of soluble versus membrane bound 15Rα/15 were examined in comparison to sIL-15 in stimulating the in vitro expansion of memory phenotype epitope-specific T cells in response to a viral antigen such as CMVpp65. This study demonstrated that both soluble and secreted 15Rα/15 complexes can sustain the expansion of antigen-specific central memory T cells ($T_{CM}$ cells), more efficiently than soluble cytokine supplementation with IL-15 or IL-7. These data underscore the advantage of 15Rα/15 in stimulating the expansion of highly functional antigen-specific $T_{CM}$ cells for adoptive immunotherapy applications. Such complexes could be harnessed for appropriate immunotherapy applications in conjunction with cell, vaccine or other immunomodulating agents.

6.2. Materials and Methods

6.2.1. Donors

Blood was collected from six HLA A 02:01 positive healthy, CMV seropositive, volunteer donors consenting to approved protocols by the Institutional Review Board at Memorial Sloan-Kettering Cancer Center (MSKCC) after high resolution HLA typing (HLA Laboratory—MSKCC).

6.2.2. Generation of AAPC and Baf-3 Cells Co-Expressing IL-15Rα and IL-15

Cloned plasmids encoding IL-15 and IL-15Rα genes and containing the CD8 leader sequence, were inserted into SFG retroviral vectors at HindIII and BamHI sites and sequentially transduced into A2-AAPC (Latouche and Sadelain, 2000, Nat Biotechnol 18:405-409). The Kozak sequence (GCCGCCACC) inserted prior to the AUG initiator codon ensured enhanced expression of the transduced gene (Kozak, 1987, J Mol Biol 196:947-950). IL-15Rα transduced cells (A2-AAPC$^{15R\alpha}$) were isolated by FACS and stored (anti-IL-15Rα FITC-BD Biosciences). Some aliquots of A2-AAPC$^{15R\alpha}$ cells were then transduced with IL-15, and cells expressing both IL-15Rα and IL-15 were cloned out by serial dilution. High expressing clones were further isolated by FACS (anti-IL-15 PE and anti-IL-15Rα FITC, BD Biosciences), expanded in Dulbecco's Modified Eagle Medium (DMEM; Invitrogen Inc., Carlsbad, CA)+10% heat inactivated defined calf serum (DCS; Hyclone, Logan, UT) and stored in aliquots for T cell sensitization (A2-AAPC$^{15R\alpha/15}$). Similarly, the mouse pro-B cell line Baf-3 (Rodriguez-Tarduchy et al., 1990, EMBO J 9:2997-3002), passaged in RPMI 1640 with 10% fetal calf serum (FCS) (Life Technologies, Grand Island, NY, USA), was sequentially transduced with retroviral vectors containing the plasmid DNA for IL-15Rα and IL-15 genes (Baf-3$^{15R\alpha/15}$), and irradiated aliquots were used in T cell cultures (FIG. 1).

6.2.3. Generation of CMV-CTLs

T cells were enriched from Ficoll Hypaque separated PBMC (Accurate Chemical & Scientific Corporation, Westbury, NY, USA) using immunomagnetic beads (Pan T-Cell Isolation Kit II, Miltenyi Biotec Inc, Auburn, CA USA) (Hasan et al., 2009, J Immunol 183:2837-2850). CMV-CTLs were then generated as previously described (Hasan et al., 2009, J Immunol 183:2837-2850) using A2-AAPC at a stimulator to effector ratio of 1:10 in AIM-V medium in 8 different conditions: (1) A2-AAPC+sIL-2, (2) A2-AAPC+ sIL-15, (3) A2-AAPC+sIL-2+sIL-15, (4) A2-AAPC+sIL-7+ sIL-4, (5) A2-AAPC$^{15R\alpha}$+sIL-2, (6) A2-AAPC$^{15R\alpha}$+sIL-15, (7) A2-AAPC$^{15R\alpha/15}$, and (8) A2-AAPC+Baf-$^{15R\alpha/15}$. T cells were re-stimulated every 10 days. T cells were supplemented with IL-2 (20 U/ml) and or IL-15 (10 ng/ml) or IL7 (10 ng/ml)+IL4 (1,666 U/ml) (R&D Systems, Inc., Minneapolis, MN) based on the assigned groups. Cytokines were first supplemented on day 8 and then three times per week. Group (8) received 1×10$^6$ irradiated Baf-3$^{15R\alpha/15}$ cells at each re-stimulation, and group (7) was restimulated with A2-AAPC$^{15R\alpha/15}$ every 10 days without additional soluble cytokine supplementation.

6.2.4. Transwell T Cell Cultures

Parallel T cell co-cultures were set up from 3 HLA-A0201$^+$ donors with irradiated A2-AAPCs in trans-well tissue culture plates consisting of two chambers in each well separated by a 3 μm permeable membrane (Corning Costar #3414). The permeable membrane in each well allowed the passage of soluble cytokines as well as secreted soluble 15Rα/15, while separating the T cell co-cultures from cell surface expressed 15Rα/15. In parallel co-cultures, T cells stimulated with A2-AAPCs were supplemented with (1) irradiated Baf-3$^{15R\alpha/15}$ cells (10$^6$/ml), (2) irradiated A2-AAPC$^{15R\alpha/15}$ (10$^6$/ml), (3) sIL-15 (10 ng/ml), or (4) sIL-2 (20 units/ml). Soluble cytokines were added at day 8 and then thrice a week, and irradiated Baf-3$^{15R\alpha/15}$ or A2AAPC$^{15R\alpha/15}$ were replenished every 10 days.

6.2.5. Epstein-Barr Virus (EBV)-B Lymphoblastoid Cell Lines (BLCLs)

Autologous EBV-BLCLs were generated for each donor as previously described (Koehne et al., 2002, Blood 99:1730-1740). The cells were maintained in RPMI 1640+ 10% FCS (Life Technologies, Grand Island, NY, USA).

6.2.6. CMV pp65 Peptides

The HLA A 02:01 presented nonamer NLVPMVATV (NLV) within CMVpp65 was synthesized by the microchemistry and proteomics core facility at MSKCC, stored in small aliquots (2.4 μg/10 μl) and used to assess the responses in functional T cell assays.

6.2.7. Isolation and Quantitation of IL-15, IL-15Rα and 15Rα/15 Complexes

IL-15 in all samples was quantitated by Human IL-15 Quantikine ELISA Kit (R&D Systems, Inc., Minneapolis, MN). Concentrated (3 kDa filtration units, Millipore Corp., Billerica, MA) serum free cell supernatants (RPMI 1640) were fractionated into 1 ml fractions running over a Superdex 200 10/30 column at 0.5 ml/min in 20 mM TRIS, 50 mM NaCl, pH 8.0 buffer using a classic FPLC system (GE Healthcare Bio-Sciences Corp., Piscataway, NJ). BSA (66.4 kDa) and lysozyme (4.3 kDa) (1 mg/ml, Sigma-Aldrich, USA), served as MW markers (confirmed by Bradford protein assay and gel electrophoresis with Coomassie staining). FPLC fractions were analyzed for IL-15. Baf-3$^{15R\alpha/15}$ supernatants were subjected to 12.5% SDS-PAGE to distinguish free IL-15 from 15Rα/15. Heat denatured, reduced and non-reduced supernatants were then analyzed by Western blot using anti-human IL-15 Rα and IL-15 antibodies (R&D Systems, Inc., Minneapolis, MN).

6.2.8. Phenotypical Analysis of CMV-CTLs

Quantitation of Tetramer+ CD8+ CMV-CTLs

HLA A 02:01-NLV MHC-peptide tetramers (MSKCC tetramer core) were used to quantitate CMVpp65 NLV responsive T cells at days 0, 7, 14, 21 and 28 in culture as described previously (Hasan et al., 2009, J Immunol 183: 2837-2850). HLA A 24:02-QYDPVAALF and HLA B 07:02 TPRVTGGGAM peptide-MHC tetramers (MSKCC tetramer core) were used as controls.
Memory Phenotype of Tetramer+ T Cells T cells were incubated with anti-CD8 PerCP, APC labelled Tetrameric MHC-peptide complexes, anti-CD62L FITC, anti-CD45RA PE and anti-CCR7 Pe-Cy7. CD8+ and Tet+ T cells were analyzed to determine the proportion of CD45RA− CD62L+ or CCR7+ (central memory T cells ($T_{CM}$)) or CD45RA− CD62L+ or CCR7− (effector memory T cells ($T_{EM}$)). All antibodies for FACS analysis were purchased from BD biosciences.

6.2.9. Cell Proliferation and Apoptosis

Carboxyfluorescein Diacetate Succinimidyl Ester (CFSE) Dilution Assay

Day 14 stimulated T cells were resuspended in PBS/0.1% BSA at $10^7$ cells/ml, and incubated with a 5 mM DMSO stock solution of CFSE (Invitrogen Grand Island, NY) to achieve a final concentration of 10 μM CFSE for 10 min at 37° C. Labelled T cells were washed with 5 volume ice-cold RPMI 1640/10% FBS, incubated on ice×5 min for quenching, then washed ×3 in T cell medium (AIM V+5% DCS). Aliquots of 1-2×$10^6$/ml CFSE labelled T cells were then co-cultured with irradiated A2 AAPC in separate 6 well plates supplemented with the same cytokines as prior stimulation: sIL-2 (20 U/ml), sIL-15 (10 ng/ml), sIL-7 (10 ng/ml)+sIL-4 (1666 U/ml), 1×$10^6$ irradiated Baf-3$^{15R\alpha/15}$, or with irradiated A2-AAPC$^{15R\alpha/15}$. Primary T cells stimulated with CD3-CD28 beads at a 1:1 ratio+50 U/ml sIL-2 served as positive control. CFSE labelled T cells were then stained with CD3, CD8 and A2-NLV tetramer and analyzed by FACS at 2 and 7 days in culture after CFSE labeling.

6.2.10. Apoptosis Assay

Non-viable T cells in the different culture conditions were assessed by FACS using the dead cell stain 7AAD. Epitope specific A2-NLV tetramer+ T cells labelled with 7AAD were quantitated.

6.2.11. Functional Analysis of CMV-CTLs

Th1 Cytokine Generation

T cell responses to the nonamer peptide NLVPMVATV (NLV) were evaluated by quantitating IFNγ+ CD8+ T cells upon secondary stimulation with peptide loaded autologous APCs (PBMC or BLCL) as previously described (Koehne et al., 2002, Blood 99:1730-1740; Waldrop et al., 1997, J Clin Invest 99:1739-1750). Autologous APCs loaded with serial dilutions of NLV peptide (10 nM to 0.1 pM) were also used to elicit differential T cell responses.
Intracellular Granzyme B NLV peptide loaded autologous BLCL were co-incubated with CMV-CTLs for 4-6 hours at a 5:1 responder to stimulator ratio in the presence of brefeldin A. Fluorescent antibody labeled T cells (anti-CD3, CD4, CD8—BD biosciences) were fixed, then permeabilized (BD biosciences fix and perm kit) and labeled with anti-human granzyme B antibody (GB 11, eBiosciences, CA, USA) and analyzed by FACS.
In Vitro Cytotoxicity T cell cytotoxic activity was evaluated in a standard in vitro $^{51}$Cr release assay (Koehne et al., 2002, Blood 99:1730-1740). T cell targets included: autologous EBV-BLCLs (1) loaded with titrated concentrations of the NLV peptide (2.4 μg-2.4 ng/$10^6$ EBV-BLCLs), (2) loaded with 2.4 μg/$10^6$ EBV-BLCLs at progressively diminishing E:T ratios, (3) NLV peptide loaded HLA mismatched EBV-BLCL and (4) BLCL lines without peptide. (3) and (4) served as controls.

6.2.12. Statistics

The Wilcoxon rank sum test was used to compare groups.

6.3. Results

Figure 2A:
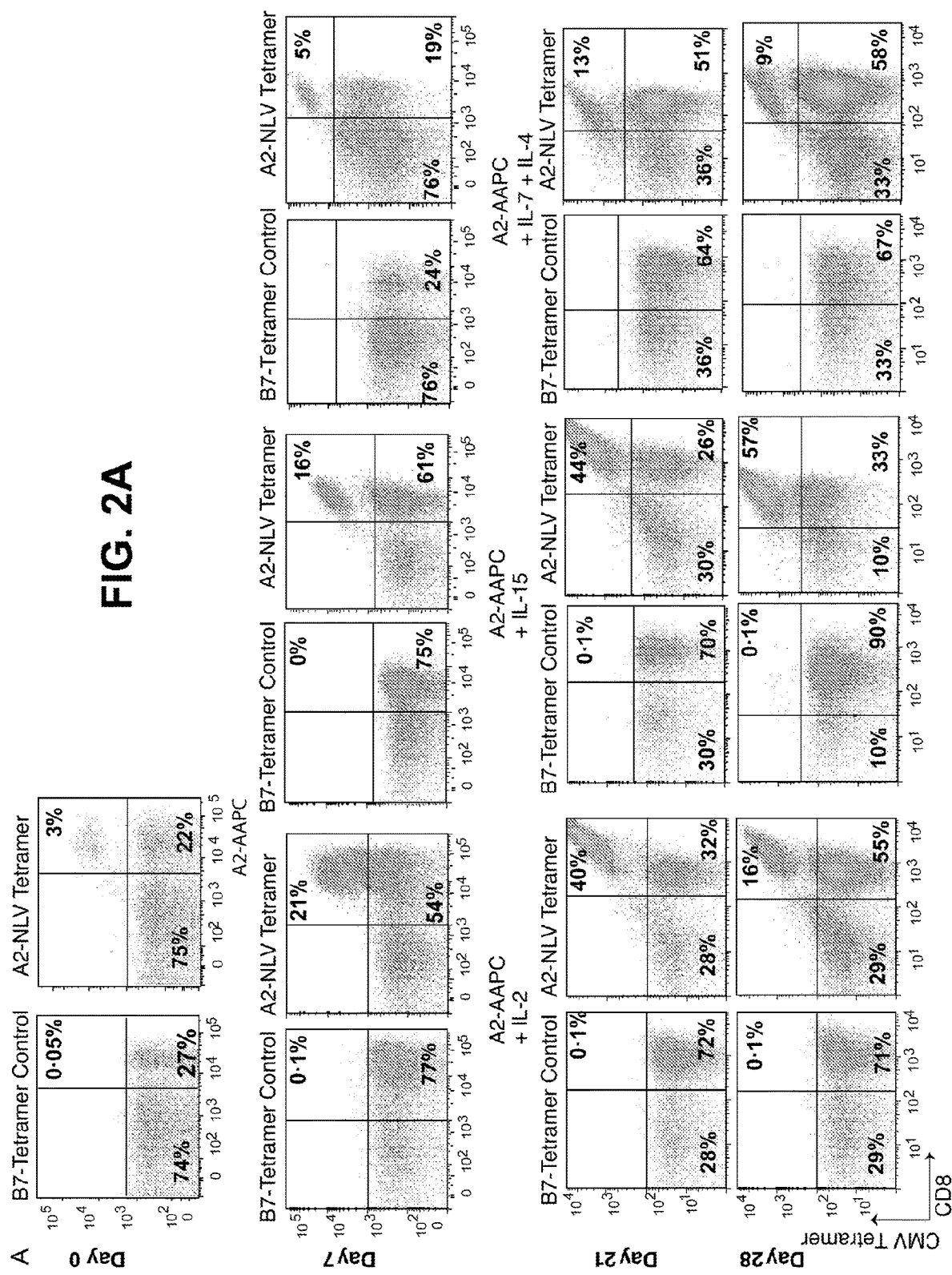
Figures 2B, 2C, 2D:
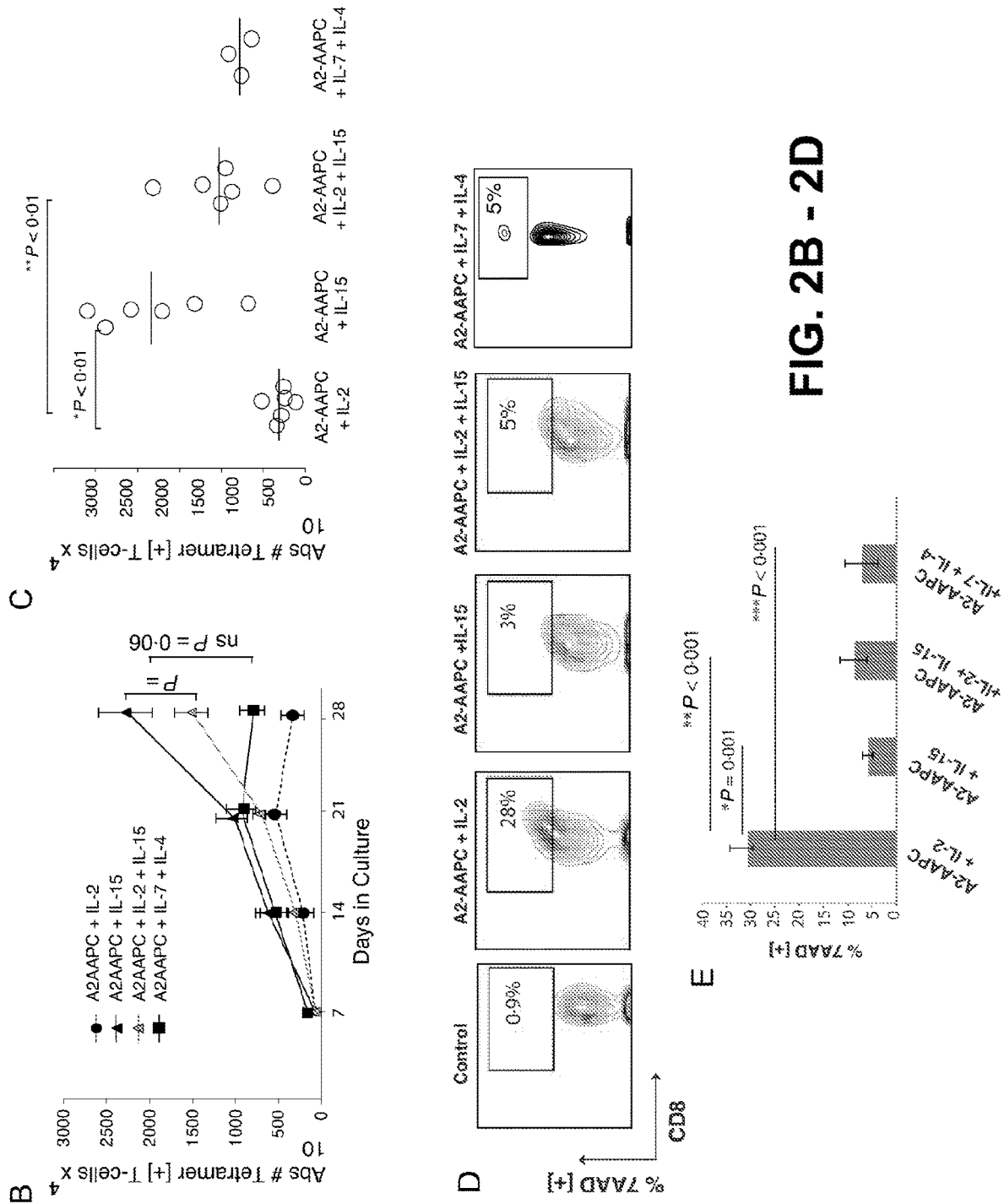

6.3.1. Soluble IL-15 Augments Expansion of CMV-CTLs In Vitro and Prevents T Cell Apoptosis The goal of this study was to develop strategies for robust in vitro expansion of antigen-specific T cells. Initially, the effects of the pro-survival cytokine IL-15 were compared in comparison to IL-2 on the enrichment and overall expansion of CMVpp65 specific T cells in an AAPC model system. This panel of HLA class-I expressing AAPCs is specifically designed for the expansion of CD8+ CMV-CTLs responding to HLA class-I presented epitopes (Hasan et al., 2009, J Immunol 183:2837-2850). To generate CMV-CTLs, T cells from 6 healthy CMV seropositive HLA A02:01+ donors were stimulated using A2-AAPC and supplemented with either sIL-2 (20 u/ml) or sIL-15 (10 ng/ml). With this approach, CTLs supplemented with sIL-15 demonstrated a steady enrichment through 28 days of epitope specific T cells responding to the HLA A02:01 presented NLV epitope in MHC-peptide tetramer binding assays. Strikingly, sIL-15 supplementation maintained a high proportion of Tet+ T cells even beyond 21 days of continuous antigenic stimulation (FIG. 2A shows one representative example). In comparison, the enrichment of Tet+ T cells in sIL-2 supplemented CMV-CTLs peaked at 21 days, after which Tet+ T cells underwent an attrition in both proportion and numbers between 21 and 28 days (FIG. 2B). As a result, sIL-15 generated a significantly higher overall yield of Tet+ T cells with a median of 1.8×$10^7$ compared to 3.4×$10^6$ Tet+ T cells in sIL-2 CTLs (p<0.01) (FIG. 2B, C), providing a median fold expansion of 900 vs. 375 (Table 1). This also correlated with proportionately lower numbers of 7AAD+ apoptotic T cells observed in sIL-15 CTLs compared to sIL-2 CTLs (3%-5% and 24%-32% respectively) (p<0.001) (FIG. 2D). Simultaneously, combinations of γ chain cytokines were examined for their effect on overall yields of Tet+ T cells. When sIL-15 was supplemented together with sIL-2, an augmented yield of Tet+ T cell was achieved at 28 days in comparison to sIL-2 CTLs, but the yield remained below that obtained with sIL-15 alone (median=1×$10^7$ and 1.8×$10^7$, respectively, or 550 vs. 900-fold expansion with sIL-15 alone) (p<0.01) (FIG. 2B, 2C). Then, sIL-7+sIL-4 was also examined in 3 separate T cell donors based on previously reported T cell expansion in short term in vitro cultures (Gerdemann et al., 2012, Mol Ther 20:1622-1632). As shown in FIG. 2A, although this combination led to an excellent overall T cell expansion, CTLs expanded in the presence of sIL-7 and sIL-4 contained a sizable proportion of CD4+ T cells (38%-51%). Importantly, enrichment of Tet+ T cells was achieved in these cultures within the first 15-21 days that then reached a plateau between 21 and 28 days. This resulted in an overall higher yield of Tet+ T cells with sIL-7+sIL-4 than in sIL-2 supplemented CTLs, but also remained lower than in sIL-15-only CTLs in the AAPC system which fosters expansion of CD8+ T cells (FIG. 2B, C). The proportion of apoptotic T cells in sIL-7+sIL-4 cultures was low as with sIL-15 supplemented CTLs (FIG. 2D, E). Overall, in this in vitro system, supplementation with sIL-15 demonstrated the most robust CTL expansion.

reasons for lower IL-15 concentrations detected in A2-AAPC$^{15R\alpha}$ cells, time sequence studies quantitating cell surface expressed IL-15 were performed and it was observed that all detectable IL-15 was intracellular, suggesting that A2-AAPC$^{15R\alpha}$ cells rapidly bound and internalized the supplemented sIL-15 from the cell medium, without recycling for surface presentation (data not shown). The inferior T cell expansion in A2-AAPC$^{15R\alpha}$ co-cultures was therefore ascribed to the non-availability of IL-15 due to intracellular sequestration within these AAPCs. Although in other systems, IL-15Rα expressing cells loaded with sIL-15 have demonstrated surface expression of 15Rα/15 complexes (Tamzalit et al., 2014, Proc Natl Acad Sci USA 111:8565-8570), these data suggested that, in this system, both IL-15

TABLE 1

Summary of in vitro analysis of T cells cultured under different cytokine conditions.

| Culture Condition | Fold Expansion Tet[+] CD8[+] | Fold Expansion Tet[+] CD62L[+] CD8[+] | IFNγ[+] CD8[10$^6$] NLV nM | IFNγ[+] CD8[10$^6$] NLV 0.1 pM | % In Vitro Cytotoxicity E:T = 1:1 | % In Vitro Cytotoxicity E:T = 1:10 |
|---|---|---|---|---|---|---|
| A2-AAPC + IL-2 | 200-600 | 0 | 1-2 | 0 | 12-21 | 0 |
| A2-AAPC + IL-15 | 300-1300 | 3-5 | 2-4 | <1-2 | 15-23 | 0 |
| A2-AAPC + IL-2 + IL-15 | 250-750 | 0 | 1-3 | <1 | 11-19 | 0 |
| A2-AAPC + IL-7 + IL-4 | 330-675 | 7-11 | 1-4 | 1-2 | 17-21 | 3 |
| A2-AAPC$^{IL-15R\alpha}$ + IL-2 | 25-100 | 0 | <1-2 | 0 | 8-14 | 0 |
| A2-AAPC$^{IL-15R\alpha}$ + IL-15 | 100-300 | 7-10 | 1-4 | 1-2 | 13-24 | 3-5 |
| A2-AAPC$^{IL-15R\alpha/IL-15}$ | 1200-2300 | 600-1000 | 10-16 | 7-12 | 52-73 | 12-20 |
| A2-AAPC + Baf-3$^{IL-15R\alpha/IL-15}$ | 1100-1600 | 550-700 | 10-14 | 7-10 | 40-60 | 16-25 |

A2-AAPC = A2-artificial antigen-presenting cells; IFN = interferon; IL = interleukin.

Figure 3A:
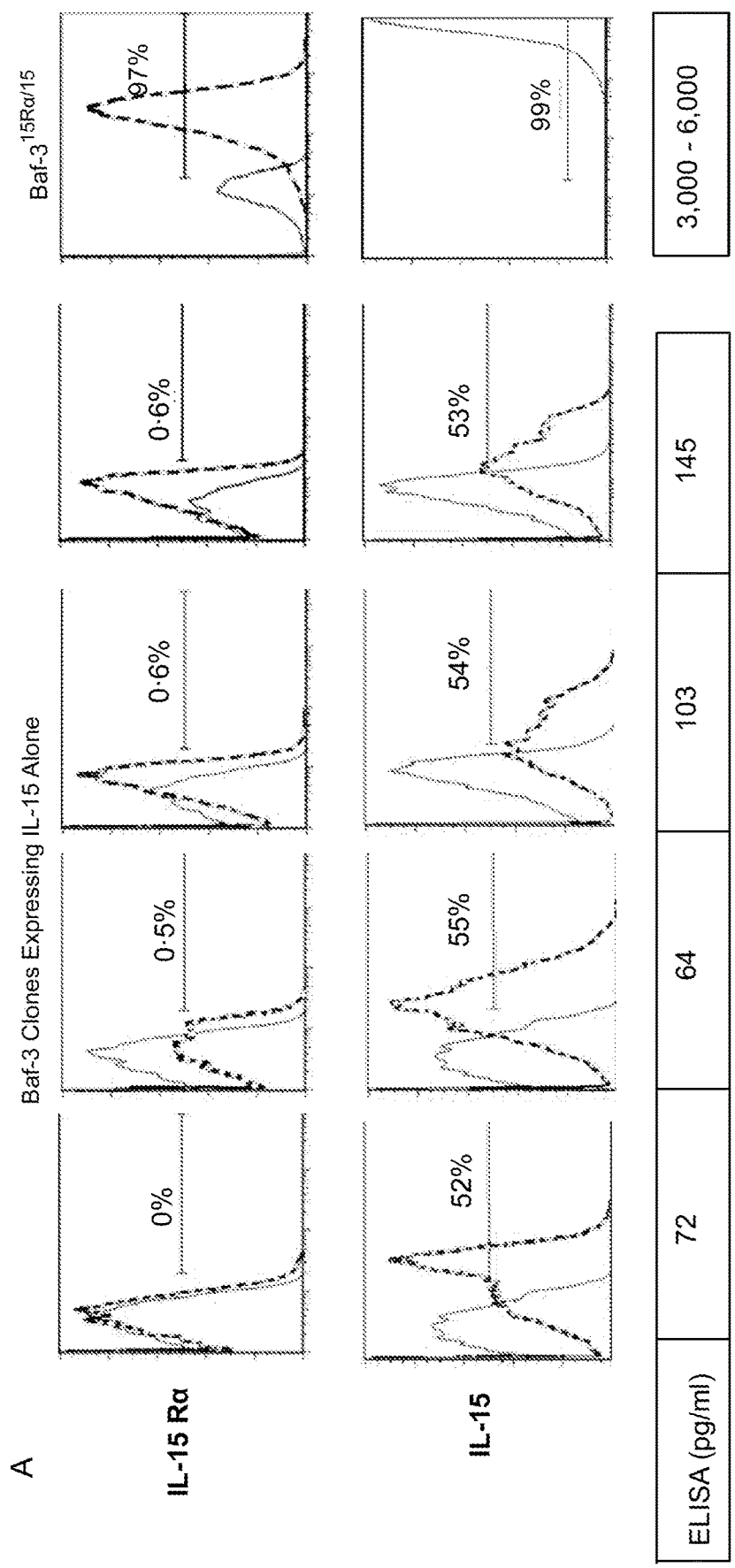

6.3.2. Generation of an AAPC System Providing IL-15Rα/IL-15 Complex for Robust Expansion of Antigen Specific T Cells Requires Both IL-15 and IL-15Rα Genes The study presented in this example sought to develop an off-the-shelf APC system providing both IL-15 and IL-15Rα for in vitro expansion of antigen-specific T cells as a strategy to provide potentially superior and more physiological T cell stimulation. The requisite in vitro conditions for the formation and cell surface expression of 15Rα/15 were initially examined. A2AAPC as well as Baf-3 cells were transduced with the IL-15 gene alone and the expression and secretion of IL-15 were evaluated. In several independent experiments, IL-15 transduced cells lost expression after a few in vitro passages, and minimal amounts of IL-15 (64-145 pg/ml) were detected in the supernatants of these cells by ELISA (FIG. 3A). This suggested that the IL-15 gene is unstable when transduced alone, and requires IL-15Rα to form a stable complex. Thereafter, A2 AAPC transduced with IL-15Rα alone (A2-AAPC$^{15R\alpha}$) were generated, which demonstrated stable expression of IL-15Rα. These cells were then loaded with saturating doses of sIL-15 (10-50 ng/ml) to evaluate the expression of 15Rα/15 and secretion of IL-15. Surprisingly, sIL-15 loaded A2-AAPC$^{15R\alpha}$ cells also demonstrated a markedly lower level of immunologically detectable IL-15 (94-270 pg/ml IL-15) in comparison to A2-AAPC supernatants supplemented with the same concentrations of sIL-15 (6000 to 10,000 pg/ml) (FIG. 3B), and did not express 15Rα/15 on the cell surface. In T cell co-cultures, sIL-15 loaded A2-AAPC$^{15R\alpha}$ elicited a lower yield of epitope specific Tet+ T cell numbers compared to sIL-15 supplemented A2-AAPC (FIG. 3C). To elucidate and IL-15Rα genes would be required within the same cell for secretion of IL-15 and stable expression of 15Rα/15 complexes. Accordingly, AAPCs transduced to express both IL-15 and IL-15Rα genes (A2-AAPC$^{15R\alpha/15}$) were generated. These cells demonstrated high expression levels of 15Rα/15 complex on the cell surface (FIG. 1) and also secreted detectable quantities of IL-15 by ELISA (3000-6000 pg/ml of IL-15) (FIG. 3A).

6.3.3. IL-15 Detected in the Supernatants of A2-AAPC$^{15R\alpha/15}$, Baf-3$^{15R\alpha/15}$ and A2-AAPC$^{15R\alpha}$ is Predominantly Bound to IL-15Rα

Figure 4A:
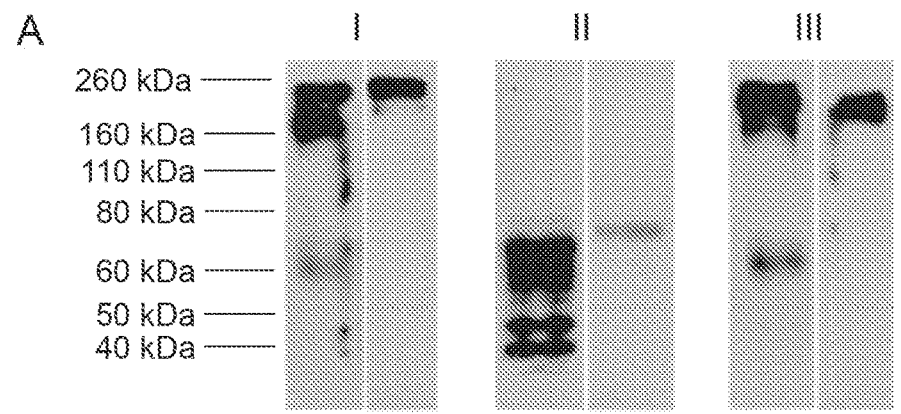
Figure 4B:
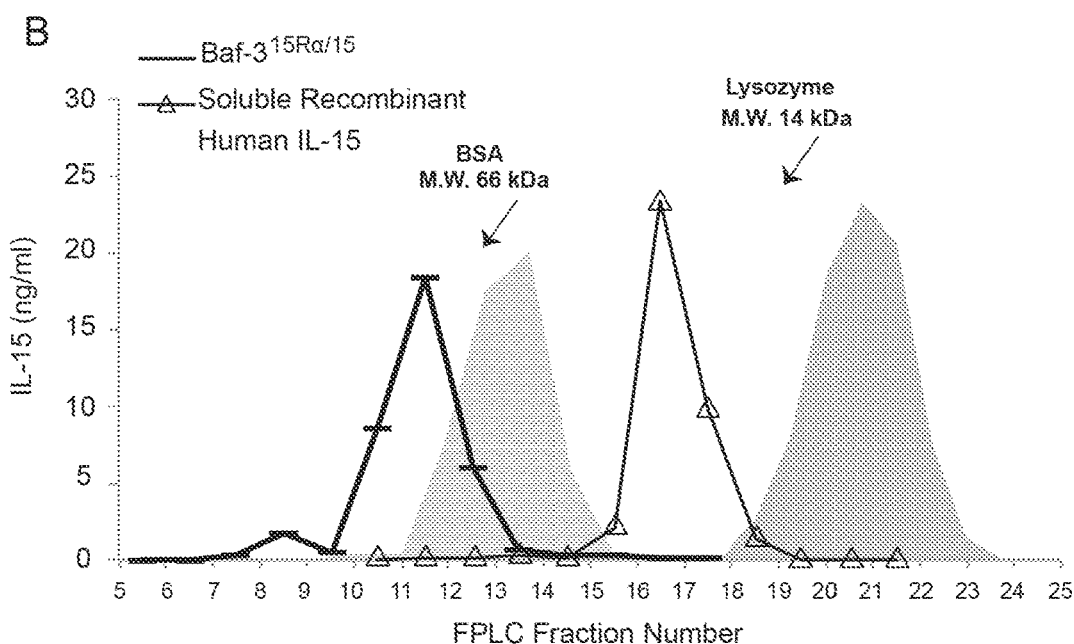
Figure 4C:
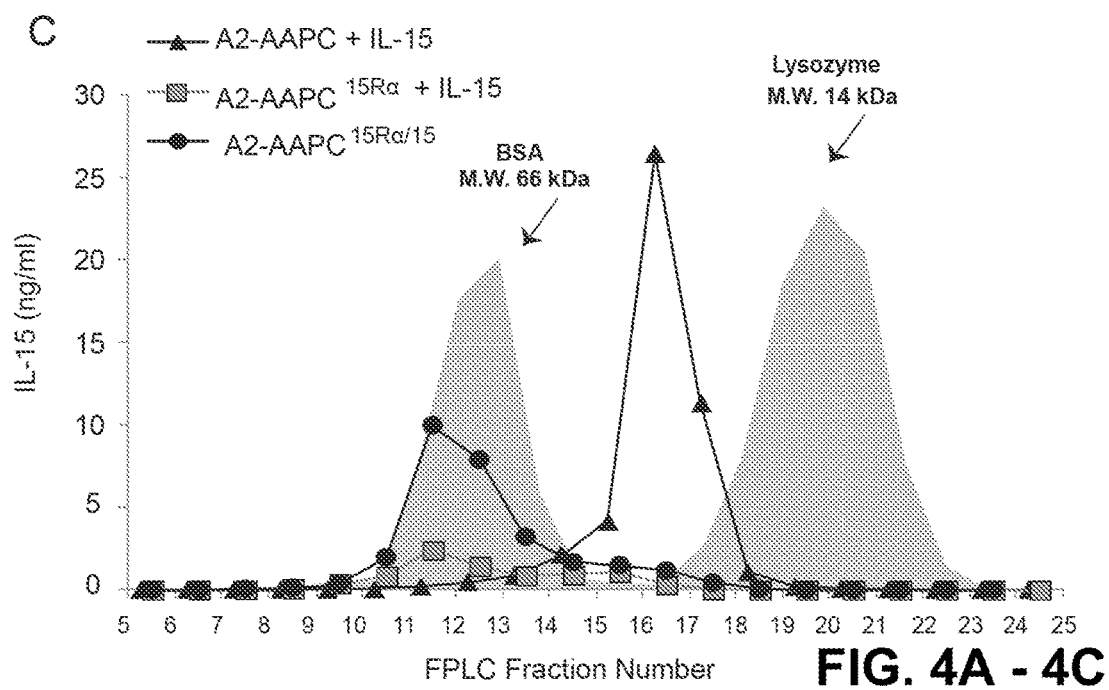

It was examined in the study of this example whether IL-15 preferentially exists as a complex bound to IL-15Rα in the case of genetically modified cells expressing both human IL-15 and IL-15Rα genes (A2-AAPC$^{15R\alpha/15}$ and Baf-3$^{15R\alpha/15}$), and these genetically modified cells were compared with sIL-15 loaded A2-AAPC$^{15R\alpha}$. In western blot analysis, performed on concentrated cell supernatants that had retained all detectable IL-15 (see methods in Section 6.2), both IL-15 and IL-15Rα proteins were detected as a high molecular weight (HMW) band under non-reducing conditions in Baf-3$^{15R\alpha/15}$, A2-AAPC$^{15R\alpha/15}$ and A2-AAPC$^{15R\alpha}$ cultures (FIG. 4A). Upon fractionation of the concentrated supernatants and FPLC analysis, it was confirmed that the immunologically detectable IL-15 was exclusively present in the HMW fractions (FIG. 4B). Nevertheless, in sIL-15 supplemented supernatants of A2-AAPC, IL-15 was only detected in LMW fractions (FIG. 4C). Based on these data, it was inferred that IL-15 existed as a complex with IL-15-Rα in both Baf-3$^{15R\alpha/15}$ and A2-AAPC$^{15R\alpha/15}$ (FIG. 4B, C).

Figure 5A:
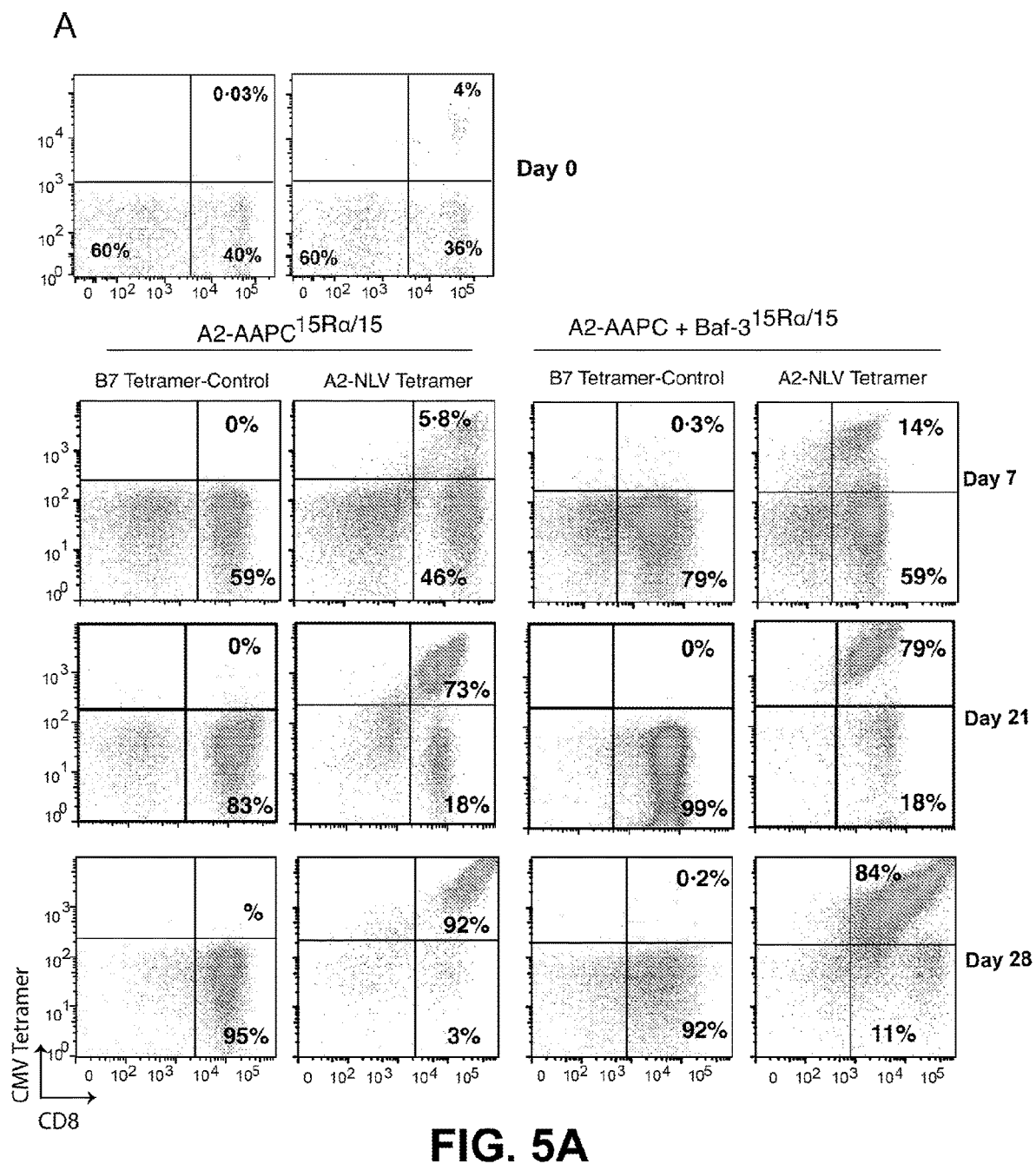
Figure 5B:
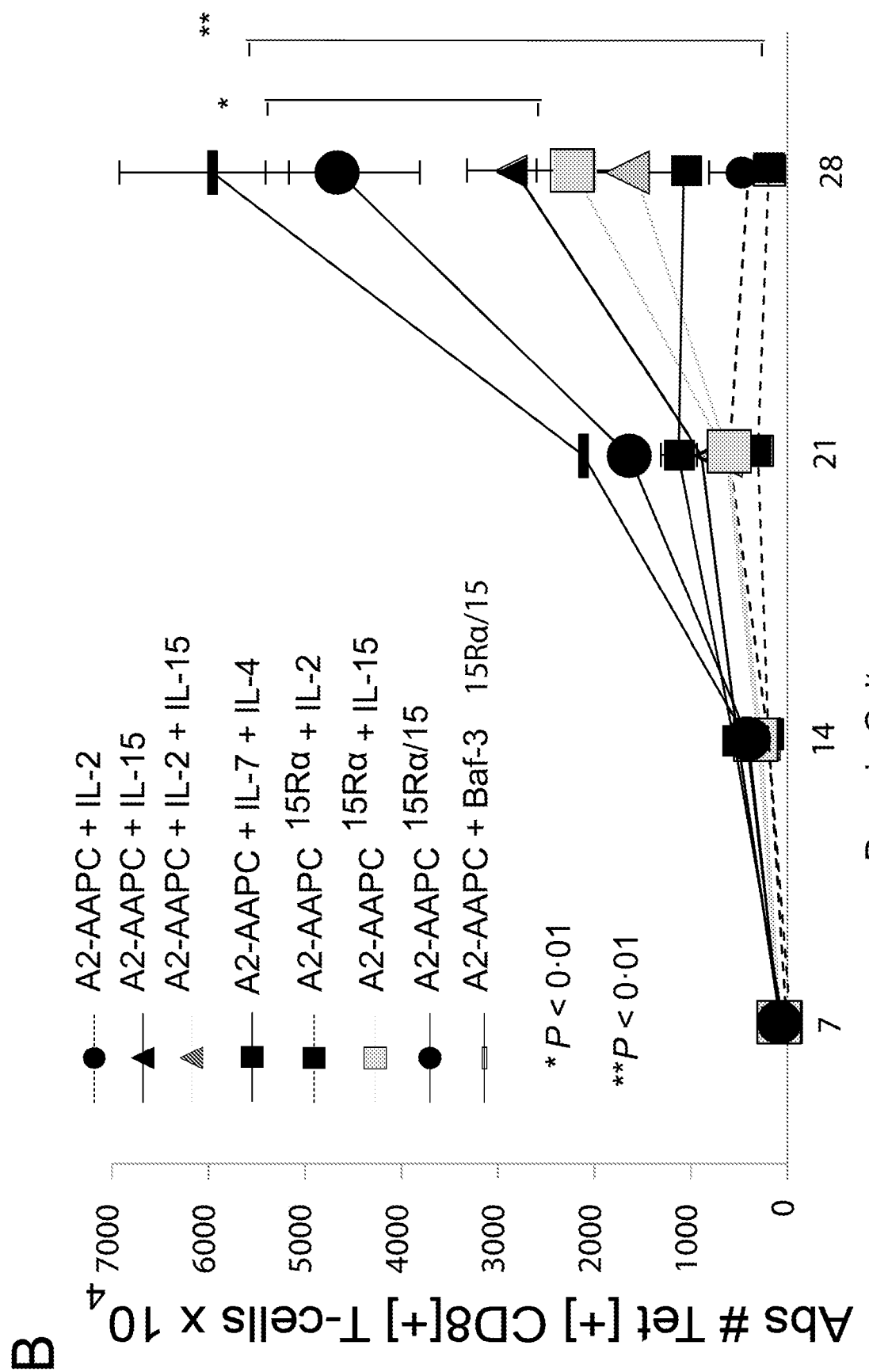
Figure 5C:
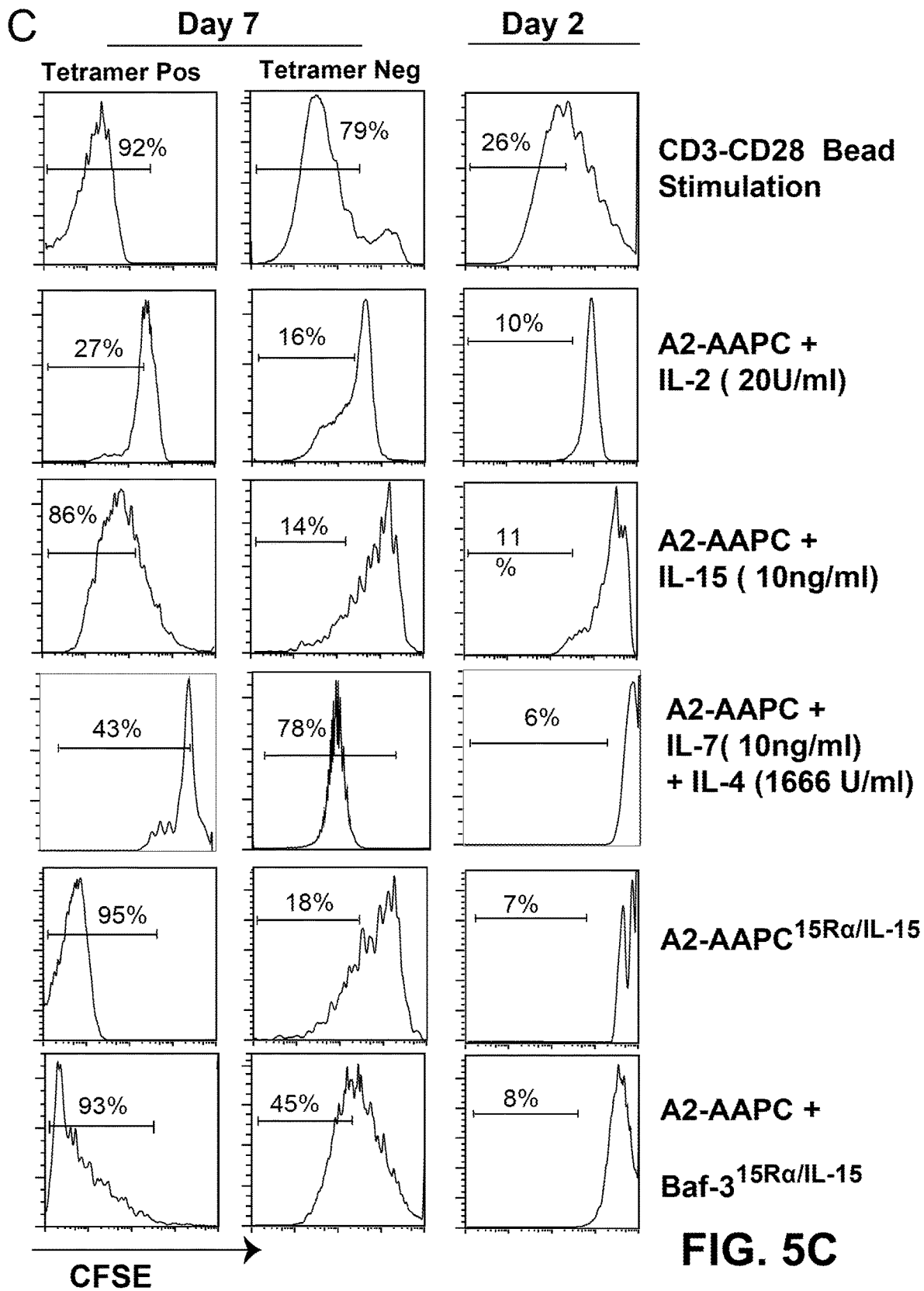

6.3.4. AAPC Co-Expressing IL-15Rα and IL-15 Support Continuous Enrichment of Antigen-Specific CD8⁺ T Cells During Prolonged In Vitro Expansion Next, the enrichment of antigen-specific T cells when stimulated in the presence of 15Rα/15 complexes was compared versus the enrichment of antigen-specific T cells when stimulated in the presence of sIL-15 or sIL-2. CMV-CTLs from 6 seropositive donors were expanded in vitro in parallel co-cultures with A2 AAPC$^{15R\alpha/15}$ with A2 AAPC supplemented with sIL-2 or sIL-15. As shown in a representative example in FIGS. 5A and 2A, in the first 7 days after culture initiation, a lower proportion of Tet⁺ T cells was observed within A2-AAPC$^{15R\alpha/15}$ stimulated T cells (5.8%) compared to sIL-15 or sIL-2 supplemented A2-AAPC T cell cultures (21% and 16% respectively-FIG. 2A). However, after the initial week, A2-AAPC$^{15R\alpha/15}$ sensitized T cells demonstrated robust enrichment of NLV epitope specific Tet⁺ T cells from 5.8% to 92% at 28 days, thus achieving the highest enrichment within all conditions. This enhanced enrichment of Tet⁺ CMV-CTLs with A2-AAPC$^{15R\alpha/15}$ was confirmed in triplicate analyses of CTLs from each donor (p<0.01). In T cell proliferation assays measuring CFSE dilution, Tet⁺ T cells within T cells stimulated with A2-AAPC$^{15R\alpha/15}$ or with A2-AAPC+Baf-3$^{15R\alpha/15}$ demonstrated a higher proliferative rate compared to sIL-15, sIL-7 or sIL-2 supplemented T cells. A higher proliferation of Tet$^{Neg}$ T cells was also observed within A2-AAPC+Baf-3$^{15R\alpha/15}$ and IL-7+IL-4 stimulated T cells. However, for A2-AAPC+Baf-3$^{15R\alpha/15}$ the proliferation of Tet⁺ T cells remained higher than the Tet$^{Neg}$ T cells (FIG. 5C). The delayed enrichment of Tet⁺ T cells with A2-AAPC$^{15R\alpha/15}$ could therefore be attributed to early non-specific expansion of T cells mediated by the 15Rα/15 complexes. Expansion of non-specific T cells within sIL-7+sIL-4 stimulated T cells would also explain the lower enrichment of Tet⁺ T cells compared to IL-15 stimulated T cells.

Figure 5D:
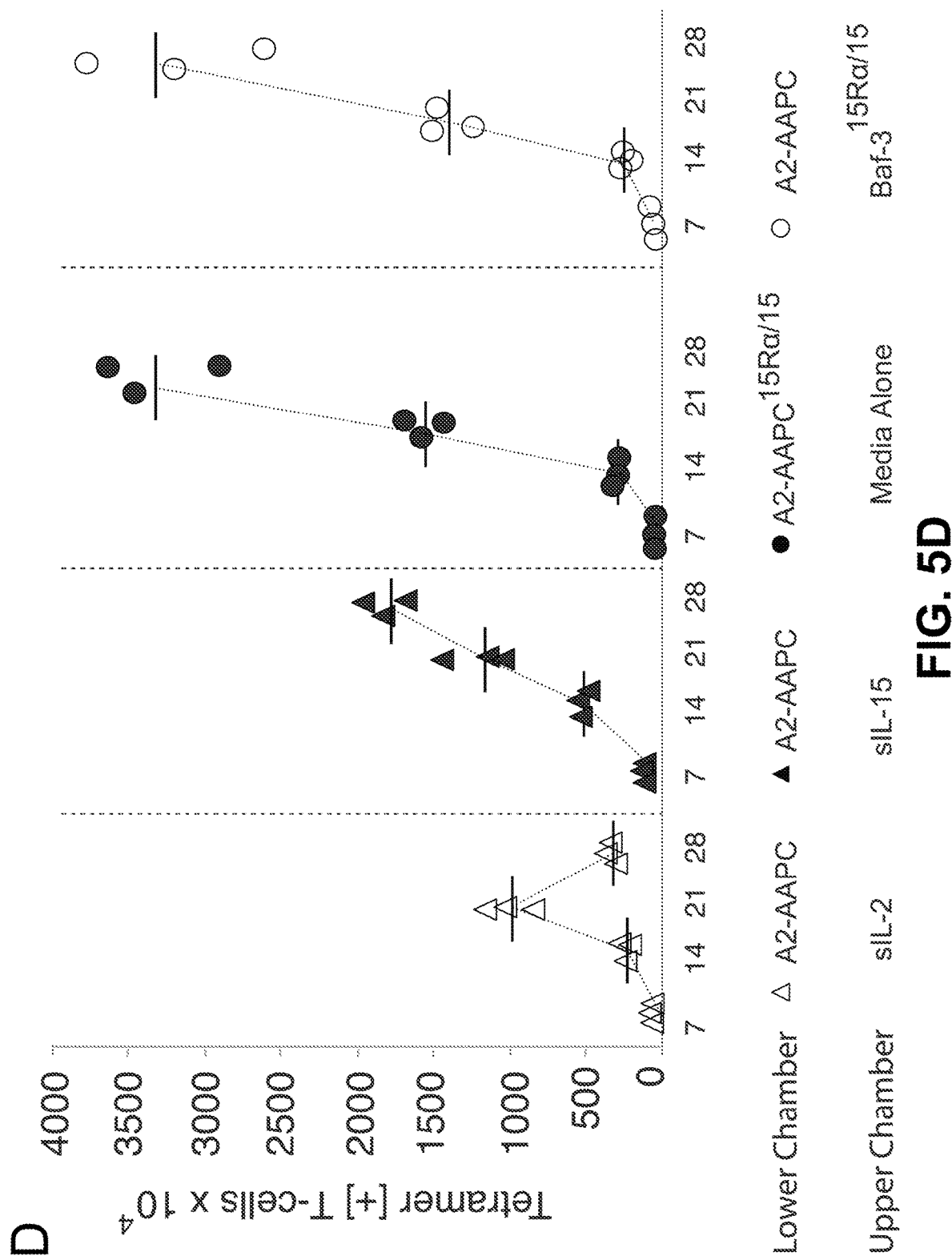

6.3.5. Soluble and Membrane Bound 15Rα/15 Complexes are Equally Efficient in Stimulating High Proportions of Antigen-Specific T Cell Expansion Thus far, this study demonstrated secretion of significant quantities of IL-15, predominantly existing as a stable 15Rα/15 complex, in cell supernatants of A2-AAPC$^{15R\alpha/15}$ and Baf-3$^{15R\alpha/15}$. It was next examined whether 15Rα/15 complexes presented on neighboring non-APC cells or soluble/secreted complexes could mediate the same effects as APC expressed 15Rα/15. Parallel T cell co-cultures with A2-AAPC were established in transwell culture plates where the supplemented cytokines were separated from the T cell co-cultures by a 3 μm permeable membrane that would permit the diffusion of soluble cytokines (sIL-15, sIL-2) and secreted 15Rα/15 complexes from Baf-3$^{15R\alpha/15}$ or A2-AAPC$^{15R\alpha/15}$, but would not enable cellular contact with the membrane bound 15Rα/15 complexes. Within T cells stimulated by A2-AAPCs in the presence of soluble 15Rα/15 permeating through the transwell membrane, a significantly higher enrichment of Tet⁺ T cells compared to sIL-2 or sIL-15 supplemented T cells (p<0.01) was observed. These yields were similar to the overall yields of Tet⁺ T cells obtained with CMV-CTLs generated by direct co-culture with A2-AAPC$^{15R\alpha/15}$ (FIG. 5D).

Figure 6A:
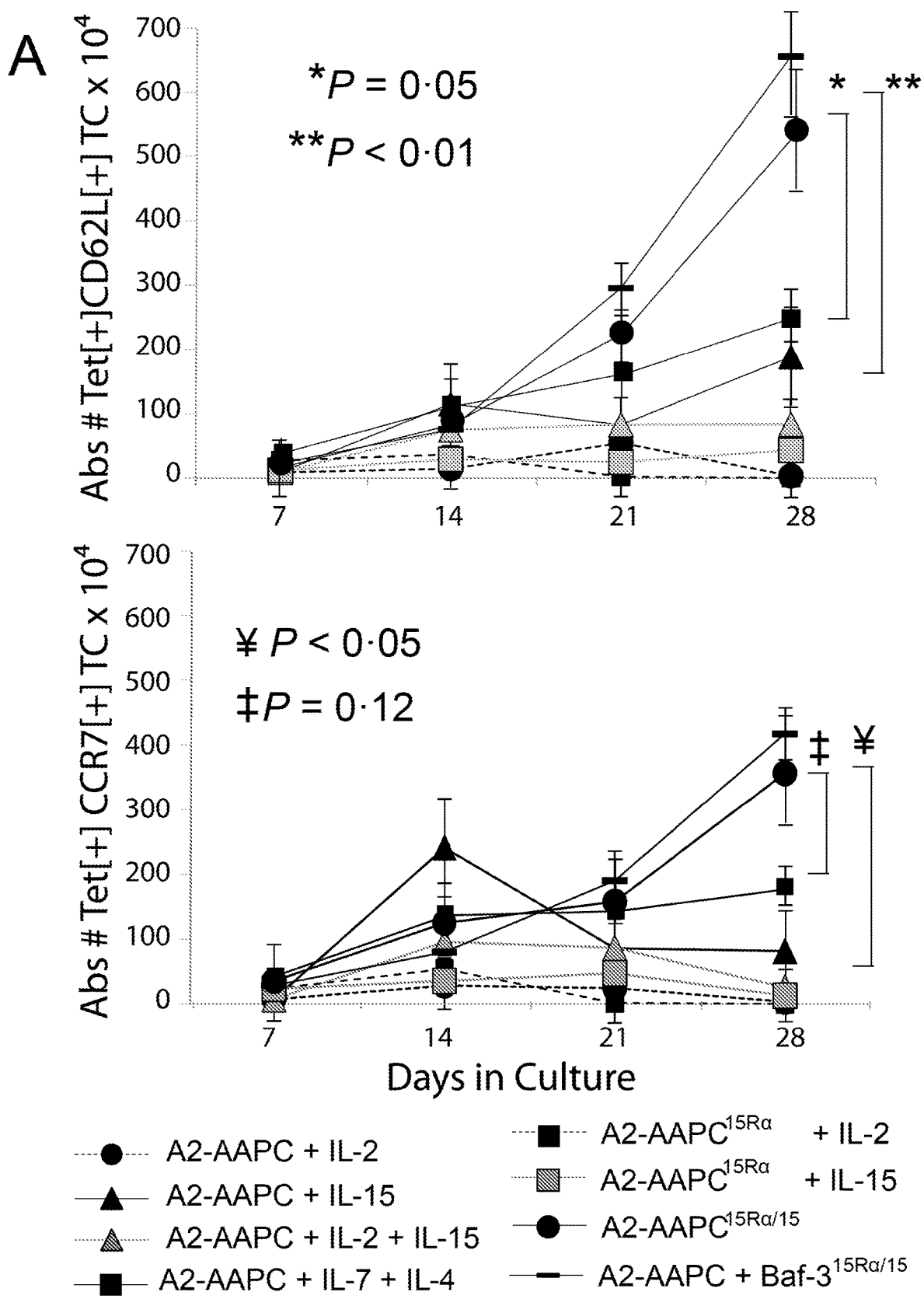
Figure 6B:
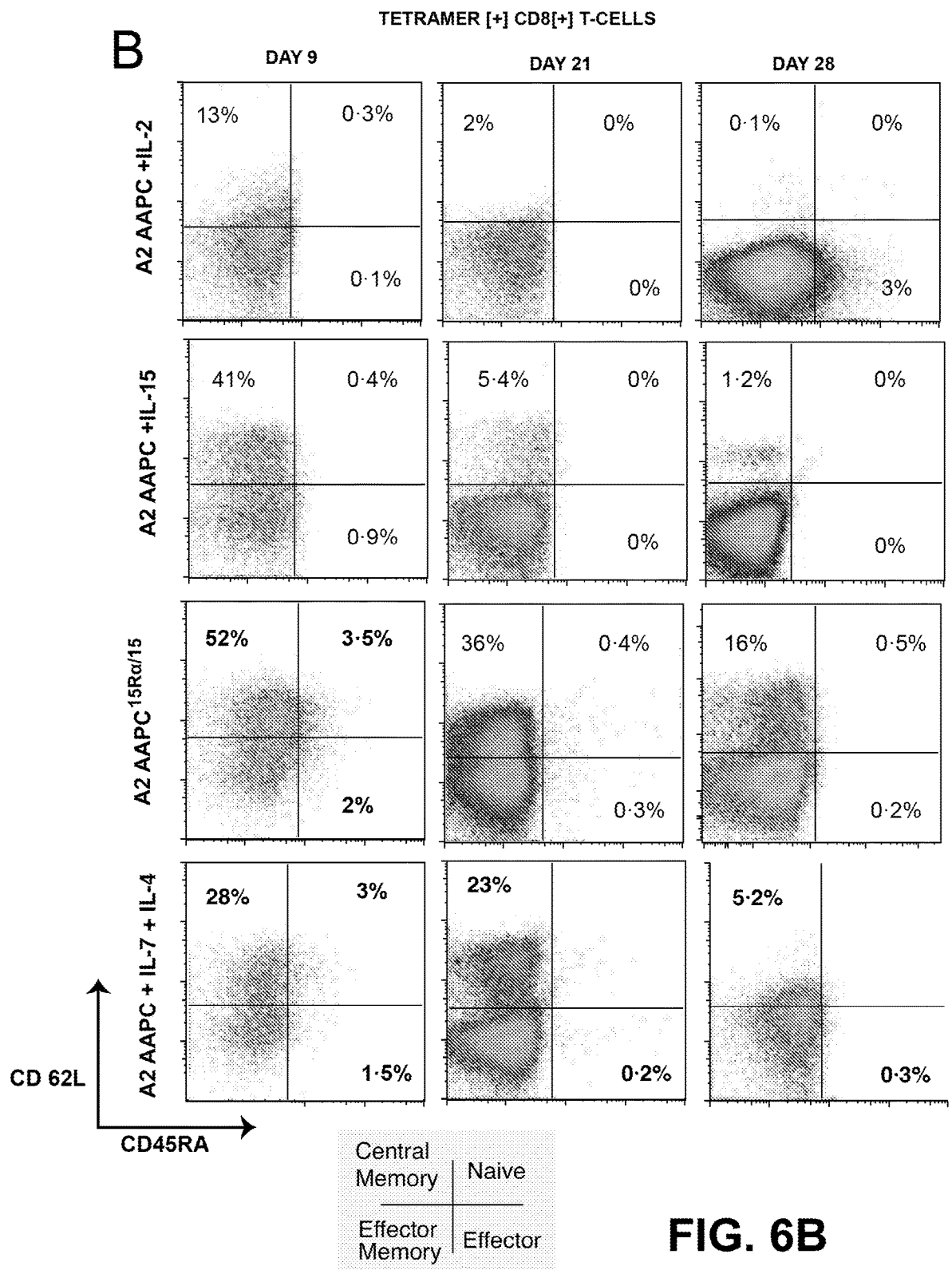

6.3.6. 15Rα/15 Stimulation Supports the Expansion of Central Memory Phenotype Antigen Specific T-Cells The above data clearly demonstrated that 15Rα/15 supported superior enrichment of antigen-specific T cells. For adoptive immunotherapy applications, it was then asked if 15Rα/15 could potentiate the enrichment of antigen-specific T cells bearing a central memory phenotype that would have longer in vivo persistence after infusion. The expression of CD62L and CCR7 was examined within A2-NLV Tet⁺ T cells expanded in vitro under different cytokine conditions. As with sIL-2, within the first 14 days, all sIL-15 CMV-CTLs also had minimally detectable proportions of CD62L⁺ and CCR7⁺ T cells (FIG. 6A), but because of the overall T cell stimulatory effects of sIL-15, these residual CD62L⁺/CCR7⁺ Tet⁺ T cells (T$_{CM}$) expanded 3-5 fold between 14-21 days in culture (Table 1), at which time no Tet⁺ T$_{CM}$ cells could be detected in sIL-2 CTLs. In contrast, A2-AAPC$^{15R\alpha/15}$ stimulated CMV-CTLs demonstrated a sustained expansion of Tet⁺ T$_{CM}$ through 28 days (FIG. 6A) resulting in a 600-1000 fold expansion (Table 1), and a total yield at 21 days of 2-3×10⁶ and approximately 5×10⁶ by 28 days. These yields of Tet⁺ T$_{CM}$ were significantly higher than in sIL-15 CTLs, which generated only 0.5-1×10⁶ at 21 days and 1.5×10⁶ Tet⁺ T$_{CM}$ at 28 days (p<0.01). In a representative example shown (FIG. 6B), 15Rα/15 stimulated T cells (A2-AAPC$^{15R\alpha/15}$ or A2-AAPC+Baf-3$^{15R\alpha/15}$) maintained a sizable proportion of Tet⁺ CD62L⁺ T cells even at later time points between 21 and 28 days after initial stimulation; ranging from 16% to 36%, suggesting a role for 15Rα/15 complexes in sustaining T$_{CM}$ expansion during continuous antigenic stimulation. Of note, expansion of CD62L⁺ and CCR7⁺ Tet⁺ T$_{CM}$ cells was also observed with sIL-7+sIL-4 stimulated CTLs, which was intermediate between sIL-15 and 15Rα/15 stimulated T cells (FIG. 6A). The Tet⁺ T cells expanded in the presence of sIL-7+sIL-4 demonstrated a higher proportion of CD62L⁺ at day 21 that was comparable to 15Rα/15 and much higher than sIL-15 and sIL-2 stimulated T cells. However, by day 28, the highest proportion of CD62L⁺ Tet⁺ T$_{CM}$ cells were elicited within 15Rα/15 stimulated T cells as shown in a representative example (FIG. 6B).

Figure 7A:
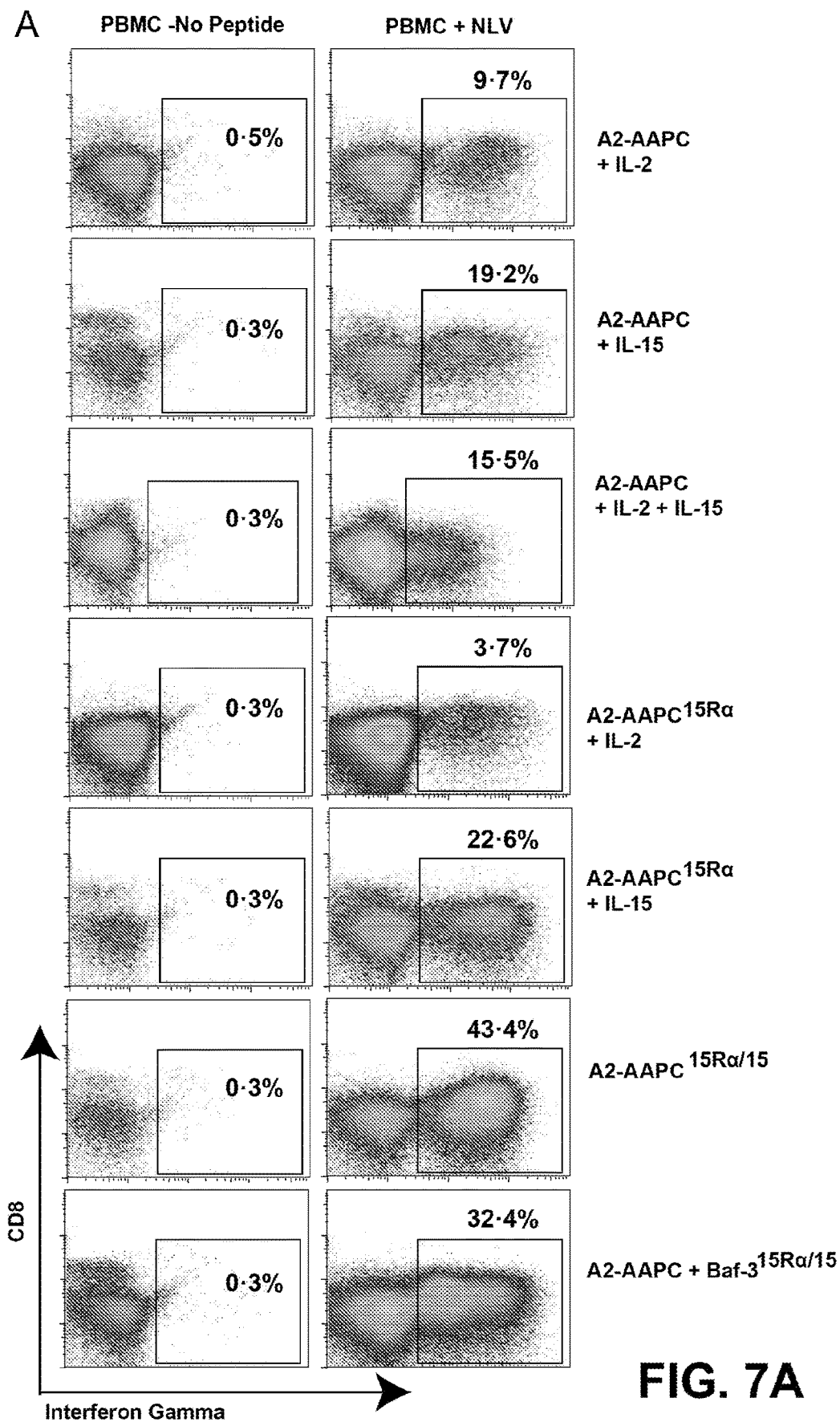

6.3.7. 15Rα/15 Complexes Support the Generation of High Avidity Antigen-Specific T Cells Next, the effect of 15 Rα/15 complexes on the functional capacity of CMV-CTLs was evaluated in comparison to sIL-15. T cell cytokine secretion was initially examined 21 days after stimulation in response to secondary stimulation with 10 nM NLV loaded autologous APCs. As shown in one representative donor (FIG. 7A), 15 Rα/15 stimulated T cells (A2-AAPC$^{15R\alpha/15}$ and Baf-3$^{15R\alpha/15}$) elicited a markedly higher proportion of IFNγ⁺ CD8⁺ T cells (43.4% and 32.4%) compared to sIL-15 stimulated T cells with either A2-AAPC or A2-AAPC$^{15R\alpha}$ (19.2% and 22.6%). sIL-2 supplemented CMV-CTLs elicited lower proportions of NLV responsive IFNγ⁺ CD8⁺ T cells with either A2-AAPC or A2-AAPC$^{15R\alpha}$ stimulation (9.7% and 3.7%), which could be augmented with additional sIL-15, but the yields were still lower than those achieved within sIL-15 alone supplemented T cells (15.5% vs 19.2%) (FIG. 7A). Overall, 15 Rα/15 stimulated T cells (A2-AAPC$^{15R\alpha/15}$ and Baf-3$^{15R\alpha/15}$) produced the highest yield of NLV-responsive IFNγ⁺ CD8⁺ T cell numbers, generating a median of 1×10⁷ and 8.3×10⁶ epitope specific T cells respectively, compared to a median of 1-3×10⁶ IFNγ⁺ CD8⁺ T cells in other conditions (p<0.001)

Figure 7B:
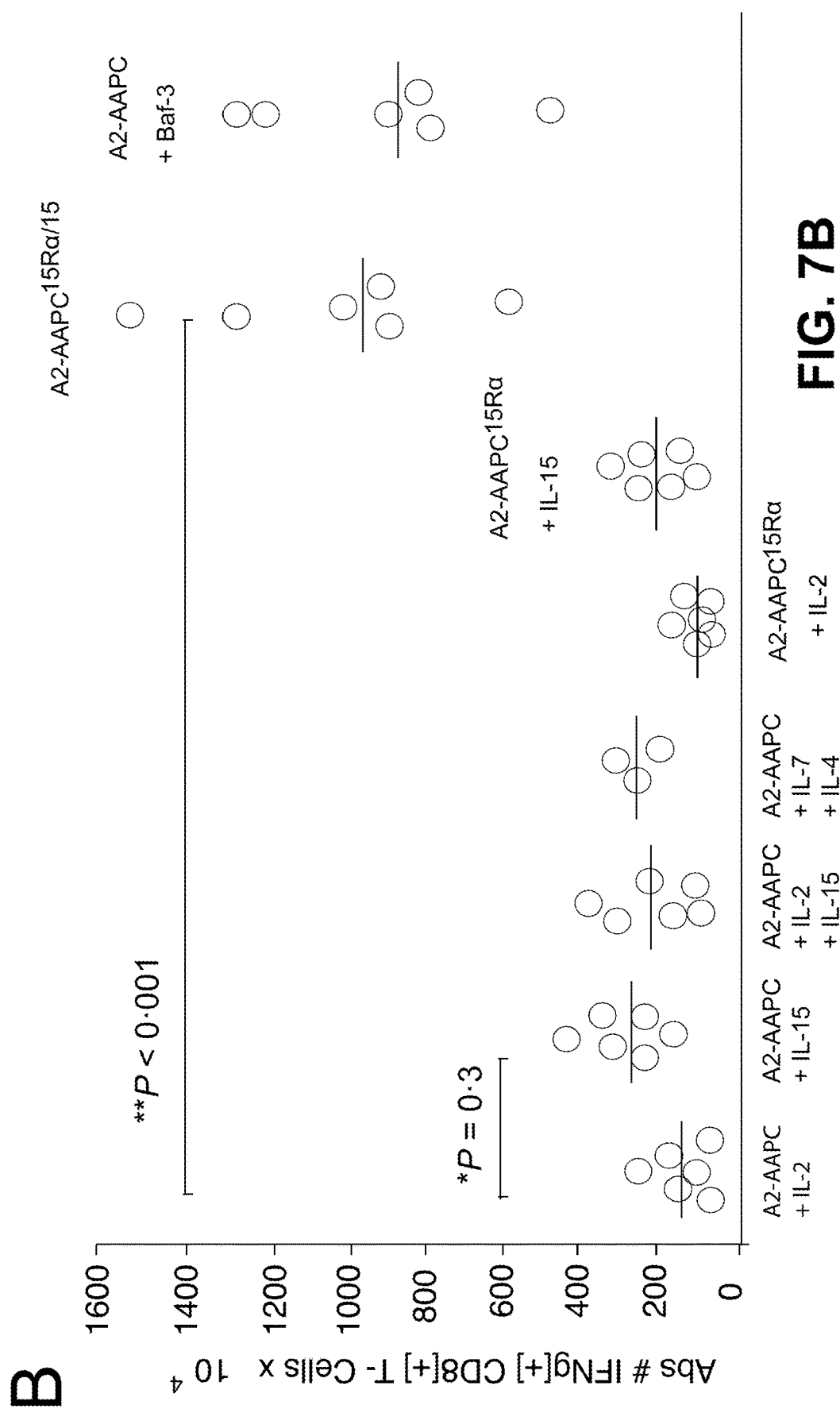
Figure 7E:
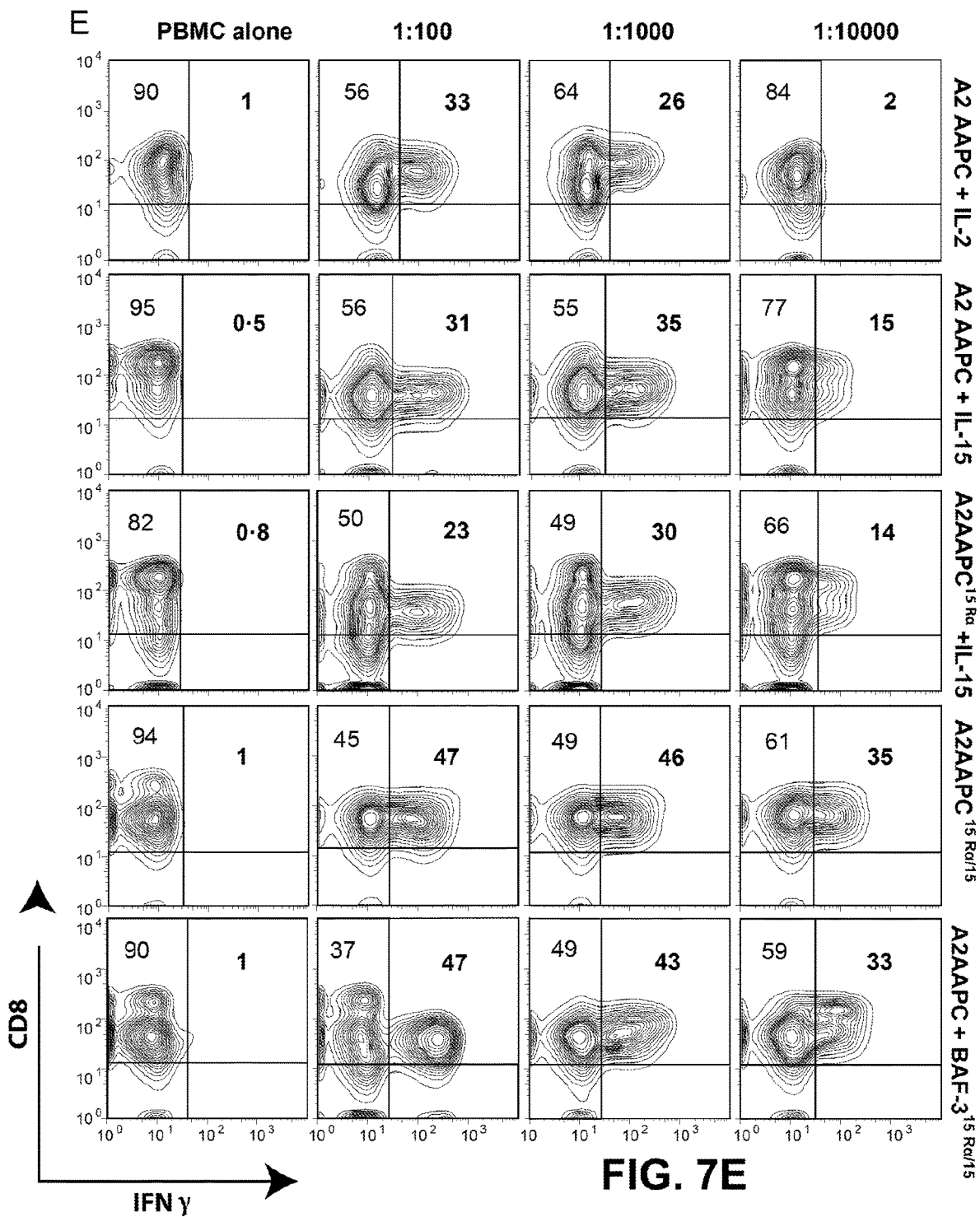

(FIG. 7B and Table 1). T cells stimulated with soluble, secreted 15Rα/15 complexes delivered via a permeable membrane also demonstrated similarly high proportions of IFNγ⁺ CD8⁺ T cells in response to NLV peptide (FIG. 7C) as those observed in T cells stimulated by direct co-culture with A2-AAPC$^{15R\alpha/15}$ and Baf-3$^{15R\alpha/15}$.

To further delineate the most functionally avid T cells, T cell cytokine secretion in response to titrated doses of the NLV peptide (10 nM, 10 pM, 0.1 pM) was examined. In these studies, significant differences in T cell responses could only be discerned at peptide concentrations of ≤10⁻¹³M (0.1 pM) within T cells expanded under different cytokine conditions (FIG. 7D). At higher peptide concentrations, there were minimal differences in T cell responses in any of the cytokine conditions. In a representative example (FIG. 7E), at $10^{-13}$M peptide, no responses were elicited in sIL-2 supplemented T cells, while 15Rα/15 stimulated T cells (A2-AAPC$^{15R\alpha/15}$ or A2-AAPC+Baf-3$^{15R\alpha/15}$) elicited robust IFNg⁺ CD8⁺ T cell responses. At $10^{-13}$M peptide, diminishing responses were elicited in T cells supplemented with sIL-15 as well as sIL-7+sIL-4, with 10% and 14% IFNγ⁺ CD8⁺ T cells compared to 23% and 32% enumerated in response to $10^{-12}$M peptide in sIL-15 CTLs (p<0.05) (FIG. 7D, E).

Figure 8A:
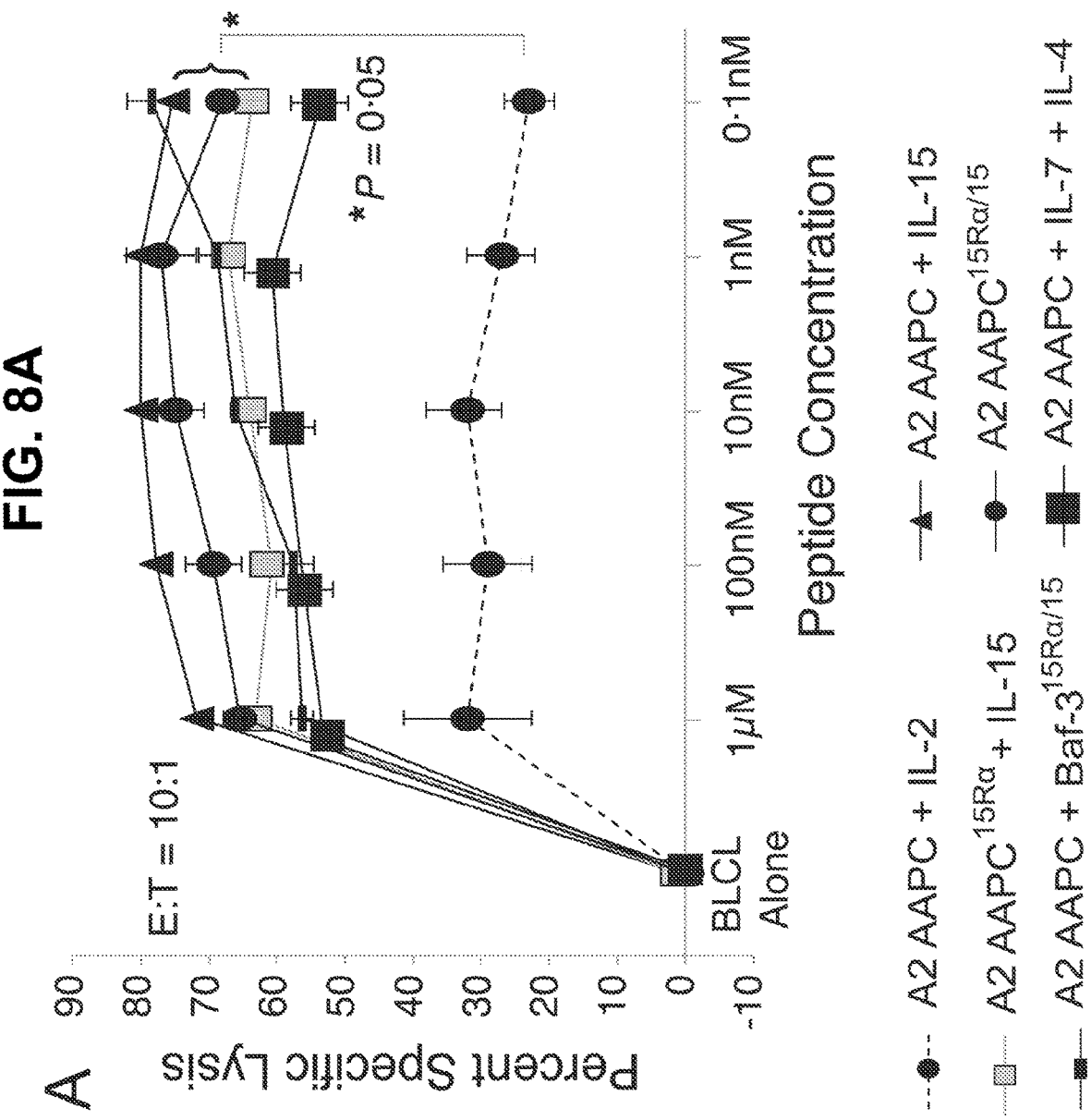

6.3.8. 15Rα/15 Stimulated Antigen Specific T Cells Efficiently Lyse Targets at Lower E:T Ratios Then the T cell cytotoxic activity of CMV-CTLs was evaluated as another differentiating parameter of functional activity. Lysis of autologous targets loaded with titrated doses of the NLV peptide, and at graded E:T ratios was examined. At concentrations ≥0.1 nM, all IL-15 supplemented CTLs equally lysed the peptide loaded autologous targets without exhibiting any explicit cytotoxicity hierarchy. T cells supplemented with sIL-7+sIL-4 also demonstrated similar cytotoxic activity at graded peptide concentrations. In comparison, sIL-2 supplemented CTLs exhibited inferior cytotoxicity at all peptide concentrations (p<0.05) (FIG. 8A). Peptide concentrations lower than 0.1 nM did not elicit CTL toxicity in any condition.

Figure 8B:
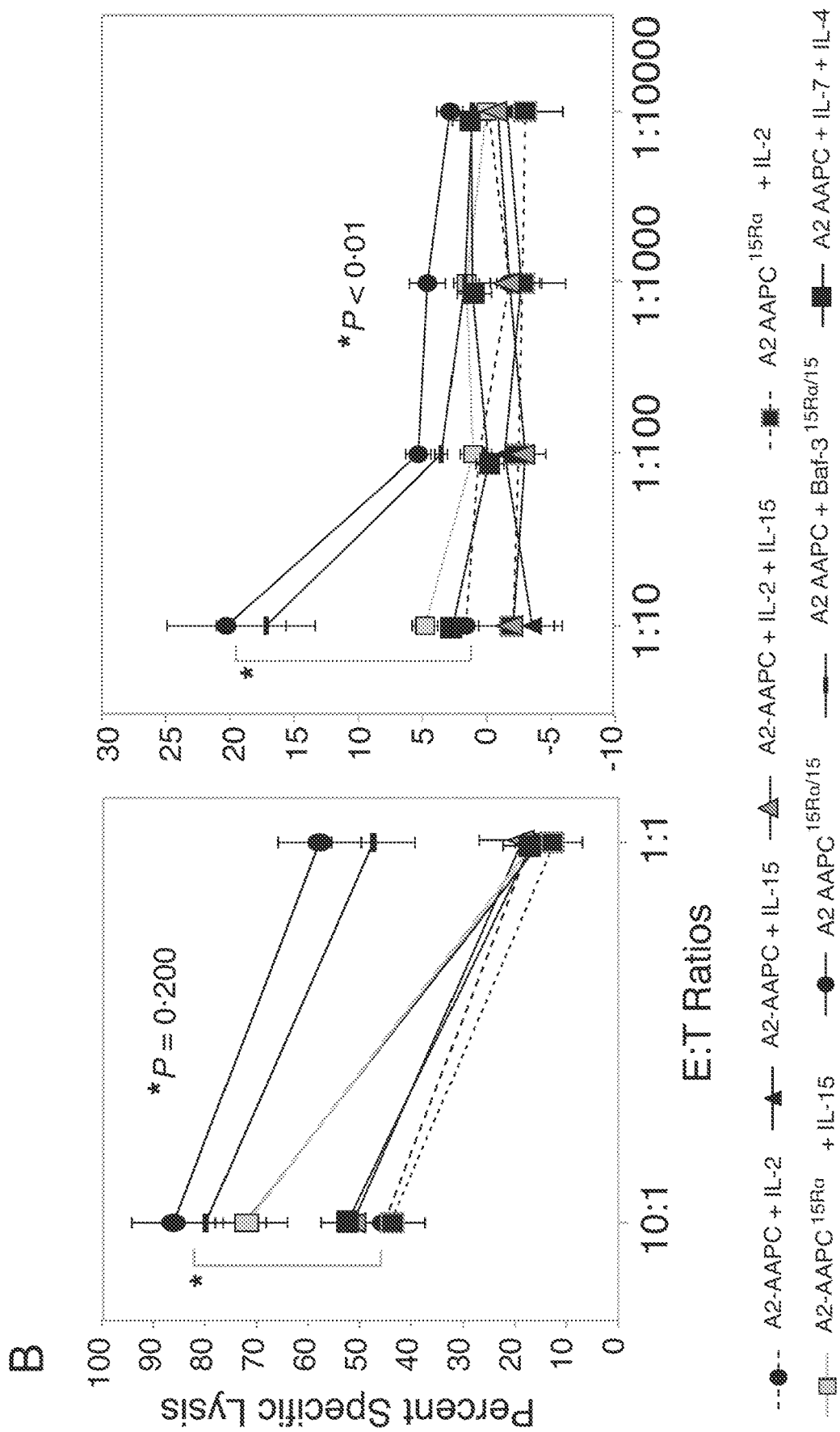
Figure 8C:
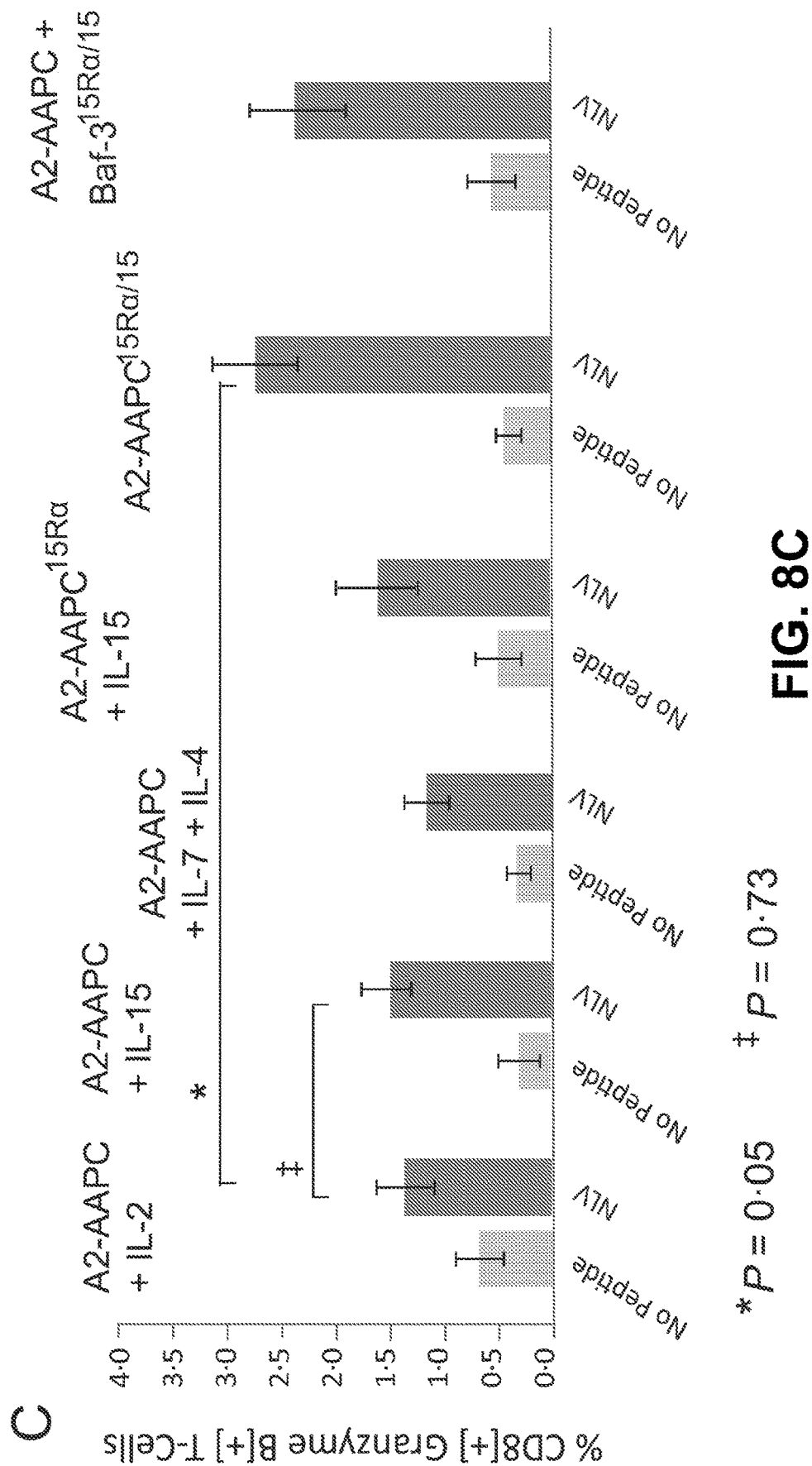

Then the cytotoxic activity of CMV-CTLs was evaluated at graded E:T ratios. This permitted the recognition of differential cytotoxic activity for 15Rα/15 stimulated CMV-CTLs compared to other conditions. At E:T ratios lower than 10:1, only 15Rα/15 stimulated CMV-CTLs demonstrated sufficient cytotoxic activity, which was markedly diminished at this E:T ratio in all other cytokine conditions (p<0.01) (FIG. 8B). A higher proportion of granzyme B generating CD8⁺ T cells was also observed within 15Rα/15 stimulated CMV-CTLs in comparison to sIL-2, sIL-15 or sIL-7+sIL-4 supplemented T cells (p<0.05) (FIG. 8C). Taken together, this analysis permitted a functional distinction between CTLs stimulated in different cytokine conditions, and 15Rα/15 stimulation emerged as a means to generate high avidity CD8⁺ antigen-specific T cells for adoptive immunotherapy applications.

6.4. Discussion

Adoptive therapy with antigen-specific transplant donor derived T cells is established as a viable and effective approach for the treatment of life threatening viral infections complicating allogeneic hematopoietic cell or organ transplants (Doubrovina et al., 2012, Blood 119:2644-2656; Heslop et al., 1996, Nat Med 2:551-555; Koehne et al., 2015, Biol Blood Marrow Transplant 21:1663-1678; Feuchtinger et al., 2010, Blood 116:4360-4367). Induction of cancer remission has also been achieved in a proportion of chemotherapy refractory patients after infusion of in vitro expanded autologous tumor infiltrating lymphocytes (Rosenberg et al., 1988, N Engl J Med 319:1676-1680) as well as tumor antigen-specific T cells (Rosenberg and Dudley, 2004, Proc Natl Acad Sci USA 101 Suppl 2:14639-14645; Hunder et al., 2008, N Engl J Med 358:2698-2703; Morgan et al., 2006, Science 314:126-129). However, sustained responses have only been achieved in patients with detectable in vivo expansion of the adoptively transferred T cells (Klebanoff et al., 2005, Proc Natl Acad Sci USA 102:9571-9576). Since then, studies in animal tumor models have shown that infusion of highly differentiated tumor antigen-specific T cells are less effective in eradicating tumors compared to naive and early effector T cells (Gattinoni et al., 2005, J Clin Invest 115:1616-1626). These observations have placed a major emphasis on the development of methodologies that not only enhance the yields of antigen-specific T cells for adoptive therapy, but also the selective expansion of less differentiated long-lived memory T cells capable of inducing durable responses (Ahmed and Gray, 1996, Science 272:54-60). Techniques for augmenting the efficacy of adoptively transferred T cells are equally desirable to attain higher rates of remission.

IL-15 has been shown to play a central role in the stimulation and maintenance of antigen-specific CD8⁺ memory T cells when presented in complex with its high affinity receptor IL-15Rα to responding T cells (Zhang et al., 1998, Immunity 8:591-599; Burkett et al., 2004, J Exp Med 200:825-834; Waldmann et al., 2001, Immunity 14:105-110; Surh and Sprent, 2008, Immunity 29:848-862; Schluns et al., 2004, Blood 103:988-994). IL-15 signaling through the PI3K/AKT pathway has been shown to even revive the exhausted proliferative function of effector memory phenotype T cells specific for infectious agents or tumors in a TCR independent manner (Kim et al., 2007, J Immunol 179:6734-6740). In a study evaluating acute graft rejection in renal transplant recipients, IL-15 was shown to induce proliferation of CD8⁺ memory T cells that was independent of B7-CD28 co-stimulation (Traitanon et al., 2014, Am J Transplant 14:1277-1289). These data suggest that in tumors that poorly express HLA or tumor antigens, or lack expression of co-stimulatory molecules, IL-15 would be able to endow the host T cells or adoptively transferred T cells with the necessary signals to proliferate and lyse tumor cell targets. Since the expression of IL-15Rα is not optimal in vivo, IL-15 monotherapy would not be as effective without IL-15Rα.

The study presented in this example defined the conditions required for the stable expression and generation of 15Rα/15 in vitro, and then compared the effects of soluble IL-15 and other gamma chain cytokines with 15Rα/15 in their capacity to stimulate antigen-specific T cell expansion. This study also generated a novel cell based APC system that can present and secrete stable 15Rα/15 using genetically modified cells either transduced with IL-15Rα alone or with both IL-15 and IL-15Rα genes (A2-AAPC$^{15R\alpha/15}$ and Baf-3$^{15R\alpha/15}$). This study established that both IL-15 and IL-15Rα genes are required to be expressed in the same cell to form stable 15Rα/15 complexes, and that the IL-15 gene was not expressed when transduced without IL-15Rα. Such an obligate requirement for binding with the alpha chain receptor for stabilization and effect has not been described for other gamma chain cytokines including IL-7 or IL-2. The effects of 15Rα/15 complexes generated by these cells on the in vitro enrichment, memory phenotype and functional capacity of antigen-specific T cells were examined. The data demonstrated that 15Rα/15 complexes can not only augment the yields of antigen-specific T cells, but also specifically enrich $T_{CM}$ phenotype cells that have the potential to induce durable remissions after adoptive transfer. Importantly, cells generating 15Rα/15 complexes supported the steady expansion of antigen-specific CD62L$^+$ Tet$^+$ $T_{CM}$ cells, which was not observed in sIL-15 supplemented cultures. Furthermore, in cultures where 15Rα/15 expressing cells were separated from T cells by semipermeable membranes, the secreted and soluble 15Rα/15, potentially presenting IL-15 in a cis configuration, permeated the membrane and efficiently stimulated responding CD8$^+$ T cells without cell to cell contact. In fact 15Rα/15 complexes can not only signal to responding neighboring lymphocytes when bound to cell membranes, but also as soluble complexes they can get internalized into responding lymphocytes and lead to sustained stimulation (Bergamaschi et al., 2008, J Biol Chem 283:4189-4199; Tamzalit et al., 2014, Proc Natl Acad Sci USA 111:8565-8570; Mortier et al., 2009, Immunity 31:811-822). However, in the study by Tamzalit et al. (Tamzalit et al., 2014, Proc Natl Acad Sci USA 111:8565-8570), cell to cell contact was shown to be essential for the internalization of 15Rα/15 released upon cleavage from cell surface to effectively stimulate responding CD8 and NK cells. That study also demonstrated stable surface expression of 15Rα/15 using IL-15Rα expressing cells loaded with sIL-15, which was not observed in the study presented in this example using sIL-15 loaded A2-AAPC$^{15R\alpha}$. In the system presented in this example, one cannot exclude the possibility that the soluble 15Rα/15 complexes could have bound to AAPCs not expressing either IL-15Rα or IL-15, or to activated T cells themselves, and thereby cross-stimulating adjacent T cells through direct cell contact (Schluns et al., 2004, Blood 103:988-994).

Importantly, the data herein illustrate that 15Rα/15 not only stimulates the expansion of $T_{CM}$ phenotype CTLs, but that the T cells generated exhibit high functional activity as evidenced by high IFNγ and granzyme B secretion, and response to minute concentrations of NLV (Oh et al., 2003, J Immunol 170:2523-2530) (FIG. 6 and Table 1). Such high-affinity pMHC/TCR interactions can override the requirement for CD8 engagement for cytotoxic activity (Kerry et al., 2003, J Immunol 171:4493-4503), suggesting that, by promoting the expansion of high avidity T cells, 15Rα/15 could be an invaluable reagent for the expansion of antigen-specific T cells responding to less immunogenic antigens such as self tumor antigens. Indeed, 15Rα/15 complexes expressed on langerhans cells have been shown to overcome tolerance and stimulate the expansion of WT-1 specific T cells when electroporated with WT-1 mRNA (Romano et al., 2012, Blood 119:5182-5190). Such 15Rα/15 complexes could also be tremendously valuable for the expansion of T cells responding to subdominant epitopes that presumably have lower TCR avidities. Furthermore, infusion of these complexes may also enhance the function of tumor resident, low avidity T cells. In a recent study using the transgenic adenocarcinoma of the mouse prostate (TRAMP)-C2 murine tumor model, treatment with agonistic anti-CD40 in combination with sIL-15 resulted in tumor regressions in 70-100% of treated animals in comparison to 0-30% treated with antibody alone (Zhang et al., 2012, J Immunol 188:6156-6164). In that study, treatment with anti-CD40 augmented the IL-15 Rα expression on host DC resulting in the formation of 15Rα/15 complexes upon exposure to sIL-15, which then supported the expansion and cytotoxic activity of host tumor specific CD8$^+$ T cells and enhanced anti-tumor activity. Synergistic anti-tumor activity has also been demonstrated using combination of IL-15 and immune checkpoint inhibitors (Yu et al., 2012, Proc Natl Acad Sci USA 109:6187-6192; Yu et al., 2010, Clin Cancer Res 16:6019-6028).

In conclusion, the study presented in this example demonstrates that 15Rα/15 complexes are required for optimal IL-15 activity. The study further demonstrates that these 15Rα/15 complexes represent a potent biological reagent for in vitro expansion of highly functional long-lived antigen-specific $T_{CM}$ suitable for adoptive immunotherapy and may also prove useful as therapeutic agents for augmentation of antitumor activity when used in conjunction with other immunotherapies.

7. INCORPORATION BY REFERENCE

All references cited herein are incorporated herein by reference in their entirety and for all purposes to the same extent as if each individual publication or patent or patent application was specifically and individually indicated to be incorporated by reference in its entirety for all purposes.

Many modifications and variations of this invention can be made without departing from its spirit and scope, as will be apparent to those skilled in the art. The specific embodiments described herein are offered by way of example only, and the invention is to be limited only by the terms of the appended claims, along with the full scope of equivalents to which such claims are entitled.

What is claimed is:

1. A method of generating an expanded population of cells comprising antigen-specific CD62L+central memory T cells for therapeutic administration to a human patient having or suspected of having a pathogen or cancer, comprising ex vivo culturing a population of human blood cells comprising human antigen-specific T cells over a period of time in culture in the presence of soluble IL-15/IL-15Rα complexes while in the absence of cells recombinantly expressing soluble IL-15/IL-15Rα complexes, wherein the human antigen-specific T cells are specific to one or more antigens of the pathogen or cancer, and
wherein the IL-15Rα subunit in the soluble IL-15/IL-15Rα complexes in the culture present with the population of human blood cells is a fragment of wild-type human IL-15Rα that retains the ability to bind to IL-15 but lacks the ability to be anchored to the cell membrane by itself, and
wherein the IL-15 subunit and the IL-15Rα subunit are in a 1:1 molar ratio.

2. The method of claim 1, which further comprises adding the soluble IL-15/IL-15Rα complexes to the culture.

3. The method of claim 2, wherein said adding soluble IL-15/IL-15Rα complexes is such that the concentration of IL-15 in culture supernatant is $10^2$ to $10^3$ pg/ml upon said adding.

4. The method of claim 2, wherein said adding soluble IL-15/IL-15Rα complexes to the culture is done at the initiation of said ex vivo culturing and every 7 to 10 days thereafter during said ex vivo culturing.

5. The method of claim 1, wherein the period of time in culture is at least 21 days.

6. The method of claim 5, wherein the period of time in culture is 21 to 28 days.

7. The method of claim 1, wherein the human antigen-specific T cells recombinantly express one or more chimeric antigen receptors (CARs) recognizing the one or more antigens.

8. The method of claim 1, wherein the human antigen-specific T cells recombinantly express one or more T cell receptors (TCRs) recognizing the one or more antigens.

9. The method of claim 3, wherein said adding the soluble IL-15/IL-15Rα complexes to the culture is done at the initiation of said ex vivo culturing and every 7 to 10 days thereafter during said ex vivo culturing.

10. The method of claim 3, wherein the period of time in culture is at least 21 days.

11. The method of claim 4, wherein the period of time in culture is at least 21 days.

12. The method of claim 9, wherein the period of time in culture is at least 21 days.

13. The method of claim 10, wherein the period of time in culture is 21 to 28 days.

14. The method of claim 11, wherein the period of time in culture is 21 to 28 days.

15. The method of claim 12, wherein the period of time in culture is 21 to 28 days.

16. The method of claim 1, wherein the population of human blood cells at initiation of culture contains at least 90% central memory T cells (TCM cells).

17. The method of claim 1, wherein the one or more antigens are one or more antigens of a pathogen.

18. The method of claim 17, wherein the pathogen is a virus.

19. The method of claim 18, wherein the virus is cytomegalovirus (CMV).

20. The method of claim 18, wherein the virus is Epstein-Barr virus (EBV).

21. The method of claim 1, wherein the one or more antigens are one or more antigens of a cancer.

22. The method of claim 21, wherein the cancer is a blood cancer.

23. The method of claim 21, wherein the cancer is a cancer of the breast, lung, ovary, stomach, pancreas, larynx, esophagus, testes, liver, parotid, biliary tract, colon, rectum, cervix, uterus, endometrium, kidney, bladder, prostate, thyroid, brain, or skin.

24. The method of claim 21, wherein the one or more antigens is Wilms Tumor 1 (WT1).

25. The method of claim 24, wherein the cancer is multiple myeloma or plasma cell leukemia.

26. The method of claim 2, which further comprises thawing the soluble IL-15/IL-15Rα complexes from a cryopreserved stock before adding the soluble IL-1 5/IL-15Rα complexes to the culture.

27. The method of claim 1, wherein the human antigen-specific T cells are antigen-specific T cells generated by ex vivo sensitization.

\* \* \* \* \*